(12) United States Patent
Honma et al.

(10) Patent No.: US 6,635,782 B2
(45) Date of Patent: Oct. 21, 2003

(54) POLYHYDROXYALKANOATE AND MANUFACTURING METHOD THEREOF

(75) Inventors: Tsutomu Honma, Kanagawa (JP); Etsuko Sugawa, Kanagawa (JP); Tetsuya Yano, Kanagawa (JP); Takeshi Imamura, Kanagawa (JP); Takashi Kenmoku, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 32 days.

(21) Appl. No.: 09/951,720

(22) Filed: Sep. 14, 2001

(65) Prior Publication Data

US 2002/0160467 A1 Oct. 31, 2002

(30) Foreign Application Priority Data

| Sep. 14, 2000 | (JP) | 2000-279900 |
|---|---|---|
| Dec. 13, 2000 | (JP) | 2000-378827 |
| May 31, 2001 | (JP) | 2001-165238 |
| May 31, 2001 | (JP) | 2001-165509 |
| Sep. 11, 2001 | (JP) | 2001-275063 |

(51) Int. Cl.$^7$ .............................................. C07C 69/76
(52) U.S. Cl. .......................................... 560/53; 560/51
(58) Field of Search ....................................... 560/51, 53

(56) References Cited

U.S. PATENT DOCUMENTS

| 4,393,167 A | 7/1983 | Holmes et al. |
|---|---|---|
| 4,876,331 A | 10/1989 | Doi |
| 5,135,859 A | 8/1992 | Witholt et al. |
| 5,200,332 A | 4/1993 | Yamane et al. |
| 5,292,860 A | 3/1994 | Shiotani et al. |

FOREIGN PATENT DOCUMENTS

| EP | 1 113 033 | 7/2001 |
|---|---|---|
| JP | 63-226291 | 9/1988 |
| JP | 5-49487 | 3/1993 |
| JP | 5-64591 | 3/1993 |
| JP | 5-214081 | 8/1993 |
| JP | 6-145311 | 5/1994 |
| JP | 6-284892 | 10/1994 |
| JP | 7-48438 | 2/1995 |
| JP | 7-265065 | 10/1995 |
| JP | 8-89264 | 4/1996 |
| JP | 9-191893 | 7/1997 |
| JP | 11-32789 | 2/1999 |
| JP | 2989175 | 12/1999 |

OTHER PUBLICATIONS

Alan Grund et al., "Regulation of Alkane Oxidation in Pspeudomonas putida," 123(2) *J. Bacteriol.* 546–556 (1975).

Y.B. Kim et al., "Preparation and Characterization of Poly (β–Hydroxyalkanoates) Obtained from *Pseudomonas oleovorans* with Mixtures of 5–Phenylvaleric Acid and n–Alkanoic Acids," 24 *Macromol.* 5256–5260 (1991).

Henry J. Vogel et al., "Acetylorinithinase of *Escherichia coli*: Partial Purification and Some Properties," 218 *J. Biol. Chem.* 97–106 (1956).

Katharina Fritzsche et al., "An Unusual Bacterial Polyester with a Phenyl Pendant Group," 191 *Macromol. Chem.* 1957–1965 (1990).

Suzette M. Aróstegui et al., "Bacterial Polyesters Produced by *Pseudomonas oleovorans* Containing Nitrophenyl Groups," 32 *Macromol.* 2889–2895 (1999).

Helmut Ritter et al., "Bacterial Production of Polyesters Bearing Phenoxy Groups in Side Chains, 1Poly(3–Hydroxy–5–Phenoxypentanoate–co–3–Hydroxy–9–Phenoxy–Nonanoate) From *Pseudomonas oleovorans,*" 195 *Macromol. Chem. Phys.* 1665–1672 (1994).

YoungBaek Kim et al., "Poly–3–Hydroxyalkanoates Produced From *Pseudomonas oleovorans* Grown with ω–Phenoxyalkanoates," 29 *Macromol.* 3432–3435 (1996).

Won Ho Park et al., "Epoxidation of Bacterial Polyesters with Unsaturated Side Chains. I. Production and Epoxidation of Polyesters From 10–Undecanoic Acid," 31 *Macromol.* 1480–1486 (1998).

Won Ho Park et al., "Epoxidation of Bacterial Polyesters with Unsaturated Side Chains. II. Rate of Epoxidation and Polymer Properties," 36 *J. Polym. Sci.* 2381–2387 (1998).

Yasuo Takagi et al., "Biosynthesis of Polyhydroxyalkanoate with a Thiophenoxy Side Group Obtained from *Pseudomonas putida*," 32 *Macromol.* 8315–8318 (1999).

Roland G. Lageveen et al., "Formation of Polyesters by *Pseudomonas oleovorans*: Effect of Substrates on Formation and Composition of Poly–(R)–3–Hydroxyalkanoates and Poly–(R)–3–Hydroxyalkenoates," 54(12) *Appl. Environ. Microbiol.* 2924–2932 (1988).

Yoshiharu Doi et al., "Biosynthesis and Characterization of a New Bacterial Copolyester of 3–Hydroxyalkanoates and 3–Hydroxy–ω–Chloroalkanoates," 23 *Macromol.* 3705–3707 (1990).

Joanne M. Curley et al., "Production of Poly(3–Hydroxyalkanoates) Containing Aromatic Substituents by *Pseudomonas oleovorans*," 29 *Macromol.* 1762–1766 (1996).

Kuno Jung et al., "Characterization of New Bacterial Copolyesters Containing 3–Hydroxyalkanoates and Acetoxy–3–Hydroxyalkanoates," 33 *Macromol.* 8571–8575 (2000).

Richard A. Gross et al., "Cyanophenoxy–Containing Microbal Polyesters: Structural Analysis, Thermal Properties, Second Harmonic Generation and In–Vivo Biodegradability," 39 *Polymer International* 205–213 (1996).

Marianela Andújar et al., "Polyesters Produced by *Pseudomonal oleovorans* Containing Cyclohexyl Groups," 30 *Macromol.* 1611–1615 (1997).

*Primary Examiner*—Paul J. Killos
(74) *Attorney, Agent, or Firm*—Fitzpatrick, Cella, Harper & Scinto

(57) ABSTRACT

To provide a novel polyhydroxyalkanoate and a manufacturing method by a microorganism capable of substantially reducing unintended monomer units and obtaining the polyhydroxyalkanoate in a high yield. A microorganism capable of synthesizing a novel polyhydroxyalkanoate having 3-hydroxy-substituted benzoylalkanoic acid as a monomer unit using a substituted benzoylalkanoic acid as a material is cultured in the medium containing a substituted benzoylalkanoic acid, then the polyhydroxyalkanoate produced in the cultured bacteria is extracted and recovered.

27 Claims, 7 Drawing Sheets

POLYHYDROXYALKANOATE AND MANUFACTURING METHOD THEREOF

BACKGROUND OF THE INVENTION

1. Field of the Invention

The present invention relates to a novel polyhydroxyalkanoate (hereinafter, sometimes abbreviated as PHA) and also to a method for manufacturing PHA very efficiently using a microorganism having capability to produce the PHA and accumulate it in bacterial bodies.

In addition, the present invention relates to a method for producing PHA using a substituted alkane derivative as a raw material.

2. Related Background Art

It has been reported so for that a variety of microorganisms produce poly-3-hydroxybutyric acid (hereinafter, sometimes abbreviated as PHB) and other PHAs and accumulate them in bacterial bodies. ("Handbook of Biodegradable Plastic", edited by Research Association of Biodegradable Plastic, NTS Co., Ltd., pp.178–197). These polymers as well as conventional plastics can be utilized for production of various products by melt processing or the like. Further, the polymers are biodegradable, and therefore they have an advantage of being completely degraded by microorganisms in nature, and causing no pollution by being left in natural environment unlike many conventional synthetic polymer compounds. Further, they are also excellent in biocompatibility and expected to be applied to a medical soft member or the like.

It has been known that such PHA produced by a microorganism may have a variety of compositions and structures depending on types of microorganism, culture medium composition, culture conditions and the like, and mainly from the viewpoint of improving physical properties of PHA, the study has been performed so far for controlling such composition and structure.

<<1>>First, the biosynthesis of PHAs which are obtained by polymerizing monomer units with a relatively simple structure such as 3-hydroxybutyric acid (hereinafter, sometimes abbreviated as 3HB) includes the followings.

For example, it is reported that *Alcaligenes eutropus* H16 strain (ATCC No. 17699) and its variants produce copolymers of 3-hydroxybutyric acid and 3-hydroxyvaleric acid in various composition ratios with a carbon source varied in their culturing (U.S. Pat. Nos. 4,393,167 and 4,876,331).

In U.S. Pat. No. 5,200,332, a method for producing copolymers of 3-hydroxybutyric acid and 3-hydroxyvaleric acid by making a microorganism of Methylobacterium sp., Paracoccus sp., Alcaligenes sp., or Pseudomonas sp. contact a primary alcohol having 3 to 7 carbons is disclosed.

In U.S. Pat. No. 5,292,860 and Japanese Patent Application Laid-Open No. 7-265065, it is disclosed that a two-component copolymer of 3-hydroxybutyric acid and 3-hydroxyhexanoic acid is produced by culturing *Aeromonas caviae* using oleic acid and olive oil as carbon sources.

In Japanese Patent Application Laid-Open No. 9-191893, it is disclosed that a polyester having monomer units of 3-hydroxybutyric acid and 4-hydroxybutyric acid is produced by culturing *Comamonas acidovorans* IFO 13852 strain using gluconic acid and 1,4-butanediol as carbon sources.

Recently, studies on a PHA comprising a 3-hydroxyalkanoic acid having medium-chain-length (abbreviated as mcl) wherein the number of carbons is up to about 12 have been carried out energetically. The synthetic route of such PHAs can be roughly classified into two parts, specifically examples of which will be shown in the following (1) and (2).

(1) Synthesis Using β-Oxidation:

In U.S. Pat. No. 5,135,859, it is disclosed that a PHA having a monomer unit of 3-hydroxyalkanoic acid having 6 to 12 carbons is produced by supplying an acyclic aliphatic hydrocarbon as a carbon source to *Pseudomonas oleovorans* ATCC 29347 strain. In Appl. Environ Microbiol, 58 (2), 746 (1992), it is reported that *Pseudomonas resinovorans* produces a polyester with monomer units of 3-hydroxybutyric acid, 3-hydroxyhexanoic acid, 3-hydroxyoctanoic acid and 3-hydroxydecanoic acid (the amount ratio: 1:15:75:9) using octanoic acid as a sole carbon source, and further a polyester with monomer units of 3-hydroxybutyric acid, 3-hydroxyhexanoic acid, 3-hydroxyoctanoic acid and 3-hydroxydecanoic acid (the amount ratio: 8:62:23:7) using hexanoic acid as a sole carbon source. Herein, it is considered that a monomer unit of a 3-hydroxyalkanoic acid having longer chain than that of a fatty acid as a material passes through the synthetic route of the fatty acid described in (2).

(2) Synthesis Using Fatty Acid De Novo Biosynthesis

In Int. J. Biol. Macromol., 16 (3), 119 (1994), it is reported that Pseudomonas sp. 61-3 strain produces a polyester with monomer units of 3-hydroxyalkanoic acids such as 3-hydroxybutyric acid, 3-hydroxyhexanoic acid, 3-hydroxyoctanoic acid, 3-hydroxydecanoic acid and 3-hydroxydodecanoic acid, and of 3-hydroxyalkenic acids such as 3-hydroxy-5-cis-decenic acid and 3-hydroxy-5-cis-dodecenic acid using sodium gluconate as a sole carbon source.

By the way, the biosynthesis of PHA is usually performed by PHA synthase using "D-3-hydroxyacyl-CoA" as a substrate which is generated as an intermediate of various metabolic pathways in the cells.

Herein, "CoA" means "coenzyme A". As described in the prior art of the above (1), when using a fatty acid such as octanoic acid, nonanoic acid or the like as a carbon source, it is said that the biosynthesis of PHA is carried out using "D-3-hydroxyacyl-CoA" as a starting material which is generated during the "β-oxidation pathway".

The reactions until PHA is biosynthesized through "β-oxidation pathway" are shown below.

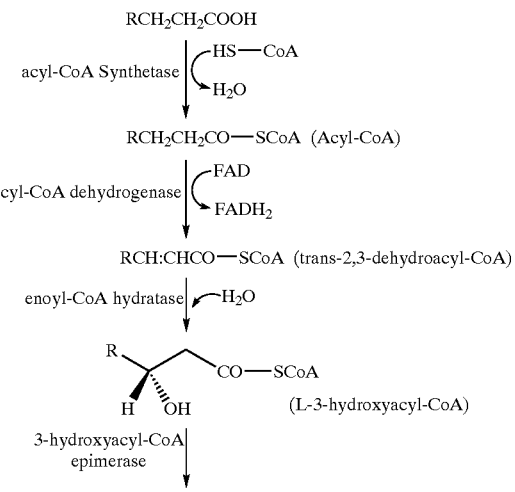

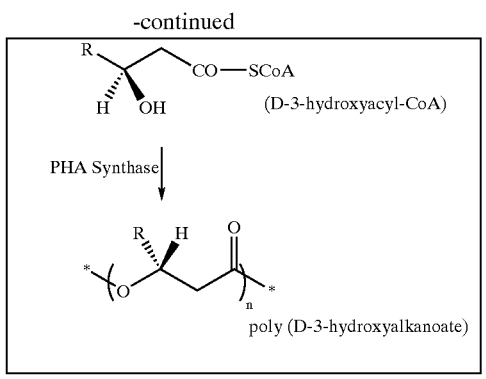

poly (D-3-hydroxyalkanoate)

On the other hand, as described in the prior art of the above described (2), when PHA is biosynthesized using saccharides such as glucose or the like, it is said that the biosynthesis is carried out using "D-3-hydroxyacyl-CoA" as a starting material converted from "D-3-hydroxyacyl-ACP" which is generated in the "fatty acid de novo biosynthesis"

Herein, "ACP" means "acyl carrier protein".

By the way, any of PHAs synthesized in the above (1) and (2) as described above is PHA which comprises monomer units having an alkyl group in the side chain, i.e. "usual PHA".

<<2>>However, when considering application of such PHAs produced by a microorganism to a wider range, e.g. as a functional polymer, PHAs ("unusual PHAs") In which substituents other then an alkyl group are introduced into the side chain are expected to be extremely useful. Examples of the substituent include those containing an aromatic ring (such as a phenyl group, a phenoxy group, a bennzoyl group or the like), an unsaturated hydrocarbon, an ester group, an aryl group, a cyano group, a halogenated hydrocarbon, an epoxide or the like. Of them, PHAs having an aromatic ring have been studied extensively.

(a) Those Containing a Phenyl Group or its Partially Substituted Form

In Makromol. Chem., 191, 1957–1965 (1990) and Macromolecules, 24, 5256–5260 (1991), it is reported that *Pseudomonas oleovorans* produces PHA containing 3-hydroxy-5-phenylvaleric acid as a unit using 5-phenylvaleric acid as a substrate.

Specifically, it is reported that *Pseudomonas oleovorans* produces 160 mg (31.64 of the dry weight to the bacterial body) per liter of a culture solution of a PHA comprising 3-hydroxyvaleric acid, 3-hydroxyheptanoic acid, 3-hydroxynonanoic acid, 3-hydroxyundecanoic acid and 3-hydroxy-5-phenylvaleric acid in a ratio of 0.6:16.0:41.1:1.7:40.6 as monomer units using 5-phenylvaleric acid and nonanoic acid as substrates (molar ratio of 2:1, total concentration of 10 mmol/L), and also this produces 200 mg (39.2% of the dry weight to the bacterial body) per liter of a culture solution of PHA containing 3-hydroxyhexanoic acid, 3-hydroxyoctanoic acid, 3-hydroxydecanoic acid and 3-hydroxy-5-phenylvaleric acid in a ratio of 7.3:64.5:3.9:24.3 as monomer units using 5-phenylvaleric acid and octanoic acid as substrates (molar ratio of 1:1, total concentration of 10 mmol/L). It is considered that the PHAs in this report is synthesized mainly through the β-oxidation pathway because nonanoic acid and octanoic acid are used.

The relating description is in Chirality, 3, 492–494 (1991) besides the above where change in the physical properties of the polymer is recognized which is presumably caused by containing a 3-hydroxy-5-phenylvaleric acid unit.

In Macromolecules, 29, 1762–1766 (1996), it is reported that *Pseudomonas oleovorans* produces a PHA containing 3-hydroxy-5-(4'-tolyl)valeric acid as a unit using 5-(4'-tolyl) valeric acid as a substrate.

In Macromolecules, 32, 2889–2895 (1999), it is reported that *Pseudomonas oleovorans* produces a PHA containing 3-hydroxy-5-(2', 4'-dinitrophenyl)valeric acid and 3-hydroxy-5-(4'-nitrophenyl)valeric acid as units using 5-(2',4'-dinitrophenyl)valeric acid as a substrate.

(b) Those Containing a Phenoxy Group or the Partially Substituted Form

In Macromol. Chem. Phys., 195, 1665–1672 (1994), it is reported that *Pseudomonas oleovorans* produces a PHA copolymer of 3-hydroxy-5-phenoxyvaleric acid and 3-hydroxy-9-phenoxynonanoic acid using 11-phenoxyundecanoic acid as a substrate.

Also in Macromolecules, 29, 3432–3435 (1996), it is reported that using *Pseudomonas oleovorans*, a PHA comprising 3-hydroxy-4-phenoxybutyric acid and 3-hydroxy-6-phenoxyhexanoic acid as units is produced from 6-phenoxyhexanoic acid, a PHA comprising 3-hydroxy-4-phenoxybutyric acid, 3-hydroxy-6-phenoxyhexanoic acid and 3-hydroxy-8-phenoxyoctanoic acid as units is produced from 8-phenoxyoctanoic acid, and a PHA comprising 3-hydroxy-5-phenoxyvaleric acid and 3-hydroxy-7-phenoxyheptanoic acid an units is produced from 11-phenoxyundecanoic acid. Some of polymer yields in this report are excepted as follows.

TABLE 1

| Carbon source (alkanoate) | Dry cell weight (mg/L) | Dry polymer weight (mg/L) | Yield (%) |
|---|---|---|---|
| 6-Phenoxyhexanoic acid | 950 | 100 | 10.5 |
| 8-Phenoxyoctanoic acid | 820 | 90 | 11 |
| 11-Phenoxyundecanoic acid | 150 | 15 | 10 |

In Japanese Patent Publication No. 2969175, a homopolymer comprising a 3-hydroxy-5-(monofluorophenoxy) pentanoate (3H5(MFP)P) unit or a 3-hydroxy-5-(difluorophenoxy)pentanoate (3H5(DFP)P) unit, a copolymer comprising at least 3H5(MFP)P unit or 3H5 (DFP)P unit, *Pseudomonas putida* capable of synthesizing these polymers, and the invention relating to a method for manufacturing the above described polymers where *Pseudomonas genus* is used is disclosed.

These production is performed by the following "two-step culture".

Culture time: 24 hours for the 1st step; and 96 hours for the 2nd step.

The substrates and polymers obtained in each step are shown as follows.

(1) Polymer obtained: 3-hydroxy-5-(monofluorophenoxy)pentanoate homopolymer

Substrate in the 1st step: citric acid, yeast extract

Substrate in the 2nd step: monofluorophenoxyundecanoic acid (2) Polymer obtained: 3-hydroxy-5-(difluorophenoxy) pentanoate homopolymer Substrate in the 1st step: citric acid, yeast extract Substrate in the 2nd step: difluorophenoxyundecanoic acid (3) Polymer obtained: 3-hydroxy-5-(monofluorophenoxy)pentanoate copolymer Substrate in the 1st step: octanoic acid or nonanoic acid, yeast extract Substrate in the 2nd step: monofluorophenoxyundecanoic acid (4) Polymer obtained 3-hydroxy-5-(difluorophenoxy) pentanoate copolymer Substrate in the 1st step: octanoic acid or nonanoic acid, yeast extract Substrate in the 2nd step: difluorophenoxyundecanoic acid.

It is said that as the effect, the polymer having a phenoxy group substituted with one or two fluorine atoms at the end of side chain can be synthesized by assimilating a medium chain fatty acid having a substituent and the stereoregularity and water repellency can be provided while keeping good workability with a high melting point.

Compounds substituted with cyano and nitro groups other than such forms substituted with such a fluoro group have also been studied.

In Can J. Microbiol., 41, 32–43 (1995) and Polymer International, 39, 205–213 (1996), it is reported that using *Pseudomonas oleovorans* ATCC 29347 strain and *Pseudomonas putida* KT 2442 strain, PHA comprising 3-hydroxy-p-cyanophenoxyhexanoic acid or 3-hydroxy-p-nitrophenoxyhexanoic acid as a monomer unit is produced using octanoic acid and p-cyanophenoxyhexanoic acid or p-nitrophenoxyhexanoic acid as substrates.

In these reports, since any polymer has an aromatic ring at the side chain of PHA which is different from general PHA having an alkyl group at the side chain, it will be advantageous to obtain polymers having the physical properties originated in them.

(c) PHA containing a cyclohexyl group in the monomer unit is expected to exhibit the physical properties of the macromolecule which is different from that of PHAs comprising usual aliphatic hydroxyalkanoic acid as units, and an example of the production by *Pseudomonas oleovorans* is reported (Macromolecules, 30, 1611–1615 (1997)).

According to this report, *Pseudomonas oleovorans* is cultivated in the culture medium wherein nonanoic acid and cyclohexylbutyric acid or cyclohexylvaleric acid coexist, and the resulting PHA comprises a unit containing a cyclohexyl group and a unit originated from nonanoic acid (each ratio is unknown).

For the yield etc., it is reported that the results shown in Table 2 were obtained by varying the ratio of cyclohexylbutyric acid and nonanoic acid in the condition of 20 mmol/L of the substrate concentration in total to cyclohexylbutyric acid.

TABLE 2

| Nonanoic acid: cyclohexylbutyric acid | CDW | PDW | Yield | Unit |
|---|---|---|---|---|
| 5:5 | 756.0 | 89.1 | 11.8 | Nonanoic acid, cyclohexylbutyric acid |
| 1:9 | 132.8 | 19.3 | 14.5 | Nonanoic acid, cyclohexylbutyric acid |

CDW: dry cell weight (mg/L), PDW: dry polymer weight (mg/L), Yield: PDW/CDW (%).

However, this example shows that the yield of the polymer per culture solution is insufficient, and also that the PHA itself obtained is mixed will the aliphatic hydroxyalkanoic acid originated in nonanoic acid in the monomer unit.

<<3>>Further, as a new category, the study is performed not only on the change of the physical properties but also for producing PHA having an appropriate functional group on the side chain to create a new function utilizing the functional group.

For example, in Macromolecules, 31, 1480–1486 (1996) and Journal of Polymer Science: Part A: Polymer Chemistry, 36, 2381–2387 (1998), etc., it is reported that PHA comprising a unit having a vinyl group at the end of the side chain was synthesized, then epoxidated with an oxidizing agent resulting in the synthesis of PHA containing a highly reactive epoxy group at the end of the side chain.

Further, as a synthetic example of PHA comprising a unit which has a sulfide expected to be highly reactive others than the vinyl group, it is reported in Macromolecules, 32, 8315–8318 (1999) that *Pseudomonas putida* 27N01 strain produces a PHA copolymer of 3-hydroxy-5-(phenylsulfanyl)valeric acid and 3-hydroxy-7-(phenylsulfanyl)heptanoic acid using 11-phenylsulfanylvaleric acid as a substrate.

As described above, while different compositions and structures of PHAs produced by microorganisms are obtained by varying types of microorganisms and composition of the culture medium, conditions of the culture and the like used for their production, it is not said yet to be sufficient for the physical properties when considering application as plastic. In order to further increase the use extent of the PHA produced by microorganisms, it is important to examine improvement of the physical properties more widely, and therefore it is essential to develop and explore PHAs comprising monomer units having further various structures and their manufacturing methods and microorganisms which can produce the desired PHA efficiently.

Moreover, in a typical producing method of PHA consisting of giving a microorganism a chemically synthesized substituted fatty acid as a substrate, there are many cases where a significant limitation on a chemical synthesis is imposed depending on the type, number, position and the like of a substituent to be introduced, since the carboxyl group of the substituted fatty acid is an active group in a chemical reaction, or because of the active group, complex handling such as protection and deprotection of the carboxyl group in the reaction steps of the chemical synthesis is required, and chemical reactions over several steps in the process are often required. Therefore, there was difficulty of the synthesis on an industrially producing level or requirement for much time, troubles and costs for the synthesis.

On the other hand, if "unusual PHA" can be produced using a substituted alkane, which is more easily synthesized chemically than substituted fatty acid, as a material, it is assumed that the above problems could be solved.

For production of PHA from alkane derivatives which have been reported so far, there are only examples that the corresponding PHAs were biosynthesized by microorganisms using straight chain alkanes and alkenes (alkanes containing double bonds) (Appl. Environ. Microbiol., 54, 2924–2932 (1988)), chlorine-substituted alkanes (Macromolecules, 23, 3705–3707 (1990)), fluorine-substituted alkanes (Biotechnol. Lett., 16, 501–506 (1994)) and alkanes containing acetoxy residues (Macromolecules, 33, 6571–8575 (2000)) as starting materials, whereas there are no synthetic examples of the corresponding PHAs from an alkane having a residue containing an aromatic ring as a substituent reported.

SUMMARY OF THE INVENTION

Therefore, the present inventors have studied assiduously on exploration of microorganisms having capability of producing different PHAs and accumulating them in the bacterial body and on a producing method of desired PHAs using such microorganisms, aiming at development of PHAs having a functional group at the side chain useful for a device material, a medical material and the like. Consequently, there was found a microorganism capable of producing a novel PHA comprising a 3-hydroxy-substituted benzoylalkanoic acid unit represented by the chemical formula [8]:

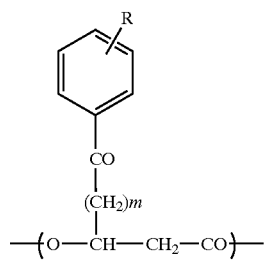

[8]

wherein m is at least one or more selected from the group consisting of n, n-2, n-4 and n-6 and one or more of integers: n is any integer of 1 to 8 corresponding to n in the following chemical formula [7]; and R is any one selected from the group consisting of a halogen atom, —CN, —NO$_2$, —CH$_3$, —C$_2$H$_5$, —C$_3$H$_7$, —CF$_3$, —C$_2$F$_5$ and —C$_2$F$_7$ corresponding to R in chemical formula [7], using a substituted benzoylalkanoic acid represented by chemical formula [7] as a material:

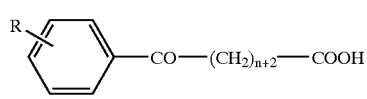

[7]

wherein n is any integer of 1 to 8; and R is any one selected from the group consisting of a halogen atom, —CN, —NO$_2$, —CH$_3$, —C$_2$H$_5$, —C$_3$H$_7$, —CF$_3$, —C$_2$F$_5$ and —C$_3$F$_7$, and of accumulating it in the bacterial body. It was further found that the PHA can be biosynthesized by culturing the microorganism under coexistence of the substituted benzoylalkanoic acid represented by the above chemical formula [7] with saccharides, an organic acid involved in the TCA cycle, yeast extract or polypeptone, and that the resulting PHA has relatively high purity. Specifically, for example, there was found a microorganism capable of producing a novel PHA comprising a 3-hydroxy-substituted benzoylvaleric acid unit represented by the chemical formula [5]:

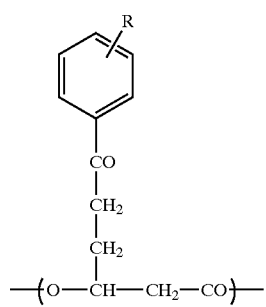

[5]

wherein R is any one selected from the group consisting of a halogen atom, —CN, —NO$_2$, —CH$_3$, —C$_2$H$_5$, —C$_3$H$_7$, —CF$_3$, —C$_2$F$_5$ and —C$_3$F$_7$ corresponding to R in the following chemical formula [9], using a substituted benzoylvaleric acid represented by chemical formula [9] as a material:

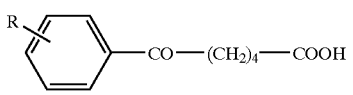

[9]

wherein R is any one selected from the group consisting of a halogen atom, —CN, —NO$_2$, —CH$_3$, —C$_2$H$_5$, —C$_3$H$_7$, —CF$_3$, —C$_2$F$_5$ and —C$_3$F$_7$, and capable of accumulating it in the bacterial body. It was further found that the PHA can be biosynthesized by culturing the microorganisms under coexistence of the substituted benzoylvaleric acid represented by the above chemical formula [9] with saccharides, an organic acid involved in the TCA cycle, yeast extract or polypeptone, and that the resulting PHA has relatively high purity. More specifically, for example, there was found a microorganism capable of producing a novel PHA comprising a 3-hydroxy-5-(4-fluorobenzoyl)valeric acid unit (hereinafter, sometimes abbreviated as 3HFBzV) represented by chemical formula [6]:

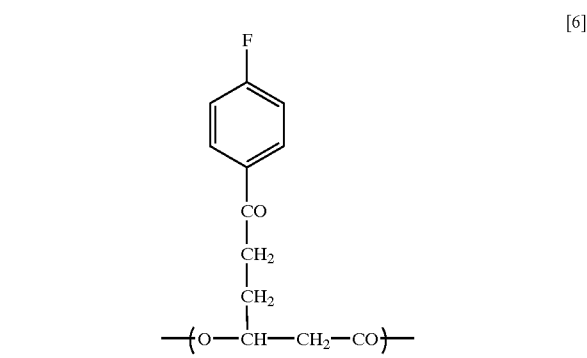

[6]

using 5-(4-fluorobenzoyl)valeric acid (hereinafter, abbreviated as FBzVA) represented by chemical formula [10] as a material:

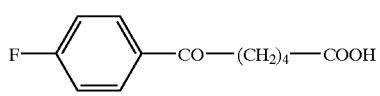

[10]

and capable of accumulating it in the bacterial body. It was further found that the PHA can be biosynthesized by culturing the microorganisms under coexistence of the substituted benzoylalkanoic acid with saccharides, an organic acid involved in the TCA cycle, yeast extract or polypeptone, and that the resulting PHA has relatively high purity, attaining the present invention.

That is, the present invention relates to PHAs comprising a 3-hydroxy-substituted benzoylalkanoic acid unit as a monomer unit represented by the chemical formula [2]:

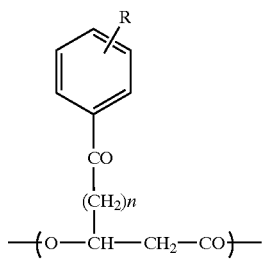

[2]

wherein n is any integer of 1 to 8: and R is any one selected from the group consisting of a halogen atom, —CN, —NO$_2$, —CH$_3$, —C$_2$H$_5$, —C$_3$H$_7$, —CF$_3$, —C$_2$F$_5$ and —C$_3$F$_7$.

Further, the present invention relates to a manufacturing method of a PHA comprising the steps of culturing a microorganism in a culture medium containing a substituted benzoylalkanoic acid represented by the chemical formula [7]:

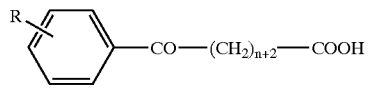

[7]

wherein n is any integer of 1 to 8; and R is any one selected from the group consisting of a halogen atom, —CN, —NO$_2$, —CH$_3$, —C$_2$H$_5$, —C$_3$H$_7$, —C$_3$, —C$_2$F$_5$ and —C$_3$F$_7$, and making the microorganisms to produce the PHA comprising the corresponding 3-hydroxy-substituted benzoylalkanoic acid unit represented as the following chemical formula [8]:

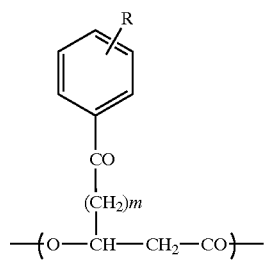

[8]

wherein m is at least one or more selected from the group consisting of n, n-2, n-4 and n-6 and one or more of integers; n is any integer of 1 to 8 corresponding to n in the above chemical formula [7]; and R is any one selected from the group consisting of a halogen atom, —CN, —NO$_2$, —CH$_3$, —C$_2$H$_5$, —C$_3$H$_7$, —CF$_3$, —C$_2$F$_5$ and —C$_3$F$_7$ corresponding to R in chemical formula [7].

That is, a method for manufacturing PHA of the present invention comprises the step of culturing a microorganism which produces PHA comprising a 3-hydroxy-substituted benzoylalkanoic acid unit under coexistence of the substituted benzoylalkanoic acid with saccharides, an organic acid involved in the TCA cycle, yeast extract or polypeptone.

Therefore, as a result of the fact that the present inventors have examined assiduously so as to develop a producing method of "unusual PHA" using a material easier to synthesize or more readily available than substituted fatty acids, it was found that production of the "unusual PHA" is feasible using substituted alkanes as materials easier to be chemically synthesized compared with the substituted fatty acids, attaining an invention of a method for manufacturing new PHAs using the present method.

Moreover, the present invention provides a new manufacturing method of "unusual PHA".

That is, the present invention is a manufacturing method of polyhydroxyalkanoates characterized by comprising the steps of using at least one starting compound selected from the group of substituted alkanes represented by the following general formula (13):

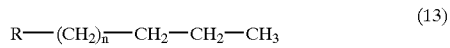

(13)

wherein R is a residue containing a substituted aromatic ring; n is an optional integer selected from 0 to 9, and of producing the polyhydroxyalkanoates comprising at least one selected from the group of 3-hydroxy-substituted alkanoate units represented by the following general formula in the molecules,

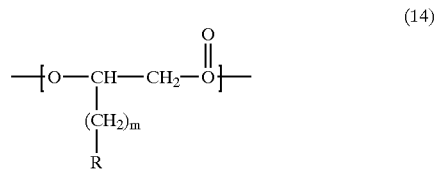

(14)

wherein R is a residue containing a substituted aromatic ring; m is any integer selected from 0 to 9.

More specifically, the manufacturing method of polyhydroxyalkanoates is characterized in that R in general formulas (13) and (14), i.e. the residue containing a substituted aromatic ring is a substituted phenyl residue group represented by the general formula (15):

(15)

wherein R$_1$ represents a substituent on an aromatic ring and is at least one selected from an H atom, a CN group, an NO$_2$ group, a halogen atom, CH$_3$ group, C$_2$H$_5$ group, C$_3$H$_7$ group, a CH$_2$=CH group, CF$_3$ group, C$_2$F$_5$ group and C$_3$F$_7$ group), a substituted phenoxy residue group represented by the general formula (16):

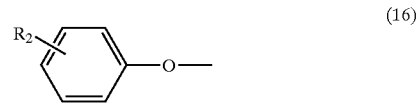

(16)

wherein R$_2$ represents a substituent on an aromatic ring and is at least one selected from an H atom, a CN group, an NO$_2$ group, a halogen atom, CH$_3$ group, C$_2$H$_5$ group, C$_3$H$_7$ group, CF$_3$ group, C$_2$F$_5$ group and C$_3$ F$_7$ group, and a substituted benzoyl residue group represented by the general formula (17):

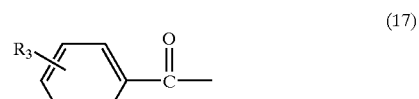

(17)

wherein R$_3$ represents a substituent on an aromatic ring and is at least one selected from an H atom, a CN group, an NO$_2$group, a halogen atom, CH$_3$ group, C$_2$H$_5$ group, C$_3$H$_7$ group, CF$_3$ group, C$_2$F$_5$ group and C$_3$F$_7$ group).

The producing process of the present invention is carried out using at least one selected from a group of substituted alkanes represented by the general formula (13) as a starting compound in the presence of the microorganism capable of producing polyhydroxyalkanoate which contains at least one selected from a group of 3-hydroxy-substituted alkanoate units represented by the general formula (14) in the molecule.

DETAILED DESCRIPTION OF THE PREFERRED EMBODIMENT

Figure 1:
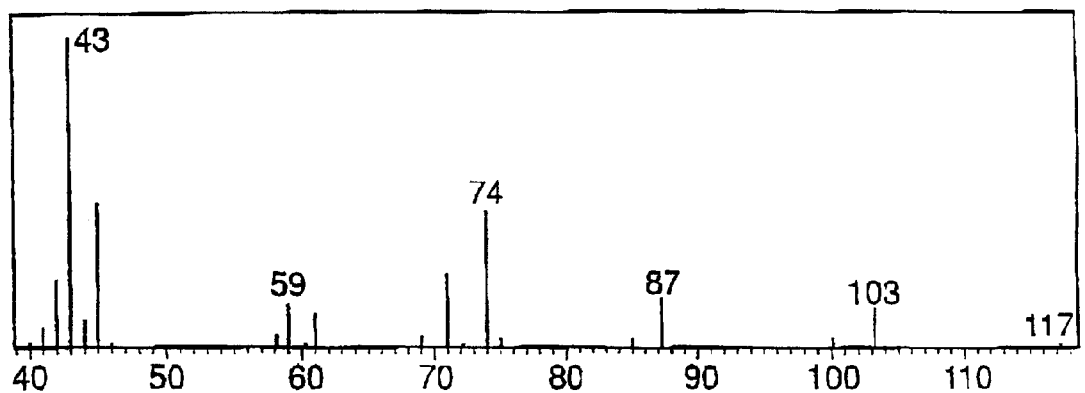
FIG. 1 shows a mass spectrum of methyl 3-hydroxybutyrate when PHA obtained in the system with 1.1% amylbenzene added in Example 8 was measured by GC-MS after methanolysis treatment.

PHAs of the present invention are those which comprise monomer units with various structures having substituents useful as a device material, a water repellent material, a medical material and so on at the side chain, more specifically, PHAs which have a substituted benzoyl group at the side chain. Further, the methods for manufacturing PHAs of the present invention enable manufacturing desired PHAs with high purity in a high yield by use of microorganisms. In addition, PHAs of the present invention are isotactic polymers typically composed of only R-configuration.

<Saccharides and Organic Acids Involved in TCA Cycle: Difference from Prior Arts>

One of the methods for manufacturing PHAs of the present invention is characterized in that the content rate of intended monomer units is markedly increased or only the intended monomer units exist in PHAs produced/accumulated by microorganisms by adding sacharides or organic acids involved in the TCA cycle as a carbon source besides the alkanoic acid in addition to the alkanoic acid for introducing desired monomer units into the medium when culturing the microorganisms. This promoting effect of prioritizing the specific monomer unit is obtained by addition of only sacharides or organic acids involved in the TCA cycle as a carbon source besides the alkanoic acid to the medium.

In other words, the inventors obtained findings that; when sacharides or organic acids involved in the TCA cycle are cultivated as substrates coexisting with an alkanoic acid for introducing desired monomer units, intended PHAs are obtained in much higher yields with much higher purity than those obtained by conventional methods where mcl-alkanoic acids such as nonanoic acid or octanoic acid are used as a coexisting substrate; and that such effect is obtained by the fact that this culture method is capable of generating acetyl CoA which is a carbon source and an energy source of microorganisms through the method not depending on β-oxidation, and attained the present invention.

In the methods of the present invention, saccharide compounds, e.g. glucose, fluctose, mannose and the like will be used as a substrate for growth of microorganisms and a PHA produced is composed of an alkanoate for introduction of the desired monomer units coexisting with the saccharides contains no monomer units originated in the saccharides such as glucose or contain only extremely a small amount. In such a point, the methods of the present invention are basically different in both composition and effect from the conventional PHA producing methods by microorganism using saccharides themselves such as glucose as a material substrate of a monomer unit to be introduced into the PHA.

<Yeast Extract: Difference from Conventional Arts>

One of the methods for manufacturing PHAs of the present invention is characterized in that the content rate of intended monomer units is markedly increased or only the intended monomer units exist in PHAs produced/accumulated by microorganisms by adding only yeast extract as a carbon source besides the alkanoic acid in addition to the alkanoic acid for introducing desired monomer units into the medium when culturing the microorganisms. This promoting effect of prioritizing the specific monomer unit is obtained by addition of only yeast extract as a carbon source besides the alkanoic acid to the medium.

Examples of using yeast extract in the medium when producing PHAs by microorganisms include a method using microorganisms which belong to Rhodobacter sp. described in Japanese Patent Application Laid-Open No. 5-49487. This conventional method is, however, a producing method of usual PHBs with monomer units of a hydroxyalkanoate having no substituents and poly-3-hydroxyvaleric acid (hereinafter, sometimes abbreviated as PHV). It is known that the synthetic route of PHAs aimed at in the present invention is an independent route from the synthetic route producing PHB and PHV, and Japanese Patent Application Laid-Open No. 5-49487 did not refer to the effect of yeast extract in the synthetic route of PHAs aimed at in the present invention at all. Further, for the effect of yeast extract, it is indicated only that addition of yeast extract has a promoting effect on increasing accumulated amount of PHAs in the bacterial body, and it is specified that yeast extract is added not aiming at multiplication.

In the present invention, production/accumulation of PHA as well as multiplication is performed by making a substituted benzoylalkanoic acid coexist with yeast extract, the yeast extract showing a quite different effect. Further, the above inventions neither refer to the prioritization of a specified monomer unit at all which is an effect of the present invention nor show the effect of prioritization of the specified monomer unit which has a substituted benzoyl group as a substituent as the present invention does.

Further, examples in which yeast extract is used for production of PHAs by microorganisms include a method using *Pseudomonas putida* described in Japanese Patent Publication No. 2989175. The method of producing PHAs disclosed here is only that by 2-step culture and it is disclosed that accumulation of PHA is performed only in the 2nd step of culture under the limitation of nutrition sources except for a carbon source. In this point, the above described method is quite different in composition and effect from that of the present invention in which desired PHAs are synthesized/accumulated through only 1 step culture with the medium containing a substituted benzoylalkanoic acid and yeast extract.

Furthermore, the effect of yeast extract in Japanese Patent No. 2989175 aims at, in the 1st step of culture, only growth of the microorganisms to be used for the 2nd step of culture when using 2-step culture and it is specified that culture at the 1st step is performed under the conditions rich in nutrition sources. Herein, the substrate of PHA does not coexist at the 1st step, whereas the effect of yeast extract in the present invention is to carry out production/accumulation of PHA by making a substituted benzoylalkanoic acid coexist with yeast extract as well as multiplication, the yeast extract showing a quite different effect.

Furthermore, in Japanese Patent No. 2989175, any of citric acid, octanoic acid and nonanoic acid coexists as a carbon source at the 1st step of culture, therefore the above method is different also in composition from the present invention in which only a substituted benzoylalkanoic acid coexists with yeast extract.

<Polypeptone: Difference from Prior Arts>

One of the methods for manufacturing PHAs of the present invention is characterized in that the content rate of intended monomer units is markedly increased or only the intended monomer units exist in PHAs produced/accumulated by microorganisms by adding only polypeptone as a carbon source besides the alkanoic acid in addition to the alkanoic acid for introducing desired monomer units into the medium when culturing the microorganisms. This promoting effect of prioritizing the specific monomer unit is obtained by addition of only polypeptone as a carbon source besides the alkanoic acid to the medium.

For examples using polypeptone for PHA production by microorganisms, Japanese Patent Application Laid-Open No. 5-49487, Japanese Patent Application Laid-Open No. 5-64591, Japanese Patent Application Laid-Open No. 5-214081, Japanese Patent Application Laid-Open No. 6-145311, Japanese Patent Application Laid-Open No 6-284892, Japanese Patent Application Laid-Open No. 8-89264, Japanese Patent Application Laid-Open No. 9-191893, Japanese Patent Application Laid-Open No. 11-32789 and so on disclose that the medium is made to contain polypeptone when PHAs are produced by microorganisms, however, in any of the above described patents, polypeptone is used in the pre-culture step, i.e. it is used in only the step of proliferation of bacteria, and the substrate to be the monomer unit of PHA is not contained when pre-culturing. There are also no examples where polypeptone is used in the step of producing PHAs by bacteria.

In contrast, in the present invention, production and accumulation of PHAs are performed by making an alkanoic acid for introducing desired monomer units coexist with only polypeptone as a carbon source besides the present alkanoic acid as well as multiplication, the method is thus quite different in composition and effect from the conventional examples using polypeptone. Further, the above described patents neither refer to the prioritization of a specified monomer unit at all which is an effect of the present invention nor show the effect of prioritization of the specified monomer unit which has a substituted benzoyl group as a substituent.

The microorganisms and culturing steps and the like used in the present invention will be described as follows.

<System for Supplying PHA Monomer Unit>

First, "fatty acid de novo biosynthesis", one of systems supplying the mcl-3HA monomer unit which will be mixed into the targeting PHA will be described in detail.

When a saccharide such as glucose is used as a substrate, an alkanoic acid necessary as a cell component is biosynthesized through the "fatty acid de novo biosynthesis" with acetyl CoA as a starting material which is produced via "glycolysis system" from saccharides. The biosynthetic pathway of fatty acid includes the de novo synthetic pathway and carbon chain-elongating pathway which will be described as follows.

(1) De Novo Synthetic Pathway

This is catalyzed by two enzymes which are acetyl CoA carboxylase (EC 6.4.1.2) and synthetic enzyme of fatty acid (EC 2.3.1.85). The acetyl CoA carboxylase is an enzyme which finally catalyzes the following reaction mediated by biotin and generates malonyl CoA from acetyl CoA, and the reaction is represented as the following formula:

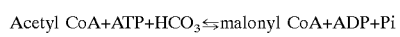

Acetyl CoA+ATP+HCO$_3^-$⇌malonyl CoA+ADP+Pi

The synthetic enzyme of fatty acid is an enzyme which catalyzes the reaction cycle of transition-condensation-reduction-dehydration-reduction, and the whole reactions are represented as the following formula:

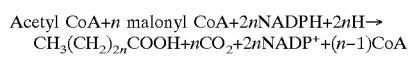

Acetyl CoA+$n$ malonyl CoA+2$n$NADPH+2$n$H→
CH$_3$(CH$_2$)$_{2n}$COOH+$n$CO$_2$+2$n$NADP$^+$+($n$−1)CoA In addition, reaction products will be free acids, CoA derivatives or ACP derivatives depending on the type of enzyme. Herein, the acetyl CoA is represented as the following chemical formula.

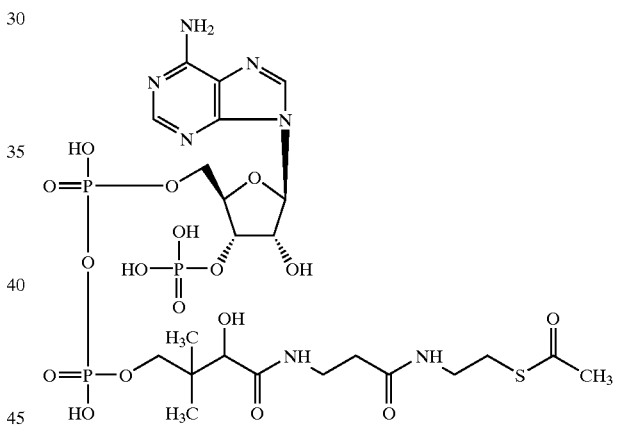

Methenyl CoA is represented by the following chemical formula.

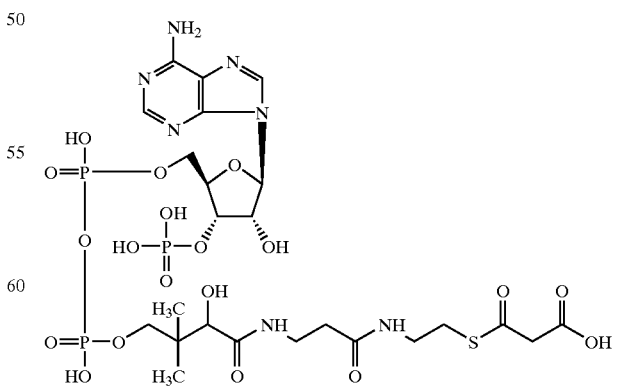

Herein, CoA is the abbreviated name for coenzyme A which is represented by the following chemical formula.

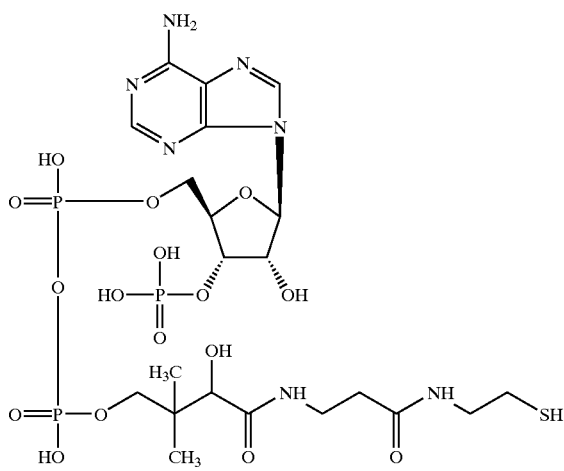

Of the present reaction pathways, "D-3-hydroxyacyl ACP" which will be a monomer substrate of PHA biosynthesis is supplied as an intermediate through the pathway as shown below. In addition, adding two carbons each through the pathway as shown in the following reaction scheme, finally it is extended to palmitic acid. Therefore, as a monomer substrate of the PHA biosynthesis, seven "D-3-hydroxyacyl ACPs" of "D-3-hydrobutyryl ACP" to "D-3-hydroxypalmityl ACP" will be supplied where the number of carbons is even.

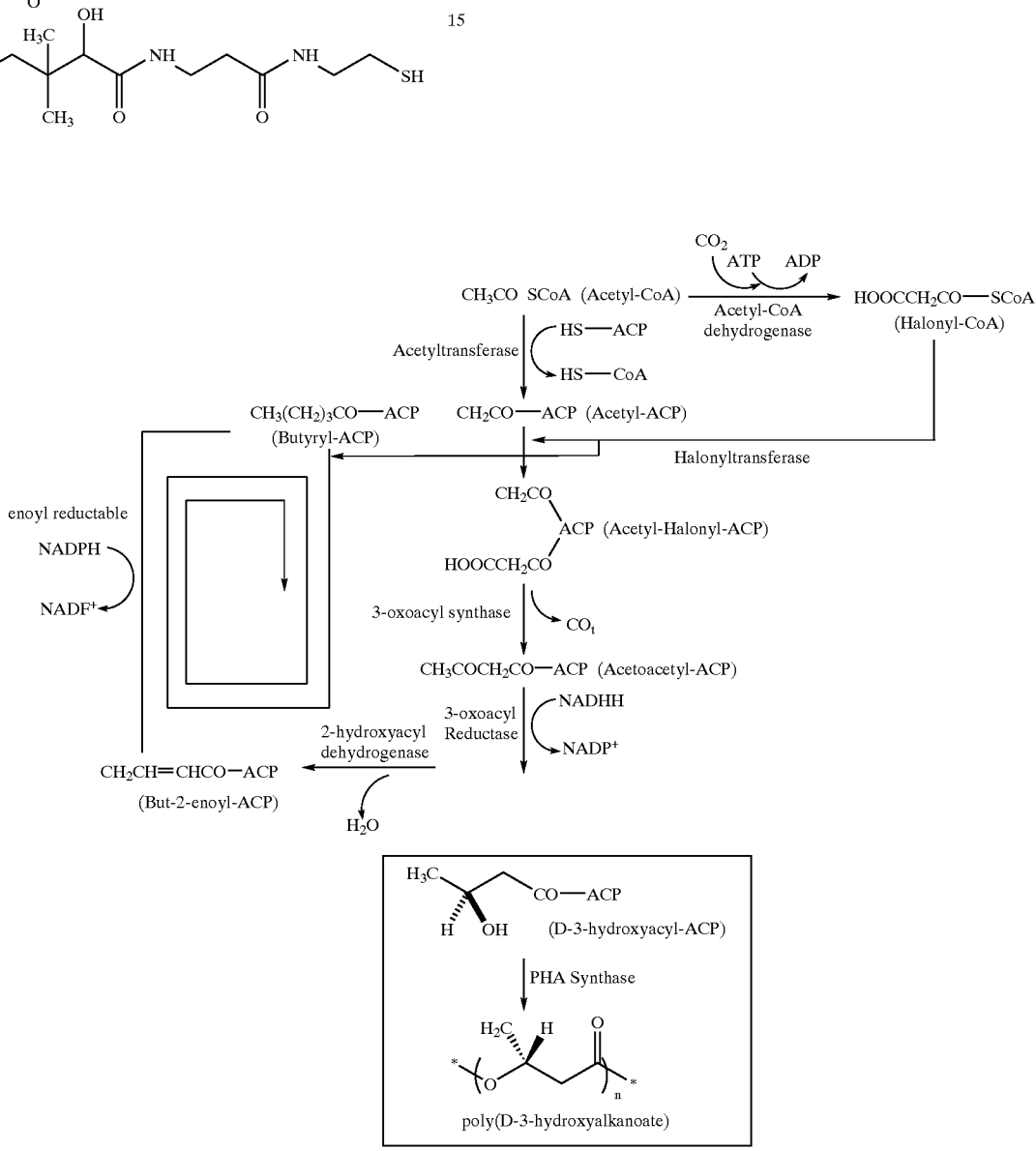

(2) Pathway of Carbon Chain Elongation

These pathways are roughly divided into two pathways including the pathway (designated as Pathway A) where malonyl ACP is added to acyl ACP finally becoming acyl ACP (and $CO_2$) elongated by two carbon chains and the pathway (designated as Pathway B) where acetyl CoA is added to acyl CoA finally becoming acyl CoA elongated by two carbon chains. Each pathway will be described as follows.

Pathway A

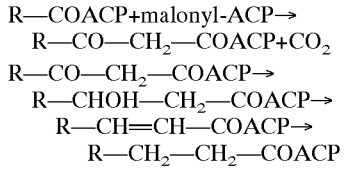

Pathway B

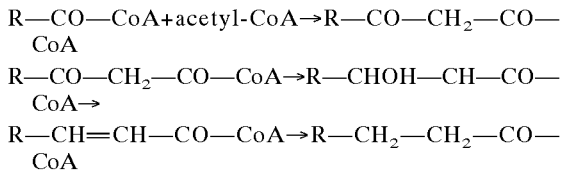

Both A and B pathways generate "D-3-hydroxyacyl CoA" or "D-3-hydroxyacyl ACP" as an intermediate, and it is considered that "D-3-hydroxyacyl CoA" itself is utilized as a monomer substrate of the PHA biosynthesis and "D-3-hydroxyacyl ACP" is utilized as a monomer substrate of the PHA biosynthesis after it is converted into "D-3-hydroxyacyl CoA" by ACP-CoA transferase.

When using saccharides such glucose as a substrate, it is considered that a mcl-3HA monomer unit is produced through "glycolysis system" and "biosynthetic pathway of fatty acid". Further, when using an organic acid involved in the TCA cycle as a substrate, the acetyl CoA is directly produced from pyruvic acid by pyruvate dehydrogenase. Phophoenolpyruvic acid is generated from oxaloacetic acid by phosphoenolpyruvate carboxynase which is then catalyzed by pyruvate kinase to generate pyruvic acid, further generating by acetyl CoA through the above reaction. It is considered that the acetyl CoA generated by these reactions produces the mcl-3HA monomer unit through "biosynthetic pathway of fatty acid".

Herein, it is considered that e.g. mcl-alkanoic acid such as octanoic acid and nonanoic acid or e.g. alkanoic acid in which a functional group other than a straight chain aliphatic alkyl is added at the end, e.g. 5-phenylvaleric acid, 4-phenoxybutyric acid 4-cyclohexylbutyric acid are converted into CoA derivatives by CoA ligase (EC 6.2.1.3 etc.) and directly into "D-3-hydroxyacyl CoA" which will be a monomer substrate of the PHA biosynthesis by an enzyme group carrying β-oxidation system.

In short, while a mcl-3HA monomer unit generated from saccharides or an organic acid involved in the TCA cycle is produced through extremely multi-step enzyme reactions (i.e. indirectly), the mcl-3HA monomer unit from mcl-alkanoic acid will be produced very directly.

Here, generation of acetyl CoA in charge of growth of microorganisms will be described. In a method where a mcl-alkanoic acid is made to coexist in addition to an alkanoic acid for introduction of an intended monomer unit, acetyl CoA is generated from these alkanoic acids through the β-oxidation system. Comparing with alkanoic acids having bulky substituents (alkanoic acids having substituents such as a phenyl group, a phenoxy group, a cyclohexyl group or the like), the mcl-alkanoic acid is generally considered to be excellent in substrate affinity to an enzyme group in the β-oxidation system, and the acetyl CoA is effectively produced by coexistence of the mcl-alkanoic acid. Therefore, this is advantageous for growth of microorganisms where the acetyl CoA is used as an energy source and a carbon source.

However, since the mcl-alkanoic acid through the β-oxidation system is directly converted into a PHA monomer unit, it is a big problem that the PHA produced comprises a large amount of a mcl-3HA monomer unit in addition to an intended monomer unit.

In order to solve this problem, a desirable method is that a substrate other then the mcl-alkanoic acid which may supply effectively acetyl CoA or an energy source and a carbon source is selected and made to coexist with an intended alkanoic acid. As aforementioned, while the acetyl CoA may be converted into a PHA monomer unit through the biosynthetic pathway of fatty acid, this is indirect and requires passing through more multi-step reactions comparing with the mcl-alkanoic acid by selecting appropriate culture conditions including concentration of the substrate which may generate acetyl CoA, a manufacturing method substantially without or with less mixing of mcl-3HA is feasible.

A manufacturing method where a microorganism is cultured aiming at only its growth in the first step and subsequently in the second step only an intended alkanoic acid as a carbon source is added into the culture medium is widely used. Herein, acyl CoA ligase which is an initiating enzyme in the β-oxidation system converting the alkanoic acid to the acyl CoA requires ATP, and according to the present inventors' investigation, by obtaining the results that a manufacturing method where a substrate which a microorganism can use as an energy is made to coexist also in the second step is more effective, the present invention was completed.

For a substrate which can supply effectively acetyl CoA or an energy source and a carbon source in the present inventive method, any compounds may be used including: aldoses such as glyceroaldehyde, erythrol, arabinose, xylose, glucose, galactose, mannose and fluctose; alditols such as glycerol, erythritol and xylitol; aldonic acids such as gluconic acid; uronic acids such as glucuronic acid and galacturonic acid; saccharides such as disaccharides e.g. maltose, sucrose and lactose; and organic acids involved in the TCA cycle such as lactic acid, pyruvic acid, malic acid, citric acid, succinic acid, fumaric acid, and their salts; further natural culture component such as yeast extract, polypeptone, meat extract, casamino acid and the like, if they can supply the acetyl CoA or the energy source and carbon source without passing through the β-oxidation system, and they can be suitably selected for usefulness as a substrate to a strain used. Further, if the combination has less mixture of mcl-3HA, it is possible to select plural compounds to be used.

<Microorganism>

Microorganisms used in the present invention, any of them may be used if they can produce PHA comprising the above described 3-hydroxy-substituted-benzoylalkanoic acid unit using the above described substituted benzoylalkaoic acid as a material. Further, in the scope of attaining the present inventive purposes, plural microorganisms may be mixed to be used if necessary.

Using FBzVA etc. as a substrate, the present inventors searched microorganisms which have capability of producing PHA containing the above described 3HFBzV etc. as a monomer unit and accumulating it in the bacterial body. Consequently, the present inventors have found that microorganisms, *Pseudomonas cichorii* H45 strain,

*Pseudomonas cichorii* YN2 strain, *Pseudomonas jessenii* P161 strain, etc. isolated from soil and having capability of producing PHA had the desired capability. Herein, these strains have been deposited in International Patent Organism Depositary of General Research Institute, Independent Administrative Corporation (former Patent Organism Deposit Center of Research Institute of Life Engineering, Ministry of Economy and Industry) as Deposit No. "FERM BP-7374" for the H45 strain, Deposit No. "FERM BP-7375" for the YN2 strain and Deposit No. "FERM BP-7376" for the P161 strain, respectively.

The bacteriological properties of the above described H45 strain, YN2 strain and P161 strain are listed as follows. In addition, for the P161 strain, the base sequence of 16sr RNA is shown in the sequence No. 1.

<Bacteriological Property of H45 Strain>
(1) Morphological Properties
Shape and size of cell; Bacillus, 0.8 μm×1.0–1.2 μm
Polymorphism of cell: absence
Mobility: presence
Spore formation: absence
Gram stainability: negative
Colony shape: round, all smooth rims, low convex, smooth surface layer, gloss and cream color
(2) Physiological Properties
Catalase: positive
Oxidase: positive
O/F test: oxidation type
Reduction of nitrate: negative
Production of indole: positive
Acidification of glucose: negative
Arginine dihydrolase: negative
Urease: negative
Hydrolysis of esculin: negative
Hydrolysis of gelatin: negative
β-Galactosidase: negative
Production of fluorochrome on King's B agar: positive
Growth in 4% NaCl: negative
Accumulation of poly-β-hydroxybutyric acid: negative
(3) Assimilability of Substrate
Glucose: positive
L-Arabinose: negative
D-Mannose: positive
D-Mannitol: positive
N-Acetyl-D-glucosamine: positive
Maltose: negative
Potassium gluconate; positive
n-Caprylic acid: positive
Adipic acid: negative
dl-Malic acid: positive
Sodium citrate: positive
Phenyl acetate: positive <Bacteriological Properties of YN2 Strain>
(1) Morphological Properties
Shape and size of cell: Bacillus, 0.8 μmn×1.5–2.0 μm
Polymorphism of cell: absence
Mobility: presence
Spore formation: absence
Gram stainability: negative
Colony shape: round, all smooth rims, low convex, smooth surface layer, gloss, cream color and translucent
(2) Physiological Properties
Catalase: positive
Oxidase: positive
O/F test: oxidation type
Reduction of nitrate: negative
Production of indole: positive
Acidification of glucose: negative
Arginine dihydrolase: negative
Urease: negative
Hydrolysis of esculin: negative
Hydrolysis of gelatin: negative
β-Galactosidase: negative
Production of fluorochrome on King's B agar: positive
Growth in 4% NaCl: positive (weak growth)
Accumulation of poly-β-hydroxybutyric acid: negative
Hydrolysis of Tween 80: positive
(3) Assimilability of Substrate
Glucose: positive
L-Arabinose; positive
D-Mannose: negative
D-Mannitol: negative
N-Acetyl-D-glucosamine: negative
Maltose: negative
Potassium gluconate: positive
n-Caprylic acid: positive
Adipic acid: negative
dl-Malic acid: positive
Sodium citrate: positive
Phenyl acetate: positive <Bacteriological Properties of P161>
(1) Morphological Properties
Shape and size of cell: sphere, φ 0.6 μm
Bacillus, 0.6 μm×1.5–2.0 μm
Polymorphism of cell: presence (elongation type)
Mobility: presence
Spore formation: absence
Gram stainability: negative
Colony shape: round, all smooth rims, low convex, smooth surface layer, gloss and pale yellow
(2) Physiological Properties
Catalase: positive
Oxidase: positive
O/F test: oxidation type
Reduction of nitrate: positive
Production of indole: negative
Acidification of glucose: negative
Arginine dihydrolase: positive
Urease: negative
Hydrolysis of esoulin: negative
Hydrolysis of gelatin: negative
β-Galactosidase: negative
Production of fluorochrome on King's B agar; positive
(3) Assimilability of Substrate
Glucose: positive
L-Arabinose: positive
D-Mannose: positive
D-Mannitol: positive
N-Acetyl-D-glucosamine: positive
Maltose: negative
Potassium gluconate: positive
n-Caprylic acid: positive
Adipic acid: negative
dl-Malic acid: positive
Sodium citrate: positive
Phenyl acetate: positive In addition to *Pseudomonas genus*, it is possible to use microorganisms which belong to Aeromonas sp. Comamonas sp or Burkholderia sp. and produce PHA comprising the above described 3-hydroxy-substituted benzoylalkanoic acid unit as a monomer unit using the above substituted benzoylalkanes as a material.

<Culture>
The intended PHA can be produced by culturing these microorganisms in a culture medium containing an alkanoic acid for introduction of a desired monomer unit and a substrate for growth of the present invention. Such a PHA is generally composed of only the R-configuration being an isotactic polymer.

For the usual culture of the microorganism used in the manufacturing method of PHA relating to the present invention, for example, preparation of stored strains and growth for retaining bacterial count and active condition required for production of PHA and be like, the culture medium containing components required for growth of microorganisms used is suitably selected to be used. For example, any types of culture medium such as the general natural one (meat extract, yeast extract or the like) or the synthetic one with nutrients added can be used so long as they do not have a bad influence on growth and survival of microorganisms.

Any culture methods such as liquid culture and solid culture may be used if they can multiply the microorganisms and produce PHA. Further, any types of culture can be used without regard to batch culture, fed batch culture, semi-continuous culture, continuous culture or the like. As a form of the liquid batch culture, there are methods of supplying oxygen by shaking using a shaking flask and by a stirring aeration method using a jar fermenter. A multi-step method in which a plurality of these steps are connected may be adopted.

When manufacturing PHAs comprising 3-hydroxy-substituted benzoylalkanoic acid units using PHA-producing microorganisms as described above, an inorganic medium etc. containing at least respective corresponding substituted benzoylalkanoic acids as materials for PHA production and a carbon source for growth of microorganisms can be used.

As the carbon source for growth, it is possible to use the medium components originated in natural products such as yeast extract, polypeptone, meat extract, casamino acid and the like, further any compounds such as saccharides, organic acids involved in the TLC cycle (organic acids generated as intermediates in the TCA cycle and those generated through one or two steps of biochemical reactions from the TCA cycle) or their salts or the like can be used if they generate acetyl CoA without passing through the β-oxidation cycle, and can be suitably selected for usefulness as a substrate to a used strain. In addition, it is possible to select plural compounds to be used if the combination has less mixture of mcl-3HA.

Of them, for sacharides, one or more compounds selected from aldoses such as glyceroaldehyde, erythrose, arabinose, xylose, glucose, galactose, mannose or fluctose; alditols such as glycerol, erythritol or xylitol; aldonic acids such as gluconic acid; uronic acids such as glucuronic acid or galacturonic acids disacoharides such as maltose, sucrose or lactose can be suitably used.

Examples of organic acids or their salts include pyruvic acid, oxaloacetic acid, citric acid, isocitric acid, ketoglutaric acid, succinic acid, fumaric acid, malic acid or lactic acid, or one or more compounds selected from their salts can be suitably used. Of them, particularly use of saccharides is preferable, particularly at least one selected from a group consisting of glucose, fluctose and mannose is more preferable.

For the method for producing/accumulating PHAs by microorganisms, the productivity sometimes improves when sufficient multiplication is performed first, then the bacteria are transferred into the medium with a limited nitrogen source such as ammonium chloride and further cultured in the state with a compound added as a substrate of an intended unit. Specifically, adoption of multi-step method in which a plurality of the above described steps are connected is included. For example, there is a method where culturing is performed in the inorganic medium etc. containing about 0.05% to 5.0% of D-glucose and about 0.01% to 1.0% of a substituted benzoylalkanoic acid from the logarithmic growth up to the stationary phase the bacteria are recovered by centrifugal separation etc., and further they are cultured in an inorganic medium containing about 0.01% to 1.0% of the substituted benzoylalkanoic acid with a limited nitrogen source or without its existence substantially.

For the inorganic medium used in the above culturing method, any types if they contain components such as a phosphorous source (e.g. phosphate etc.), a nitrogen source (e.g. ammonium salt, nitrate, etc.) and the like capable of growing microorganisms may be used, for example, the inorganic salt medium may include the MSB medium, E medium (J. Biol. Chem., 218, 97–106 (1956)), M9 medium and the like. Herein, composition of the M9 medium used in Examples of the present invention is as follows.

$Na_2HPO_4$: 6.2 g
$KH_2PO_4$: 3.0 g
NaCl: 0.5 g
$NH_4Cl$: 1.0 g
(in 1 liter of the medium, pH 7.0)

Further, in order to perform good growth and production of PHA, it is preferable to add about 0.3% (v/v) of a solution of the following trace components into the above inorganic salt medium.

Trace Component Solution
Nitrilotriacetic acid: 1.5 g
$MgSO_4$; 3.0 g
$MnSO_4$: 0.5 g
NaCl: 1.0 g
$FeSO_4$; 0.1 g
$CaCl_2$: 0.1 g
$CoCl_2$: 0.1 g
$ZnSO_4$; 0.1 g
$CuSO_4$: 0.1 g
$AlK(SO_4)_2$: 0.1 g
$H_3BO_3$: 0.1 g
$Na_2MoO_4$: 0.1 g
$NiCl_2$: 0.1 g
(in 1 litter)

For the culturing temperature any temperature may be used if it enables the above described strains to grow well for example, 15–40° C., preferably 20–35° C. and more preferably about 20–30° C. are appropriate.

As a specific example, culturing is performed in the inorganic medium etc. containing about 0.05% to 5.0% of D-glucose and about 0.01% to 1.0% of a substituted benzoylalkanoic acid, the bacterial bodies were at the time from the logarithmic growth phase up to the stationary phase, the desired PHA with less mixture of unintended monomer units or without them at all can be extracted. Such PHA is generally composed of only the R-configuration being isotactic polymer.

The same amount of an organic acid involved in the TCA cycle, yeast extract and polypeptone instead of D-glucose may be added and their combination may be used.

<Recovery of PHA>

For obtaining PHA from the culture solution relating to the present invention, the methods performed usually are applicable. When PHA is discharged in the culture solution, methods of extraction and purification from the culture solution are used and when PHA is accumulated it in the bacterial bodies, methods of extraction and purification from bacterial bodies are used. For recovery of PHA from the cultured bacterial body of microorganism, for example, while extraction with organic solvents such as chloroform performed usually is the simplest, dioxane, tetrahydrofuran, acetonitrile and acetone besides chloroform are sometimes used. In the circumstance difficult to use organic solvents, the following methods also can be used: the bacterial body components except PHA are removed by fracturing the microorganism cells physically using any methods of treatment with a surfactant such as SDS, treatment with an enzyme such as lysozyme, treatment with agents such as EDTA, hydrogen peroxide, sodium hypochlorite and ammonia, or the ultrasonic fracturing method, homogenizer method, pressure fracturing method, beads impact method, grinding method, mashing method and freeze-thaw method to recover PHA.

In addition, culturing of microorganisms by the present invention, production of PHAs and their accumulation into the bacterial body by microorganisms of the present invention and recovery of PHAs from the bacterial body of the present invention are not limited to the above described methods.

The second example of compounds used as starting materials in the present invention can include at least one selected from substituted phenylalkanes represented by the chemical formula (22), and polyhydroxyalkanoates manufactured in that case can include polyhydroxyalkanoates containing at least one selected from 3-hydroxy(substituted phenyl)alkanoate units represented by the chemical formula (23) in the molecule:

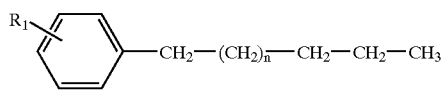

(22)

wherein $R_1$ shows a substituent on the aromatic ring and is at least one selected from an H atom, a CN group, an $NO_2$ group, a halogen atom, a $CH_3$ group, a $C_2H_5$ group, a $C_3H_7$ group, a $CH_2=CH$ group, a $CF_3$ group, a $C_2F_5$ group and a $C_3F_7$ group; and n is an optional integer selected from 0 to 9), and

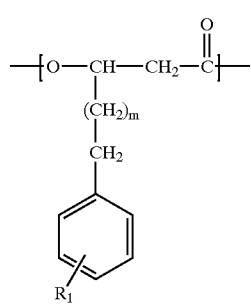

(23)

wherein $R_1$ shows a substituent on the aromatic ring and is at least one selected-from an H atom, a CN group, an $NO_2$ group, a halogen atom, a $CH_3$ group, a $C_2H_5$ group, a $C_3H_7$ group, a $CH_2=CH$ group, a $CF_3$ group, a $C_2F_5$ group and a $C_3F_7$ group; and m is an optional integer selected from 0 to 9.

The second example of compounds used as starting materials in the present invention can include at least one selected from substituted phenoxyalkanes represented by the chemical formula (24), polyhydroxyalkanoates manufactured in that case can include those containing at least one in the molecule selected from 3-hydroxy(substituted phenoxy)alkanoate units represented by the chemical formula (25):

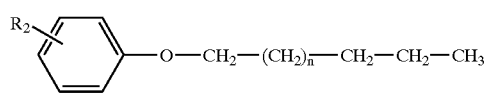

(24)

wherein $R_2$ shows a substituent on the aromatic ring and is at least one selected from an H atom, a CN group, an $NO_2$ group, a halogen atom, a $CH_3$ group, a $C_2H_5$ group, a $C_3H_7$ group, a $CF_3$ group, a $C_2F_5$ group and a $C_3F_7$ group; and n is an optional integer selected from 0 to 9, and

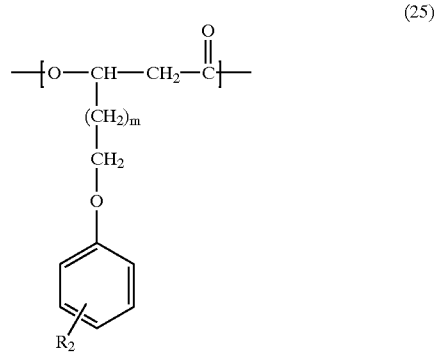

(25)

wherein $R_2$ shows a substituent on the aromatic ring and is at least one selected from an H atom, a CN group, an $NO_2$ group, a halogen atom, a $CH_3$ group, a $C_2H_5$ group, a $C_3H_7$ group, a $CF_3$ group, a $C_2F_5$ group and a $C_3F_7$ group; and m is an optional integer selected from 0 to 9.

The third example of compounds used as starting materials in the present invention can include at least one selected from substituted benzoylalkanes represented by the chemical formula (26), polyhydroxyalkanoates manufactured in that case can include those containing at least one in the molecule selected from 3-hydroxy(substituted benzoyl) alkanoate units represented by the chemical formula (27):

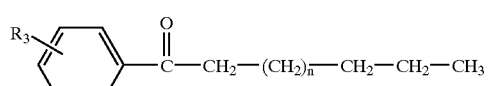

(26)

wherein $R_3$ shows a substituent on the aromatic ring and is at least one selected from an H atom, a CN group, an $NO_2$ group, a halogen atom, $CH_3$ group, a $C_2H_5$ group, a $C_3H_7$ group, a $CF_3$ group, a $C_2F_5$ group and a $C_3F_7$ group; and n is an optional integer selected from 0 to 9, and

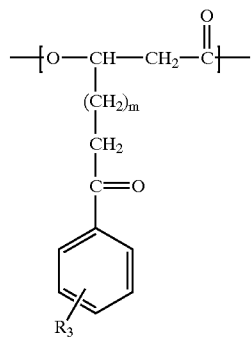

(27)

wherein $R_3$ shows a substituent on the aromatic ring and is at least one selected from an H atom, a CN group, an $NO_2$ group, a halogen atom, a $CH_3$ group, a $C_2H_5$ group, a $C_3H_7$ group, a $CF_3$ group, a $C_2F_5$ group and a $C_3F_7$ group; and m is an optional integer selected from 0 to 9

Describing the present inventive method more specifically, the manufacturing method of polyhydroxyalkanoates comprising one or more 3-hydroxyalkanoic acid units represented by the above described chemical formulas (23), (25) and (27) contains the processes where microorganisms are cultured in the medium containing one or more of any compounds represented by the above described chemical formulas (22), (24) and (26).

Thus, in the manufacturing method of the present invention, when comprising a step of culturing a microorganisms, i.e. a producing step of the polyhydroxyalkanoates by the microorganism, relationship between methylene chain length "n" showing in the formula of the starting material represented by the above described chemical formulas (22), (24) and (26) and side chain methylene chain length "m" shown in the formula represented by the above described chemical formulas (23), (25) and (27) of the units present in the molecules of the polyhydroxyalkanoates manufactured by the present inventive method can be designated as the following equation (1):

$$m = n - 21 \quad (1)$$

wherein 1 is an optional integer of $0 \leq 1 < (\frac{1}{2})n$

For example, when using 7-phenoxyheptane represented by the chemical formula (28) as a starting material, the polyhydroxyalkanoate produced comprises a 3-hydroxy-7-phenoxyheptanoic acid unit represented by the chemical formula (29) and a 3-hydroxy-5-phenoxyvaleric acid unit represented by the chemical formula (30):

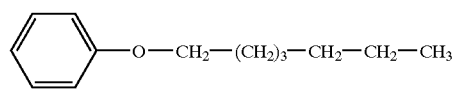

(28)

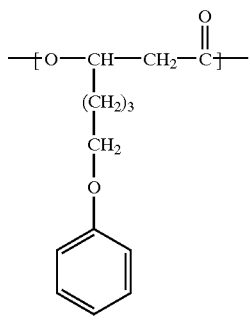

(29)

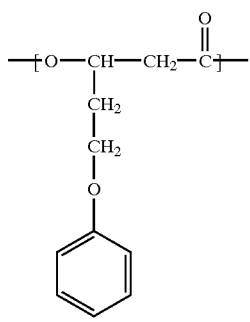

(30)

Further, the PHA obtained by the present inventive method may comprise at least one of units contained in the polymer molecule, which are a 3-hydroxyalkanoic acid unit represented by the following general formula (18):

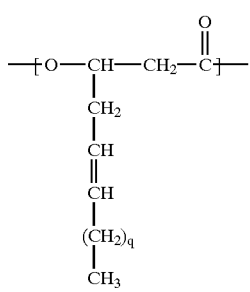

(18)

wherein p is an optional integer selected from 0 to 8 which can take one or more values in the polymer or a 3-hydroxy-alka-5-enoic acid unit represented by the following formula (19):

(19)

wherein z is an optional integer selected from 3 or 5 which can take one or more values in the polymer.

Furthermore, the number average molecular weight of PHAs obtained in the present inventive method is about 5000 to 1000000.

Microorganisms, culturing step, recovering step, etc. utilized in the present invention will be described as follows.
(Microorganisms)
Microorganisms used in the present inventive method can use any of them if polyhydroxyalkanoates containing a 3-hydroxy-substituted alkanoate unit in the molecule shown in general formula (14) having residues comprising substituted aromatic rings as shown in chemical formulas (15), (16) and (17) at the side chain can be produced using substituted alkanes of starting compounds as substrate materials shown in general formula (13) having residues comprising substituted aromatic rings as shown in chemical formulas (15), (16) and (17). Further, plural microorganisms can be mixed to be used within the scope that can attain the present inventive purposes if necessary.

Microorganisms used in the present invention are required to have at least capability of converting an alkane to an alkanoic acid, further they have capability of producing the PHA from the alkanoic acid. The capability of converting the alkane to the alkanoic acid is usually exhibited by having a group of enzymatic systems with alkane monooxygenase as a starting enzyme.

For such microorganisms, the microorganisms which belong to *Pseudomonas genus* are known, more specifically they are microorganisms separated from soil including *Pseudomonas cichorii* YN2 strain disclosed in Japanese Patent Application No. 11-371863 and *Pseudomonas oleovorans* ATCC 29347 disclosed in Japanese Patent Application Laid-Open No. 63-226291.

(Culturing Step)

In the culturing step of the manufacturing method of PHA s relating to the present invention, a polyhydroxyalkanoate which comprises at least one selected from a 3-hydroxy-substituted alkanoate unit group represented by the above described general formula (14) in the molecule is produced from at least one selected from a corresponding substituted alkane group represented as general formula (13) as a starting material using the above described microorganisms capable of producing the polyhydroxyalkanoate.

For usual culture of microorganisms used in this culturing step, e.g. preparation of the stored bacterial strain, multiplication to ensure the bacteria count or their active state required for production of PHA etc., the medium which contains the components required for growth of microorganisms used is suitably selected to be used. For example, any type of medium such as typical natural mediums (meat extract medium, yeast extract, etc.) and synthetic mediums with nutrition sources added may be used. Culturing conditions including temperature, aeration and agitation are suitably selected as the microorganisms used demand.

On the other hand, in the culturing step, when manufacturing the PHA which comprises at least one selected from an intended 3-hydorxy-substituted-alkanoate unit group represented as general formula (14) in the molecule using the above described PHA-producing microorganisms, the inorganic medium and the like which contain at least a carbon source for growth of microorganisms in addition to one selected from the group of substituted alkanes represented as the above described general formula (13) corresponding to the monomer unit as a material for the PHA production may be used as a medium. The initial content rate of the group of substituted alkanes represented as general formula (13) as a material is preferably selected with in the range of 0.01%–1% (v/v) per medium, more preferably 0.02%–0.2% (v/v).

The culturing step of the manufacturing method may be comprised of a step for culturing the microorganism in a medium containing dicyclopropylketone which induces alkane oxidation pathway. In general, linear alkane which is the substrate in a metabolic pathway of the alkane oxidation pathway, like octane and nonane, induces alkane oxidation pathway effectively. However, when such a linear alkane is used as an inducer, obtained PHA has high composition ratio of the medium-chain-length 3-hydroxyalkanoate units. Because linear alkane is converted to linear alkanoic acid through alkane oxidation pathway, and subsequently converted to a monomer substrate of the PHA through β-oxidation pathway.

The substituted alkanes used for monomer substrates in the present invention can also induce alkane oxidation pathway, therefore they can be incorporated as monomer units of PHA like the above-mentioned linear alkane. Alkane oxidation pathway has evolved to adapt linear alkane, consequently the substituted alkanes of the invention may not induce the pathway sufficiently compared with linear alkanes.

Dicyclopropylketone is known as gratuitous inducer. It functions as an inducer for the alkane oxidation pathway. However it cannot be oxidized by alkanemonooxygenase, hence it does not function as a substrate of the pathway (Journal of Bacteriology, 123, 546–556 (1975)). On this account, when induction of the alkane oxidation pathway is insufficient or to be enhanced, or target PHA needs a low composition ratio of medium-chain-length 3-hydroxyalkanoate units, dicyclopropylketone can be used for preferable inducer. In this case, dicyclopropylketone induces alkane oxidation pathway effectively and whole metabolizing activity can be used for the conversion of the substituted alkanes of the present invention. As a result, monomer units derived from the substituted alkanes are produced effectively and high yield of PHA and high composition ratio of monomer units derived from substituted alkanes are achieved.

Dycyclopropylketone only can be added to the culture medium or added with the substituted alkanes of the present invention. Concentration of the dicyclopropylketone is selected in consideration of a culture condition such as kind of nutrients in the medium, presence or absence of the substituted alkanes and their concentrations, number of the culturing steps and which step is it. The concentration of dicyclopropylketone is usually within the range of 0.001% to 1% (v/v), more preferably within the range of 0.01% to 0.1%.

The group of substituted alkanes represented by the general formula (13) does not always have good water solubility owing to its hydrophobicity, which is, however, not problematic at all because the above described microorganisms have a characteristic of enabling to utilize this compound as a substrate and even though there is some portion over the solubility partly in the suspended state at the beginning of culturing, the microorganisms gradually take it into their cells during continuation of culture to solve it in the medium in turn. Further, it is sometimes seen that the microorganism itself secretes a surfactant-like substance for efficient uptake, therefore it makes uptake of the substituted alkane as a substrate easy.

In addition, the group of substituted alkanes represented as general formula (13) as a material may be added to the medium sometimes in a solution of the solvent such as 1-hexadecene and n-hexadecane or in a form of fine suspension to increase its dispersibility. In such a case, the addition concentration of solvents such as 1-hexadecene and n-hexadecane used is required to be not more than 3% (v/v) to the medium.

In the medium, the substrate for growth which the microorganism utilize for its growth is added separately. For this substrate for multiplication, nutrients such as yeast extract, polypeptone and meat extract may be used. Further, they may be suitably selected from saccharides, organic acids generated as intermediates in the TCA cycle and organic acids generated through one step or two steps of biochemical reactions from the TCA cycle or their salts, amino acids or their salts, straight chain alkanoic acids having 4 to 12 carbons or their salts or the like, according to the strain used and considering their usefulness as a carbon source.

Of these various substrates for multiplication, suitably usable saccharides are one or more compounds selected from the group consisting of: aldoses such as glyceroaldehyde, erythrose, arabinose, xylose, glucose, galactose, mannose or fluctose; alditols such as glycerol, erythritol or xylitol: aldonic acids such as gluconic acid; uronic acids such as glucuronic acid or galacturonic acid; disaccharides such as maltose, sucrose or lactose.

Further, suitably usable organic acids or their salts are one or more compounds selected from the group consisting of pyruvic acid, malic acid, lactic acid, citric acid, succinic acid or their salts. On the other hand, suitably usable amino acids or their salts are one or more compounds selected from the group consisting of glutamic acid, aspartic acid or their salts.

Generally, of these various substrates for multiplication, it is generally more preferable to use polypeptone and saccharides, and of saccharides, it is further preferable to use at least one selected from the group consisting of glucose, fructose or mannose. The content ratio of these substrates for multiplication is desirably selected to be usually within the range of 0.1%–5% (w/v) per medium, more preferably within the range of 0.2%–2% (w/v).

For another method in the culturing step in which PHAs are produced/accumulated by a microorganism, the productivity sometimes improves when sufficient multiplication is performed first, then the bacteria are transferred into the medium with limited a nitrogen source such as ammonium chloride and further cultured in the state with a compound added as a substrate of an intended unit. For example, adoption of the multi-step method with a plurality of steps of the above described different culture conditions connected is included.

More specifically, it is more preferable to use the two-step culturing method etc. performing;

- as the first step, (step 1—1), the step of culturing a microorganism in the medium containing the group of substituted alkanes represented by the general formula (13) and polypeptone as a carbon source is continued from the logarithmic growth phase up to the stationary phase, then the bacteria are recovered by centrifugal separation once,
- and subsequently;
- as the second step, (step 1-2), the step of further culturing the microorganism cultured/multiplied in the former stage, step 1—1, in the medium containing the group of substituted alkanes represented by the general formula (13) and an organic acid or its salt as a carbon source;
- as the first step, (step 1-3), the step of culturing a microorganism in the medium containing the group of substituted alkanes represented by the general formula (13) and glucose as a carbon source is continued from the logarithmic growth phase up to the stationary phase, then the bacteria are recovered by centrifugal separation once, and subsequently;
- as the second step, (step 1-4), the step of further culturing the microorganism cultured/multiplied in the former stage, step 1-3, in the medium containing the group of substituted alkanes represented by the general formula (13) and glucose as a carbon source without a nitrogen source.

Further, it is preferable to use a two-stage culturing method comprising the first step (step 1-5), the step of culturing a microorganism in the medium containing the group of substituted alkanes represented by general formula (13) and polypeptone as a carbon source is continued up to the late logarithmic growth phase or the early stationary phase, then the bacteria are recovered by centrifugal separation once, and subsequently;

the second step (step 1-6), the step of further culturing the microorganism cultured in the former stage, step 1-5, in the medium containing the group of substituted alkanes represented by the general formula (13) and a saccharide as a carbon source but not containing any nitrogen source.

In the second step, described as (1-2), (1-4), and (1-6), the cultivation can be conducted without a nitrogen source.

Such two-step culturing method provides the following culturing forms: in the former stage, PHAs comprising at least one selected from the group of 3-hydroxy-substituted alkanoate units represented as the above general formula (14) corresponding to the group of substituted alkanes represented as the above general formula (13) as a material in the molecule are produced as well as pre-multiplication of the bacteria is performed; and in the latter stage, the pre-cultured bacteria are made to mainly produce PHAs in the medium without a nitrogen source. Consequently, these methods enable to further increase the PHA amount accumulated in the cells.

Dicyclopropylketone, which effectively induces alkane oxidation pathway, can be added to at least one of step (1—1) and step (1-2); step (1-3) and step (1-4); and step (1-5) and step (1-6), respectively, which would make conversion of the substituted alkanes to the corresponding alkanoate having substitutents effectively so that the yield of the PHA and composition ratio of the intended monomer units would become high.

Further, dicyclopropylketone alone can be used in place of the group of substituted alkanes in step 1—1, step 1-3 and step 1-5, which takes on a role of the culturing method of the first stage aiming chiefly at introducing the alkane oxidation pathway.

The temperature used in such culturing steps may the one that enables the above strain to grow well, for example, the range of 15–40° C. preferably the range of 20–35° C., more preferably the range of 20–30° C. are appropriately selected.

For culturing, any culturing method such as liquid culture and solid culture may be used if they can multiply the microorganisms and produce the PHA comprising at least one selected from the group of 3-hydroxy-substituted alkanoate units represented as the above general formula (14) in the molecule from at least one selected from the group of substituted alkanes represented as the above general formula (13) as a material contained in the medium. Further, if the material, carbon source and oxygen are appropriately supplied, any type including batch culture, fed batch culture, semi-continuous culture, continuous culture or the like may be used for example, a form of the liquid batch culture includes oxygen supplying methods by shaking using a shaking flask and by a stirring aeration method using a jar fermenter.

For the inorganic medium used in the above culturing method, any medium may be used if it contains components such as a phosphorous source (e.g. phosphate etc.), a nitrogen source (e.g. ammonium salt, nitrate, etc.) and the like capable of growing microorganisms, for example, including the MSB medium, M9 medium and the like.

In order to perform better multiplication and accompanying PHA production, it is necessary to supplement essential trace elements by addition of, for example, about 0.3% (v/v) solution of the above trace elements into the above described inorganic salt medium.

Further for the above culturing methods, any method used for usual culture of microorganisms may be used including batch type culture, fluid batch type culture, semi-continuous culture, continuous culture, reactor type culture and solid culture.

(Extraction/Purification Step of PHA)

For production/acquisition of PHA from accumulating microorganism cells relating to the present invention, the above described methods performed usually may be applied.

Examples will be shown as follows. Herein, "%" as described below is the weight basis unless otherwise specified.

EXAMPLES

Example 1

The *Pseudomonas cichorii* YN2 strain was inoculated in 200 mL of the M9 medium containing 0.5% D-glucose and 0.1% FBzVA, then this was cultured with shaking at 125 strokes/min at 30° C. After 48 hours, the bacteria were recovered by centrifugal separation, resuspended with 200 mL of the M9 medium containing 0.5% D-glucose and 0.1% 5-(4-fluorobenzoyl)valeric acid (hereinafter, sometimes abbrivated as FBzVA) but not containing a nitrogen source ($NH_4Cl$), further cultured with shaking at 125 strokes/min at 30° C. After 40 hours, the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membrane filter with the pore size of 0.45 $\mu$m, the filtrate was concentrated using a rotary evaporator, the concentrate was reprecipitated in cold methanol, further only the precipitate was recovered and dried in vacuo to obtain the PHA.

After methanolysis of the PHA obtained was performed according to the conventional method, the analysis by a gas chromatography-mass spectrometer (GC-MS, Shimadzu QP-5050, EI method) was carried out to identify the methyl-esterified form of the PHA monomer unit. Consequently, as shown in Table 3, the present PHA was identified to be the PHA comprising 3HFBzV as a monomer unit.

TABLE 3

Production of Polyhydroxyalkanoate by YN2 Strain

| | |
|---|---|
| Dry cell weight (mg/L) | 610 |
| Polymer weight (mg/L) | 150 |
| Composition of monomer unit (TIC peak area ratio) | |
| 3-Hydroxyhexanoic acid | 0.2% |
| 3-Hydroxyoctanoic acid | 4.5% |
| 3-Hydroxydecanoic acid | 9.8% |
| 3-Hydroxydodecanoic acid | 4.0% |
| 3-Hydroxydodecenoic acid | 7.1% |
| 3-Hydroxy-5-(4-fluorobenzoyl)valeric acid | 74.4% |

The molecular weight of the PHA was evaluated by gel permeation chromatography (GPC: Tosoh HLC-8220, Column; Polymer Laboratory PL gel MIXED-C (5 $\mu$m), Solvent; chloroform, conversion to polystyrene). Consequently, this was Mn=30,000 and Mw=78,000.

Example 2

The *Pseudomonas cichorii* YN2 strain was inoculated in 200 mL of the M9 medium containing 0.5% D-glucose and 0.1% FBzVA, then this was cultured with shaking at 125 strokes/min at 30° C. After 48 hours, the bacteria were recovered by centrifugal separation, washed once with cold methanol and dried in vacuo.

This vacuum dried pellet was suspended in 20 mL of chloroform and stirred at 60° C. for 20 hours to extract PHA. After the extract was filtered through a membrane filter with the pore size of 0.45 $\mu$m, the filtrate was concentrated using a rotary evaporator, the concentrate was reprecipitated in cold methanol, further only the precipitate was recovered and dried in vacuo to obtain the PHA.

After methanolysis of the PHA obtained was performed according to the conventional method, the analysis by a gas chromatography-mass spectrometer (GC-MS, Shimadzu QP-5050, EI method) was carried out to identify the methyl-esterified form of the PHA monomer unit. Consequently, as shown in Table 4, the present PHA was identified to be the PHA comprising 3HFBzV as a monomer unit.

TABLE 4

Production of Polyhydroxyalkanoate by YN2 Strain

| | |
|---|---|
| Dry cell weight (mg/L) | 490 |
| Polymer weight (mg/L) | 36 |
| Composition of monomer unit (TIC peak area ratio) | |
| 3-Hydroxybutyric acid | 0.1% |
| 3-Hydroxyhexanoic acid | 0.3% |
| 3-Hydroxyoctanoic acid | 7.5% |
| 3-Hydroxydecanoic acid | 12.2% |
| 3-Hydroxydodecanoic acid | 4.6% |
| 3-Hydroxydodecenoic acid | 5.0% |
| 3-Hydroxy-5-(4-fluorobenzoyl)valeric acid | 70.3% |

Example 3

The *Pseudomonas cichorii* YN2 strain was inoculated in 200 mL of the M9 medium containing 0.5% disodium malate and 0.1% FBzVA, then this was cultured with shaking at 125 strokes/min at 30° C. After 4 days, the bacteria were recovered by centrifugal separation, washed once with cold methanol and dried in vacuo.

This vacuum dried pellet was suspended in 20 mL of chloroform and stirred at 60° C. for 20 hours to extract PHA. After the extract was filtered through a membrane filter with the pore size of 0.45 $\mu$m, the filtrate was concentrated using a rotary evaporator, the concentrate was reprecipitated in cold methanol, further only the precipitate was recovered and dried in vacuo to obtain the PHA.

After methanolysis of the PHA obtained was performed according to the conventional method, the analysis by a gas chromatography-mass spectrometer (GC-MS, Shimadzu QP-5050, EI method) was carried out to identify the methyl-esterified form of the PHA monomer unit. Consequently, as shown in Table 5, the present PHA was identified to be the PHA comprising 3HFBzV as a monomer unit.

TABLE 5

Production of Polyhydroxyalkanoate by YN2 Strain

| | |
|---|---|
| Dry cell weight (mg/L) | 480 |
| Polymer weight (mg/L) | 190 |
| Composition of monomer unit (TIC peak area ratio) | |
| 3-Hydroxybutyric acid | 60.7% |

TABLE 5-continued

Production of Polyhydroxyalkanoate by YN2 Strain

| | |
|---|---|
| 3-Hydroxyhexanoic acid | 0.8% |
| 3-Hydroxyoctanoic acid | 8.3% |
| 3-Hydroxydecanoic acid | 5.1% |
| 3-Hydroxydodecanoic acid | 1.9% |
| 3-Hydroxydodecenoic acid | 1.5% |
| 3-Hydroxy-5-(4-fluorobenzoyl)valeric acid | 21.7% |

Example 4

The *Pseudomonas cichorii* YN2 strain was inoculated in 200 mL of the M9 medium containing 0.5% yeast extract (Oriental Yeast Industry Co., Ltd.-made) and 0.1% FBzVA, then this was cultured with shaking at 125 strokes/min at 30° C. After 48 hours, the bacteria were recovered by centrifugal separation, washed once with cold methanol and dried in vacuo.

This vacuum dried pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain the PHA.

After methanolysis of the PHA obtained was performed according to the conventional method, the analysis by a gas chromatography-mass spectrometer (GC-MS, Shimadzu QP-5050, EI method) was carried out to identify the methyl-esterified form of the PHA monomer unit. Consequently, as shown in Table 6, the present PHA was identified to be the PHA comprising 3HFBzV as a monomer unit.

TABLE 6

Production of Polyhydroxyalkanoate by YN2 Strain

| | |
|---|---|
| Dry cell weight (mg/L) | 520 |
| Polymer weight (mg/L) | 60 |
| Composition of monomer unit (TIC peak area ratio) | |
| 3-Hydroxyhexanoic acid | 0.8% |
| 3-Hydroxyoctanoic acid | 3.6% |
| 3-Hydroxydecanoic acid | 4.0% |
| 3-Hydroxydodecanoic acid | 1.4% |
| 3-Hydroxy-5-(4-fluorobenzoyl)valeric acid | 90.2% |

Example 5

The *Pseudomonas cichorii* YN2 strain was inoculated in 200 mL of the M9 medium containing 0.51 polypeptone (Nippon Pharmaceutical Co., Ltd.-made) and 0.1% FBzVA, then this was cultured with shaking at 125 strokes/min at 30° C. After 48 hours, the bacteria were recovered by centrifugal separation, washed once with cold methanol and dried in vacuo.

This vacuum dried pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain the PHA.

After methanolysis of the PHA obtained was performed according to the conventional method, the analysis by a gas chromatography-mass spectrometer (GC-MS, Shimadzu QP-5050, EI method) was carried out to identify the methyl-esterified form of the PHA monomer unit. Consequently, as shown in Table 7, the present PHA was identified to be the PHA comprising 3HFBzV as a monomer unit.

TABLE 7

Production of Polyhydroxyalkanoate by YN2 Strain

| | |
|---|---|
| Dry cell weight (mg/L) | 690 |
| Polymer weight (mg/L) | 290 |
| Composition of monomer unit (TIC peak area ratio) | |
| 3-Hydroxybutyric acid | 1.2% |
| 3-Hydroxyhexanoic acid | 0.3% |
| 3-Hydroxyoctanoic acid | 4.7% |
| 3-Hydroxydecanoic acid | 9.8% |
| 3-Hydroxydodecanoic acid | 3.1% |
| 3-Hydroxydodecenoic acid | 3.5% |
| 3-Hydroxy-5-(4-fluorobenzoyl)valeric acid | 77.4% |

Example 6

The *Pseudomonas cichorii* H45 strain was inoculated in 200 mL of the M9 medium containing 0.5% D-glucose and 0.1% FBzVA, then this was cultured with shaking at 125 strokes/min at 30° C. After 48 hours, the bacteria were recovered by centrifugal separation, resuspended with 200 mL of the M9 medium containing 0.5% D-glucose and 0.1% FBzVA but not containing a nitrogen source (NH$_4$Cl), further cultured with shaking at 125 strokes/min at 30° C. After 40 hours, the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain the PHA.

After methanolysis of the PHA was performed according to the conventional method, the analysis by a gas chromatography-mass spectrometer (GC-MS, Shimadzu QP-5050, EI method) was carried out to identify the methyl-esterified form of the PHA monomer unit. Consequently, as shown in Table 8, the present PHA was identified to be the PHA comprising 3HFBzV as a monomer unit.

TABLE 8

Production of Polyhydroxyalkanoate by H45 Strain

| | |
|---|---|
| Dry cell weight (mg/L) | 490 |
| Polymer weight (mg/L) | 90 |
| Composition of monomer unit (TIC peak area ratio) | |
| 3-Hydroxyhexanoic acid | 0.1% |
| 3-Hydroxyoctanoic acid | 4.0% |
| 3-Hydroxydecanoic acid | 8.8% |
| 3-Hydroxydodecanoic acid | 5.1% |
| 3-Hydroxydodecenoic acid | 7.8% |
| 3-Hydroxy-5-(4-fluorobenzoyl)valeric acid | 74.2% |

The molecular weight of this PHA was evaluated by gel permeation chromatography (GPC; Tosoh HLC-8220, Column; Polymer Laboratory PL gel MIXED-C (5 μm), Solvent; chloroform, conversion to polystyrene). Consequently, this was Mn=26,000 and Mw=61,000.

Example 7

The *Pseudomonas jessenii* P161 strain was inoculated in 200 mL of the M9 medium containing 0.5% D-glucose and 0.1% FBzVA, then this was cultured with shaking at 125 strokes/min at 30° C. After 48 hours, the bacteria were recovered by centrifugal separation, resuspended with 200 mL of the M9 medium containing 0.5% D-glucose and 0.1% FBzVA but not containing a nitrogen source ($NH_4Cl$), further cultured with shaking at 125 strokes/min at 30° C. After 40 hours, the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain the PHA.

After methanolysis of the PHA was performed according to the conventional method, the analysis by a gas chromatography-mass spectrometer (GC-MS, Shimadzu QP-5050, EI method) was carried out to identify the methyl-esterified form of the PHA monomer unit. Consequently, as shown in Table 9, the present PHA was identified to be the PHA comprising 3HFBzV as a monomer unit.

TABLE 9

Production of Polyhydroxyalkanoate by P161 Strain

| | |
|---|---|
| Dry cell weight (mg/L) | 590 |
| Polymer weight (mg/L) | 110 |
| Composition of monomer unit (TIC peak area ratio) | |
| 3-Hydroxyoctanoic acid | 3.5% |
| 3-Hydroxydecanoic acid | 8.0% |
| 3-Hydroxydodecanoic acid | 4.9% |
| 3-Hydroxydodecenoic acid | 5.6% |
| 3-Hydroxy-5-(4-fluorobenzoyl)valeric acid | 78.0% |

The molecular weight of this PHA was evaluated by gel permeation chromatography (GPC; Tosoh HLC-8220, Column; Polymer Laboratory PL gel MIXED-C (5 μm), Solvent; chloroform, conversion to polystyrene). Consequently, this was Mn=41,000 and Mw=110,000.

Example 8

200 mL of the M9 medium containing 0.5% (w/v) polypeptone and n-amylbenzene (3 concentrations: 0.025%, 0.05% and 0.1% (v/v)) was prepared, placed into a 500 mL volume shaking flask and sterilized by an autoclave. Each flask was returned to a room temperature and the YN2 strain on the agar plate was inoculated, then this was cultured with shaking at 125 strokes/min at 30° C. for 24 hours. After completion of the culture the bacteria were recovered by centrifugal separation, washed once with cold methanol and lyophilized.

This lyophilized pellet was weighed, then suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain the PHA and weigh it. Each yield is shown in Table 10.

The molecular weight of this PHA obtained in the 0.05% amylbenzene system was evaluated by gel permeation chromatography (GPC; Tosoh HLC-8220, Column, Polymer Laboratory PL gel MIXED-C (5 μm), Solvent: chloroform, conversion to polystyrene). Consequently, the number average molecular weight (Mn) was Mn=90,000 and the molecular weight distribution is 1.9.

Composition of the PHA obtained was analyzed as follows. That is, about 10 mg of the PHA was placed into a 25 mL volume pear-shape flask, dissolved in 2 mL chloroform, and to this solution, 2 mL of a methanol solution containing 3% sulfuric acid was added, and the mixture was reacted for 3.5 hours refluxing at 100° C.

After completion of the reaction, 10 mL of deionized water was added, shaken vigorously for 10 min, then the lower chloroform layer separated into two layers was taken out, dehydrated with magnesium sulfate, then this chloroform layer was submitted to a gas chromatography-mass spectrometer (GC-MS, Shimadzu QP-5050, EI method) to identify the methyl-esterified form of the PHA monomer unit. The results are shown in Table 11.

Figure 2:
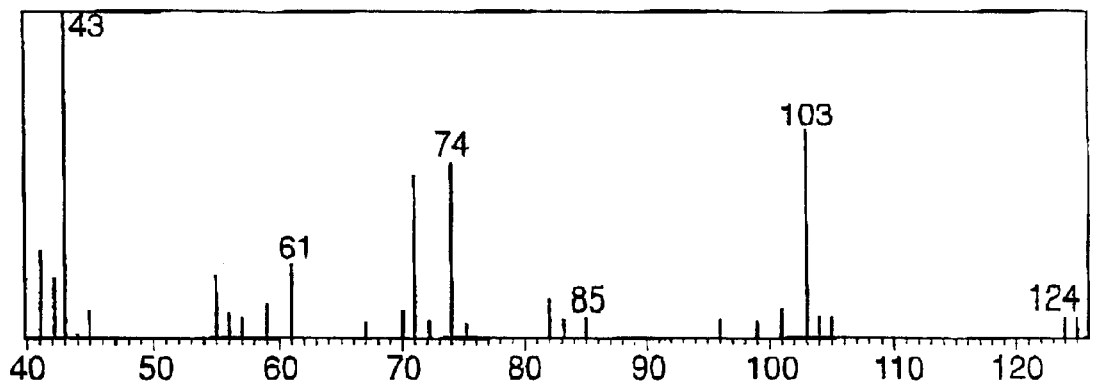
FIG. 2 shows a mass spectrum of methyl 3-hydroxyoctanoate when PHA obtained in the system with 0.1% amylbenzene added in Example 8 was measured by GC-MS after methanolysis treatment.
Figure 3:
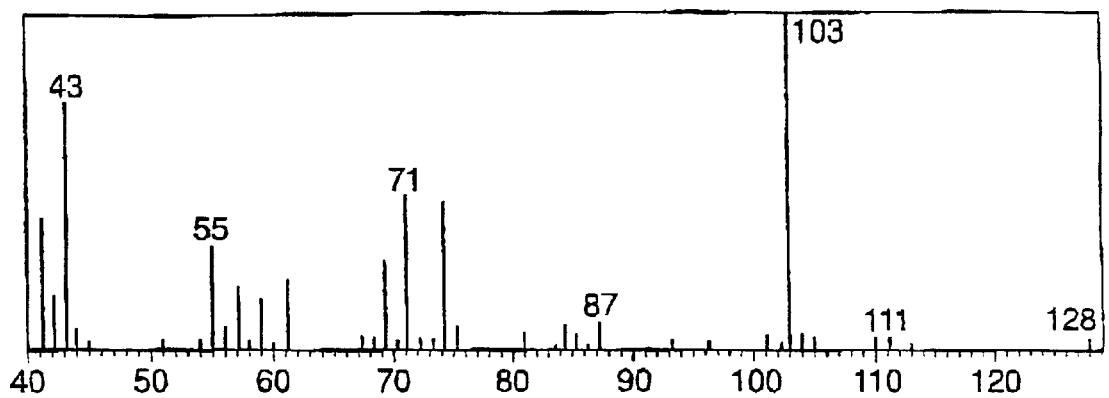
FIG. 3 shows a mass spectrum of methyl 3-hydroxydecanoate when PHA obtained in the system with 0.1% imylbenzene added in Example 8 was measured by GC-MS after methanolysis treatment.
Figure 4:
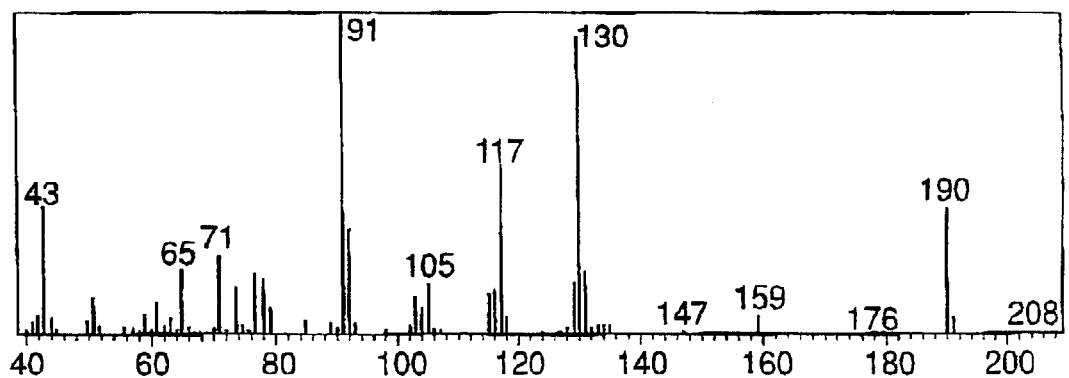
FIG. 4 shows a mass spectrum of methyl 3-hydroxy-5-phenylvalerate when PHA obtained in the system with 0.1% amylbenzene added in Example 8 was measured by 3C-MS after methanolysis treatment.

Further, the mass spectra of peaks obtained by GC-MS analysis of 0.1% amylbenzene system are shown in FIGS. 1 to 4 (corresponding to methyl esters of FIG. 1: 3-hydroxybutyric acid, FIG. 2: 3-hydroxyoctanoic acid, FIG. 3: 3-hydroxydecanoic acid, FIG. 4: and 3-hydroxy-5-phenylvaleric acid, respectively).

TABLE 10

| AMB (%) | CDW (mg/L) | PDW (mg/L) | Yield (%) |
|---|---|---|---|
| 0.025 | 900 | 65 | 7.2 |
| 0.05 | 1050 | 200 | 19.0 |
| 0.1 | 850 | 65 | 7.6 |

AMB: amylbenzene,
CDW: dry cell weight,
PDW: dry polymer cell weight,
Yield: PDW/CDW × 100

TABLE 11

| AMB (%) | 3HB | 3HO | 3HD | 3HPV |
|---|---|---|---|---|
| 0.025 | 51.1 | 0.7 | 2.1 | 46.1 |
| 0.05 | 19.2 | 0.7 | 3.6 | 76.5 |
| 0.1 | 24.6 | 2.1 | 3.8 | 72.5 |

AMB: amylbenzene, 3HB: 3-hydroxybutyric acid,
3HO: 3-hydroxyoctanoic acid,
3HD: 3-hydroxydecanoic acid,
3HPV: 3-hydroxy-5-phenylvaleric acid

Example 9

200 mL of the M9 medium containing 0.5% (w/v) sodium glutamate and n-amylbenzene (0.05% and 0.1% (v/v)) was prepared, placed into a 500 mL volume shaking flask and sterilized by an autoclave.

The flask was returned to a room temperature and the YN2 strain on the agar plate was inoculated, then this was cultured with shaking at 125 strokes/min at 30° C. for 26 hours.

After completion of the culture, the bacteria were recovered by centrifugal separation, transferred to the M9 medium without the $NH_4Cl$ component (concentrations of sodium glutamate and amylbenzene are same), and cultured with shaking at 125 strokes/min at 30° C. for 20 hours.

After completion of the culture, the bacteria was recovered by centrifugal separation, washed once with cold methanol and lyophilized.

This lyophilized pellet was weighed, then suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain the PHA and weigh it. Each yield is shown in Table 12.

Composition of the PHA obtained was analyzed by the method similar to Example 8. The results are shown in Table 13.

TABLE 12

| CDW (mg/L) | PDW (mg/L) | Yield (%) |
|---|---|---|
| 900 | 320 | 35.6 |

CDW: dry cell weight,
PDW: dry polymer cell weight,
Yield: PDW/CDW × 100

TABLE 13

| 3HB | 3HD | 3HPV |
|---|---|---|
| 88.7 | 3.1 | 8.2 |

3HB: 3-hydroxybutyric acid,
3HD: 3-hydroxydecanoic acid,
3HPV: 3-hydoxy-5-phenylvaleric acid Example 10

200 mL of the M9 medium containing 0.5% (w/v) polypeptone and n-hexanophenone (4 concentrations: 0.01%, 0.025%, 0.05% end 0.1% (v/v)) was prepared, placed into a 500 mL volume shaking flask and sterilized by an autoclave.

Each flask was returned to a room temperature and the *Pseudomonas cichorii* YN2 strain was inoculated, then this was cultured with shaking at 125 strokes/min at 30° C. After 48 hours, the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain the PHA. Each yield is shown in Tables 14 to 17 (Table 14: Results of 0.01% n-hexanophenone, Table 15: Results of 0.025% n-hexanophenone, Table 16: Results of 0.05% n-hexanophenone, Table 17: Results of 0.1% n-hexanophenone).

TABLE 14

| | |
|---|---|
| Dry cell weight | 815 mg/L |
| Dry polymer weight | 50 mg/L |
| Dry polymer weight/Dry cell weight | 6.1% |
| Composition of monomer unit (TIC peak area ratio) | |
| 3-Hydroxybutyric acid | 42.4% |
| 3-Hydroxyhexanoic acid | 0.0% |
| 3-Hydroxyoctanoic acid | 5.2% |
| 3-Hydroxydecanoic acid | 13.8% |

TABLE 14-continued

| | |
|---|---|
| 3-Hydroxydodecanoic acid | 12.1% |
| 3-Hydroxydodecenoic acid | 3.7% |
| 3-Hydroxy-5-benzoylvaleric acid | 22.8% |

TABLE 15

| | |
|---|---|
| Dry cell weight | 775 mg/L |
| Dry polymer weight | 60 mg/L |
| Dry polymer weight/Dry cell weight | 7.7% |
| Composition of monomer unit (TIC peak area ratio) | |
| 3-Hydroxybutyric acid | 32.8% |
| 3-Hydroxyhexanoic acid | 0.0% |
| 3-Hydroxyoctanoic acid | 3.3% |
| 3-Hydroxydecanoic acid | 12.4% |
| 3-Hydroxydodecanoic acid | 12.9% |
| 3-Hydroxydodecenoic acid | 3.8% |
| 3-Hydroxy-5-benzoylvaleric acid | 34.8% |

TABLE 16

| | |
|---|---|
| Dry cell weight | 685 mg/L |
| Dry polymer weight | 80 mg/L |
| Dry polymer weight/Dry cell weight | 11.7% |
| Composition of monomer unit (TIC peak area ratio) | |
| 3-Hydroxybutyric acid | 21.7% |
| 3-Hydroxyhexanoic acid | 0.0% |
| 3-Hydroxyoctanoic acid | 4.2% |
| 3-Hydroxydecanoic acid | 12.1% |
| 3-Hydroxydodecanoic acid | 12.0% |
| 3-Hydroxydodecenoic acid | 2.8% |
| 3-Hydroxy-5-benzoylvaleric acid | 47.2% |

TABLE 17

| | |
|---|---|
| Dry cell weight | 755 mg/L |
| Dry polymer weight | 70 mg/L |
| Dry polymer weight/Dry cell weight | 9.3% |
| Composition of monomer unit (TIC peak area ratio) | |
| 3-Hydroxybutyric acid | 12.6% |
| 3-Hydroxyhexanoic acid | 0.2% |
| 3-Hydroxyoctanoic acid | 2.3% |
| 3-Hydroxydecanoic acid | 7.7% |
| 3-Hydroxydodecanoic acid | 8.0% |
| 3-Hydroxydodecenoic acid | 1.7% |
| 3-Hydroxy-5-benzoylvaleric acid | 60.5% |

The molecular weight of the PHA obtained (use of 0.1% (v/v) n-hexanophenone) was evaluated by gel permeation chromatography (GPC; Tosoh HLC-8220, Column; Tosoh TSK-GEL Super HM-H. Solvent; chloroform, conversion to polystyrene). Consequently, this was Mn=68,000 and Mw=454,000.

Further, after methanolysis of the PHA was performed according to the conventional method, the analysis by a gas chromatography-mass spectrometer (GC-MS, Shimadzu QP-5050, EI method) was carried out to identify the methylesterified form of the PHA monomer unit. The results are shown in Tables 14 to 17. Consequently, as shown in Tables 14 to 17, the present PHA was identified to be the PHA comprising 3-hydroxy-5-benzoylvaleric acid (hereinafter, abbreviated as 3HBV if necessary) represented by the chemical formula (31) as a monomer unit.

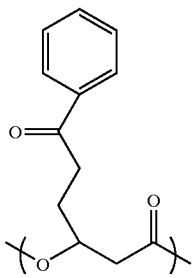

(31)

The compound was analyzed using the NMR apparatus in the following conditions.

Figure 5:
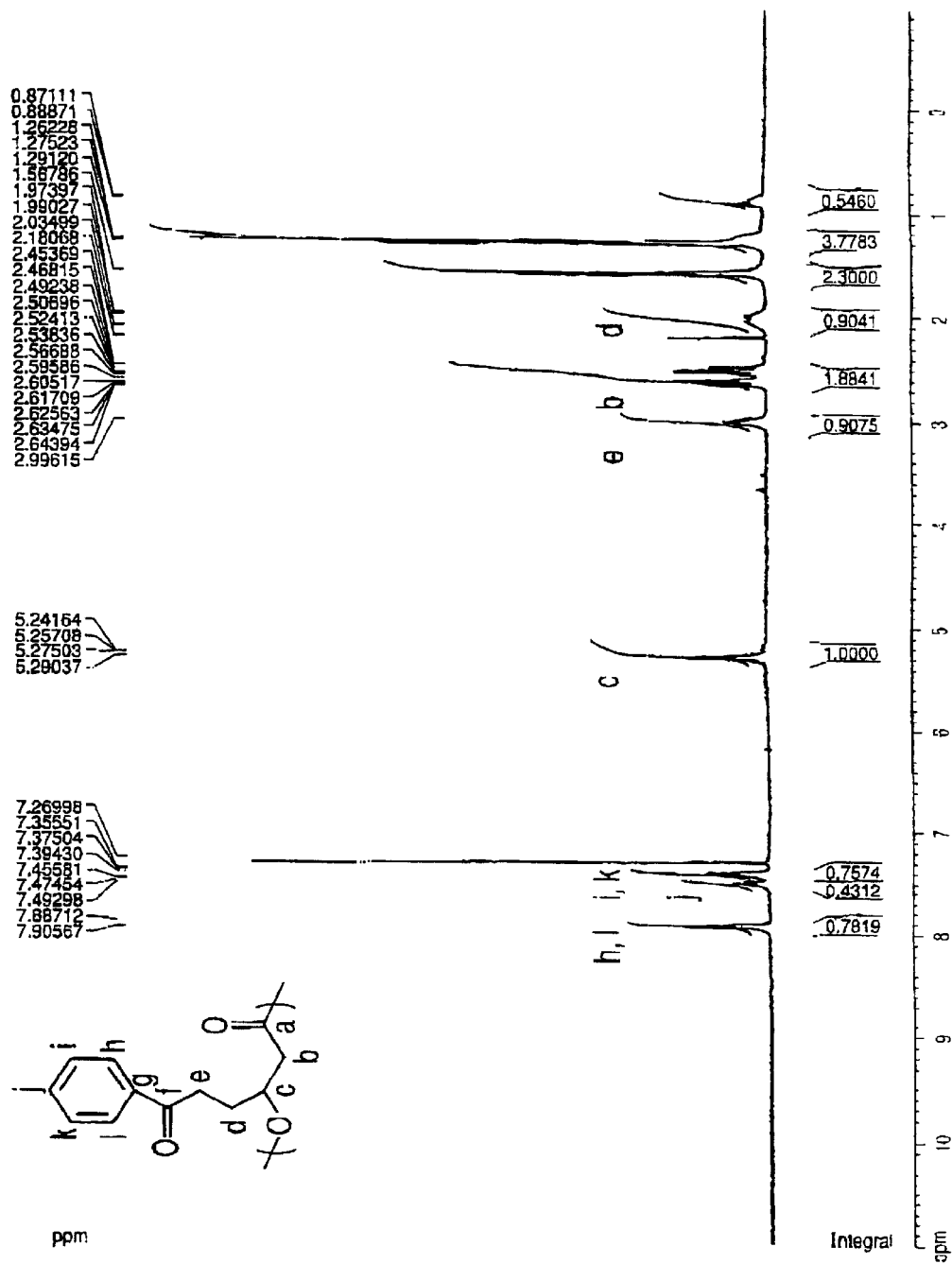
FIG. 5 shows a 1H-NMR spectrum chart in Example 10.
Figure 6:
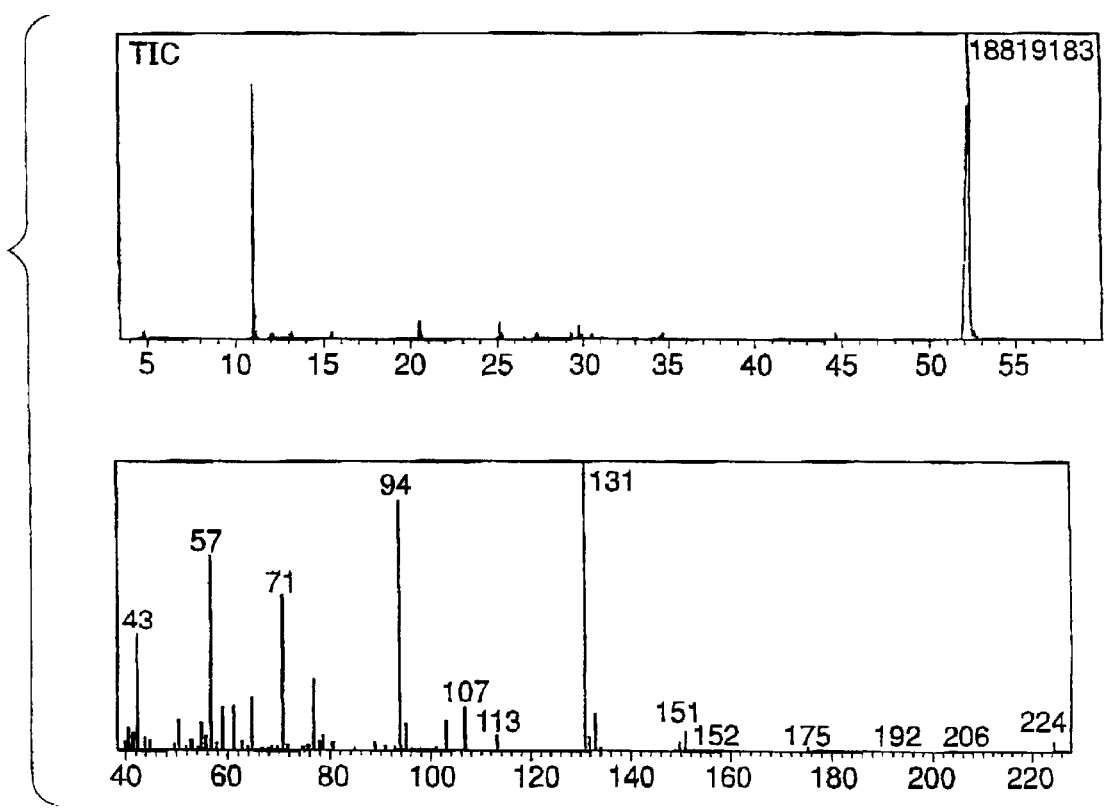
FIG. 6 shows a TIC and a mass spectrum of methyl 3-hydroxy-5-phenoxyvalerate when PHA obtained in Example 13 was measured by GC-MS after methanolysis treatment.

<Measuring apparatus> FT-NMR: Bruker DPX 400
　Resonance frequency; 1H=400 MHz
<Measuring apparatus> Measuring nuclide: 1H
　Solvent used: $CDCl_3$
　Reference: capillary-sealed $CDCl_3$
　Measuring temperature: room temperature
　The 1H-NMR spectrum chart is shown in FIG. 5 and the assignment results are shown in Table 18, respectively.

TABLE 18

| Chemical shift (ppm) | Integrated value | type | Position |
|---|---|---|---|
| 2.04 | 2 | m | d |
| 2.56 | 2 | m | b |
| 3.00 | 2 | m | e |
| 5.26 | 1 | m | c |
| 7.36 | 2 | m | i, k |
| 7.46 | 1 | t | j |
| 7.89 | 2 | d | h, l |

Example 11

200 mL of the M9 medium containing 0.5% (w/v) sodium glutamate and 0.1% (v/v) n-hexanophenone was prepared, placed into a 500 mL volume shaking flask and sterilized by an autoclave.

The flask was returned to a room temperature and the *Pseudomonas cichorii* YN2 strain on the agar plate was inoculated, then this was cultured with shaking at 125 strokes/min at 30° C. After 48 hours, the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain the PHA.

After methanolysis of the PHA obtained was performed according to the conventional method, the analysis by a gas chromatography-mass spectrometer (GC-MS, Shimadzu QP-5050, EI method) was carried out to identify the methyl-esterified form of the PHA monomer unit. The results are shown in Table 19. Consequently, as shown in Table 19, the present PHA was identified to be the PHA comprising 3HBV represented by the chemical formula (31) as a monomer unit.

TABLE 19

| | |
|---|---|
| Dry cell weight | 1040 mg/L |
| Dry polymer weight | 445 mg/L |
| Dry polymer weight/Dry cell weight | 42.8% |
| Composition of monomer unit (TIC peak area ratio) | |
| 3-Hydroxybutyric acid | 39.4% |
| 3-Hydroxyhexanoic acid | 0.3% |
| 3-Hydroxyoctanoic acid | 3.9% |
| 3-Hydroxydecanoic acid | 11.01% |
| 3-Hydroxydodecanoic acid | 6.5% |
| 3-Hydroxydodecenoic acid | 8.3% |
| 3-Hydroxy-5-benzoylvaleric acid | 30.5% |

Example 12

200 mL of the M9 medium containing 0.5% (w/v) yeast extract and 0.1% (v/v) n-hexanophenone was prepared, placed into a 500 mL volume shaking flask and sterilized by an autoclave.

The flask was returned to a room temperature and the *Pseudomonas cichorii* YN2 strain on the agar plate was inoculated, then this was cultured with shaking at 125 strokes/min at 30° C. After 48 hours, the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain the PHA.

After methanolysis of the PHA obtained was performed according to the conventional method, the analysis by a gas chromatography-mass spectrometer (GC-MS. Shimadzu QP-5050, EI method) was carried out to identify the methyl-esterified form of the PHA monomer unit. The results are shown in Table 20. Consequently, as shown in Table 20, the present PHA was identified to be the PHA comprising 3HBV represented by the chemical formula (31) as a monomer unit.

TABLE 20

| | |
|---|---|
| Dry cell weight | 925 mg/L |
| Dry polymer weight | 25 mg/L |
| Dry polymer weight/Dry cell weight | 2.7% |
| Composition of monomer unit (TIC peak area ratio) | |
| 3-Hydroxybutyric acid | 73.5% |
| 3-Hydroxyhexanoic acid | 0.0% |
| 3-Hydroxyoctanoic acid | 2.0% |
| 3-Hydroxydecanoic acid | 3.7% |
| 3-Hydroxydodecanoic acid | 0.0% |
| 3-Hydroxydodecenoic acid | 2.0% |
| 3-Hydroxy-5-benzoylvaleric acid | 18.8% |

Example 13

200 mL of the M9 medium containing 0.5% (w/v) sodium glutamate and 0.1% (v/v) n-phenoxypentane was prepared, placed into a 500 mL volume shaking flask and sterilized by an autoclave.

The flask was returned to a room temperature and the *Pseudomonas cichorii* YN2 strain on the agar plate was inoculated, then this was cultured with shaking at 125 strokes/min at 30° C. After 120 hours, the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membrane filter with the pore size of 0.45 µm, the filtrate was concentrated using a rotary evaporator, the concentrate was reprecipitated in cold methanol, further only the precipitate was recovered and dried in vacuo to obtain 23 mg of the PHA.

The molecular weight of this PHA was evaluated by gel permeation chromatography (GPC; Tosoh HLC-8220, Column; Tosoh TSK-GEL super HM-H, Solvent; chloroform, conversion to polystyrene). Consequently, this was Mn=64,000 and Mw=141,000.

Further, after methanolysis of the PHA obtained was performed according to the conventional method, the analysis by a gas chromatography-mass spectrometer (GC-MS, Shimadzu QP-5050, EI method) was carried out to identify the methyl-esterified form of the PHA monomer unit. The results are shown in Table 21.

TABLE 21

Production of PHA Produced in Example 13 and Composition of Monomer Unit

| | |
|---|---|
| Dry cell weight | 570 mg/L |
| Dry polymer weight | 115 mg/L |
| Dry polymer weight/Dry cell weight | 20.2% |
| Composition of monomer unit (TIC peak area ratio) | |
| 3-Hydroxybutyric acid | 15.0% |
| 3-Hydroxyvaleric acid | 0.3% |
| 3-Hydroxyhexanoic acid | 0.1% |
| 3-Hydroxyoctanoic acid | 1.0% |
| 3-Hydroxydecanoic acid | 1.0% |
| 3-Hydroxydodecanoic acid | 0.3% |
| 3-Hydroxydodecenoic acid | 0.8% |
| 3-Hydroxy-5-phenoxyvaleric acid | 81.5% |

Consequently, as shown in Table 21, the present PHA was identified to be the PHA comprising 3-hydroxy-5-phenoxyvaleric acid (hereinafter, abbreviated as 3HPxV) represented by the chemical formula (32) as a monomer unit.

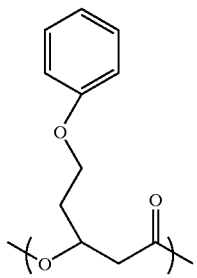

(32)

Example 14

200 mL of the 19 medium containing 0.5% (w/v) polypeptone and 0.1% (v/v) n-phenoxypentane was prepared, placed into a 500 mL volume shaking flask and sterilized by an autoclave.

The flask was returned to a room temperature and the *Pseudomonas cichorii* YN2 strain on the agar plate was inoculated, then this was cultured with shaking at 125 strokes/min at 30° C. After 120 hours, the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membrane filter with the pore size of 0.45 µm, the filtrate was concentrated using a rotary evaporator, the concentrate was reprecipitated in cold methanol, further only the precipitate was recovered and dried in vacuo to obtain 2 mg of the PHA.

After methanolysis of the PHA obtained was performed according to the conventional method, the analysis by a gas chromatography-mass spectrometer (GC-MS, Shimadzu QP-5050, EI method) was carried out to identify the methyl-esterified form of the PHA monomer unit. The results are shown in Table 22. Consequently, as shown in Table 22, the present PHA was identified to be the PHA comprising 3HPxV represented by the chemical formula (32) as a monomer unit.

TABLE 22

Production of PHA Produced in Example 14 and Composition of Monomer Unit

| | |
|---|---|
| Dry cell weight | 560 mg/L |
| Dry polymer weight | 10 mg/L |
| Dry polymer weight/Dry cell weight | 1.8% |
| Composition of monomer unit (TIC peak area ratio) | |
| 3-Hydroxybutyric acid | 1.8% |
| 3-Hydroxyhexanoic acid | 0.0% |
| 3-Hydroxyoctanoic acid | 0.0% |
| 3-Hydroxydecanoic acid | 0.0% |
| 3-Hydroxydodecanoic acid | 0.0% |
| 3-Hydroxydodecenoic acid | 0.0% |
| 3-Hydroxy-5-phenoxyvaleric acid | 98.2% |

Example 15

(Synthesis of 1-(4-fluorophenyl)-1-hexanone (FPHxO))

100 mL of tetrahydrofuran was placed into a four-neck round-bottom flask, then 7.92 g (0.05 mol) of 4-fluorobenzoyl chloride and 0.53 g (1.5 mmol) of tris (acetylacetone)iron (III) were added and stirred under a nitrogen atmosphere. To this solution pentylmagnesium bromide was added at a room temperature and stirred at a room temperature for 10 min. After completion of the reaction, this solution was acidified with dilute hydrochloric acid and the organic phase was extracted with diethyl ether. Further, the organic phase was neutralized with satd. sodium hydrogencarbonate solution and washed with satd. sodium chloride solution. The organic phase was dehydrated with anhydrous magnesium sulfate, then diethyl ether was evaporated by a rotary evaporator and dried by a vacuum pump to obtain crude FPHxO.

The purification was performed by being isolated by silica gel column chromatography (developing solvent: n-hexane:ethyl acetate=30:1) followed by being recrystallized with n-hexane to obtain 5.23 g of FPHxO.

Figure 7:
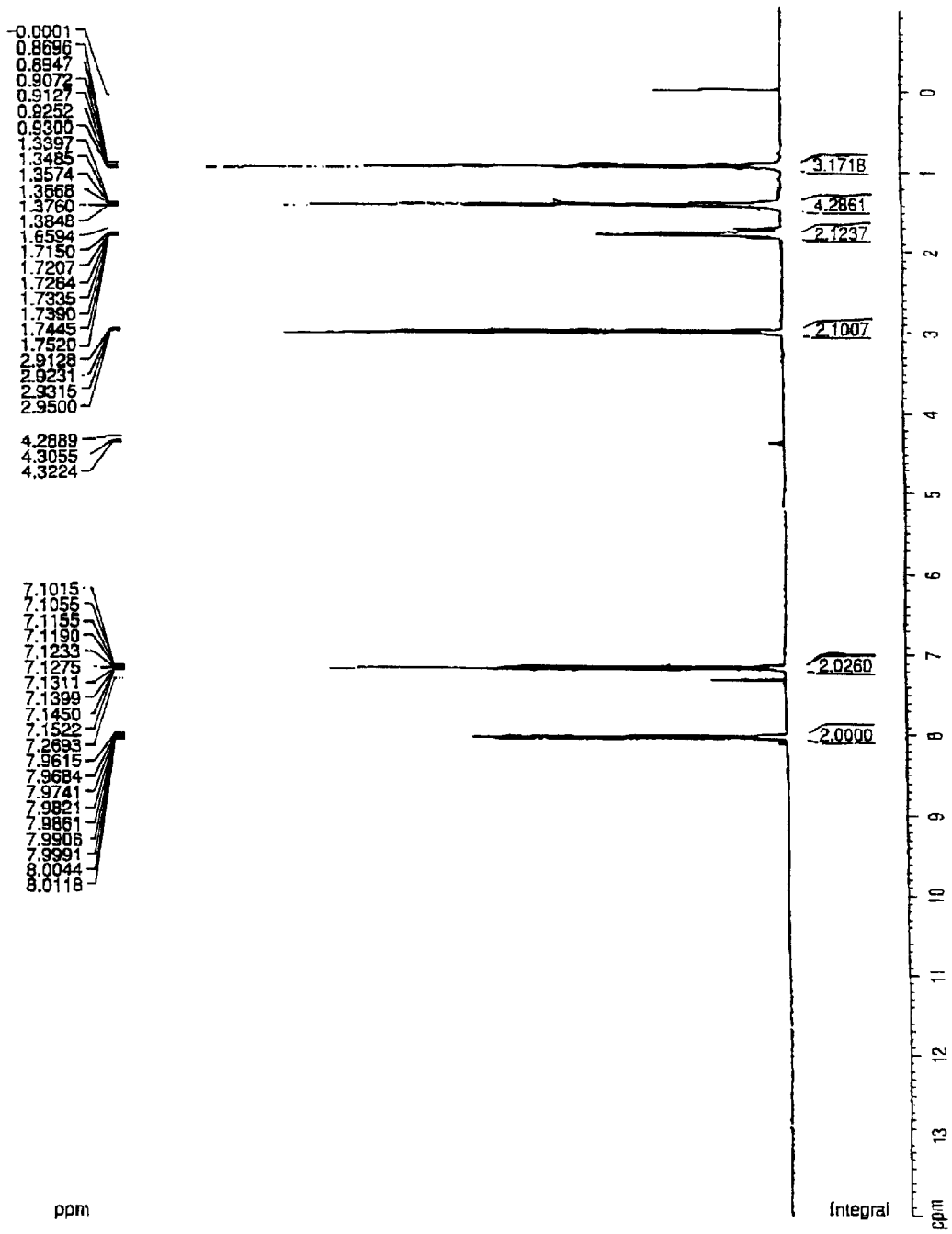
FIG. 7 shows a 1H-NMR spectrum chart In Example 15.

The compound obtained was analyzed with NMR in the following conditions.
<Measuring apparatus> FT-NMR: Bruker DPX 400
  Resonance frequency: 1H=400 MHZ
<Measuring apparatus> Measuring nuclide: 1H
  Solvent used: $CDCl_3$
  Reference: capillary-sealed TMS/$CDCl_3$ Measuring temperature: room temperature The 1H-NMR spectrum is shown in FIG. 7 and the assignment results (see chemical formula (33)) are shown in Table 23, respectively.

TABLE 23

| Chemical shift (ppm) | Integrated value | type | Position |
|---|---|---|---|
| 0.91 | 3 | m | a |
| 1.36 | 4 | m | b, c |
| 1.73 | 2 | m | d |
| 2.92 | 2 | quart | e |
| 7.13 | 2 | m | i, k |
| 7.99 | 2 | m | h, l |

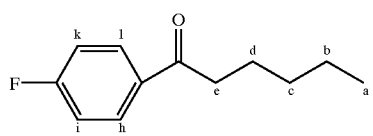

(33)

Figure 8:
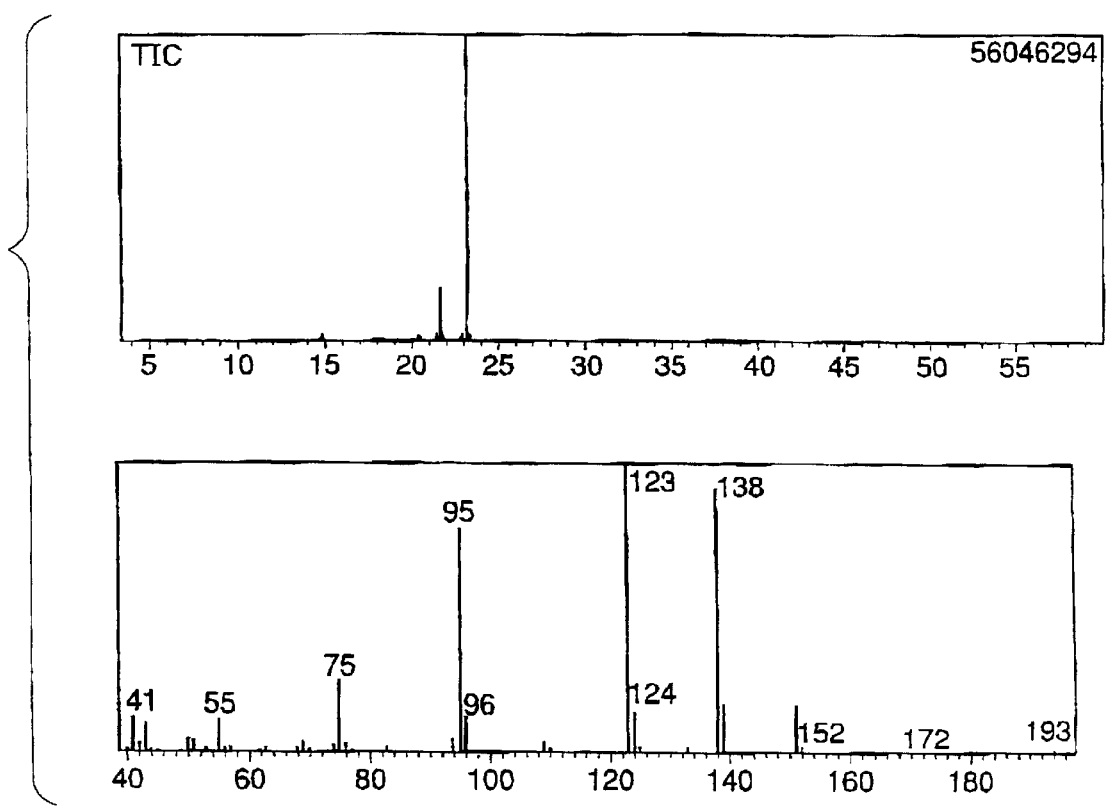
FIG. 8 shows a TIC and a mass spectrum of methyl 3-hydroxy-5-(4-fluorobenzoyl)valerate when PHA obtained in Example 15 was measured by GC-MS after methanolysis treatment.

The purified substance was analyzed using a gas chromatography-mass spectrometer (GC-MS, Shimadzu QP-5050, EI method) to be identified. The data of the GC-MS spectrum are shown in FIG. 8. As a result, the GC-MS TIC area ratio of FPHxO was 87%.

Example 16

The *Pseudomonas cichorii* YN2 strain was inoculated in 200 mL of the M9 medium containing 0.5% D-glucose and 0.05% FPHxO, then this was cultured with shaking at 125 strokes/min at 30° C. After 5 days, the bacteria were recovered by centrifugal separation, suspended with 10% sodium hypochlorite solution, shaken at 4° C. for 2 hours and the PHA was extracted. The precipitate from the extract was recovered by centrifugal separation, washed with water and then dried in vacuo to obtain the PHA.

The PHA obtained was analyzed using the NMR apparatus (FT-NMR Bruker DPX 400) in the following measuring conditions.

<Measuring condition> Measuring nuclide: 1H

Solvent used: CDCl$_3$ (capillary-sealed TMS/CDCl$_3$ used as reference)

Resonance frequency: 1H=400 MHz

Figure 9:
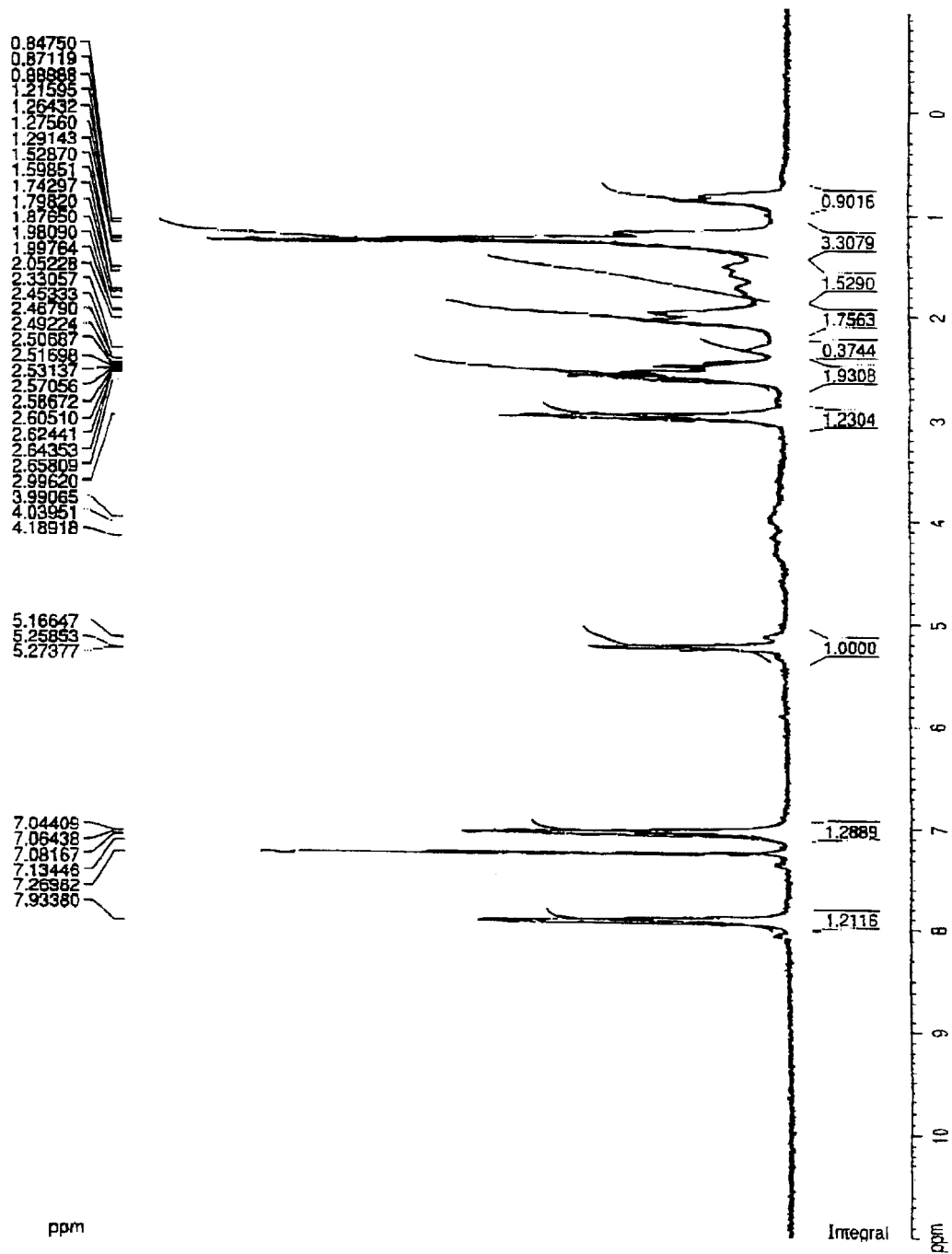
FIG. 9 shows a 1H-NMR spectrum chart in Example 16.

The 1H-NMR spectrum is shown in FIG. 9 and the assignment results (see chemical formula (34)) are shown in Table 24, respectively.

TABLE 24

| Chemical shift (ppm) | Integrated value | type | Position |
|---|---|---|---|
| 2.01–2.13 | 2 | m | d |
| 2.44–2.70 | 2 | m | b |
| 2.91–3.07 | 2 | m | e |
| 5.20–5.32 | 1 | m | c |
| 6.99–7.13 | 2 | m | i, k |
| 7.87–8.01 | 2 | m | h, l |

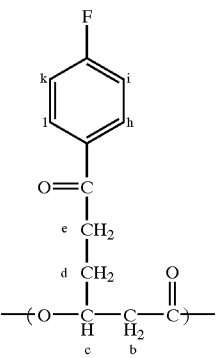

(34)

After methanolysis of the PHA obtained was performed according to the conventional method, the analysis by a gas chromatography-mass spectrometer (GC-MS, Shimadzu QP-5050, EI method) was carried out to identify the methyl-esterified form of the PHA monomer unit. Consequently, as shown in Table 25, the present PHA was identified to be the PHA comprising 3-hydroxy-5-(4-fluorobenzoyl)valeric acid (hereinafter cometimes abbreviated as 3HFBzV) as a monomer unit.

TABLE 25

| Production of Polyhydroxyalkanoate by YN2 Strain | |
|---|---|
| Polymer weight (mg/L) | 27 |
| Composition of monomer unit (TIC peak area ratio) | |
| 3-Hydroxybutyric acid | 2.7% |
| 3-Hydroxyhexanoic acid | 0.6% |
| 3-Hydroxyheptanoic acid | 0.1% |
| 3-Hydroxyoctanoic acid | 8.1% |
| 3-Hydroxynonanoic acid | 0.1% |
| 3-Hydroxydecanoic acid | 11.0% |
| 3-Hydroxydodecanoic acid | 5.1% |
| 3-Hydroxydodecenoic acid | 0.1% |
| 3-Hydroxytetradecanoic acid | 1.9% |
| 3-Hydroxy-5-(4-fluorobenzoyl)valeric acid | 70.4% |

The molecular weight of this PHA was evaluated by gel permeation chromatography (GPC; Tosoh HLC-8220, Column: Polymer Laboratory PL gel MIXED-C (5 μm), Solvent: chloroform, conversion to polystyrene). Consequently, this was Mn=26,000 and Mw=142,000.

Example 17

The *Pseudomonas cichorii* YN2 strain was inoculated in 200 mL of the M9 medium containing 0.5% D-glucose and 0.1% FPHxO, then this was cultured with shaking at 125 strokes/min at 30° C. After 48 hours, the bacteria were recovered by centrifugal separation, washed once with cold methanol and dried in vacuo.

This vacuum dried pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain the PHA.

After methanolysis of the PHA obtained was performed according to the conventional method, the analysis by a gas chromatography-mass spectrometer (GC-MS, Shimadzu QP-5050, EI method) was carried out to identify the methylesterified form of the PHA monomer unit. The results are shown in Table 26.

TABLE 26

Production of Polyhydroxyalkanoate by YN2 Strain

| | |
|---|---|
| Dry cell weight (mg/L) | 500 |
| Polymer weight (mg/L) | 7.5 |
| Composition of monomer unit (TIC peak area ratio) | |
| 3-Hydroxybutyric acid | 2.0% |
| 3-Hydroxyhexanoic acid | 0.4% |
| 3-Hydroxyoctanoic acid | 7.1% |
| 3-Hydroxydecanoic acid | 7.2% |
| 3-Hydroxydodecanoic acid | 2.3% |
| 3-Hydroxydodecenoic acid | 2.1% |
| 3-Hydroxytetradecanoic acid | 0.3% |
| 3-Hydroxy-5-(4-fluorobenzoyl)valeric acid | 78.6% |

From the above results, the present PHA was identified to be the PHA comprising 3HFBzV as a monomer unit.

Example 18

The *Pseudomonas cichorii* YN2 strain was inoculated in 200 mL of the M9 medium containing 0.5% sodium glutamate and 0.1% FPHxO, then this was cultured with shaking at 125 strokes/min at 30° C. After 7 days, the bacteria were recovered by centrifugal separation, washed once with cold methanol and dried in vacuo.

This vacuum dried pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried vacuo to obtain the PHA.

After methanolysis of the PHA obtained was performed according to the conventional method, the analysis by a gas chromatography-mass spectrometer (GC-MS, Shimadzu QP-5050, EI method) was carried out to identify the methyl-esterified form of the PHA monomer unit. The results are shown in Table 27.

TABLE 27

Production of Polyhydroxyalkanoate by YN2 Strain

| | |
|---|---|
| Dry cell weight (mg/L) | 490 |
| Polymer weight (mg/L) | 250 |
| Composition of monomer unit (TIC peak area ratio) | |
| 3-Hydroxybutyric acid | 56.8% |
| 3-Hydroxyvaleric acid | 0.6% |
| 3-Hydroxyhexanoic acid | 0.5% |
| 3-Hydroxyoctanoic acid | 7.2% |
| 3-Hydroxydecanoic acid | 7.1% |
| 3-Hydroxydodecanoic acid | 2.0% |
| 3-Hydroxydodecenoic acid | 1.8% |
| 3-Hydroxy-5-(4-fluorobenzoyl)valeric acid | 24.0% |

From the above results, the present PHA was identified to be the PHA comprising 3HFBzV as a monomer unit.

Example 19

The *Pseudomonas cichorii* YN2 strain was inoculated in 200 mL of the M9 medium containing 0.5% sodium glutamate and 0.1% FPHxO, then this was cultured with shaking at 125 strokes/min at 30° C. After 48 hours, the bacteria were recovered by centrifugal separation, washed once with cold methanol and dried in vacuo.

This vacuum dried pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain the PHA.

After methanolysis of the PHA obtained was performed according to the conventional method, the analysis by a gas chromatography-mass spectrometer (GC-MS, Shimadzu QP-5050, EI method) was carried out to identify the methyl-esterified form of the PHA monomer unit. The results are shown in Table 28.

TABLE 28

Production of Polyhydroxyalkanoate by YN2 Strain

| | |
|---|---|
| Dry cell weight (mg/L) | 410 |
| Polymer weight (mg/L) | 38 |
| Composition of monomer unit (TIC peak area ratio) | |
| 3-Hydroxybutyric acid | 17.4% |
| 3-Hydroxyvaleric acid | 0.8% |
| 3-Hydroxyhexanoic acid | 0.9% |
| 3-Hydxoxyheptanoic acid | 0.1% |
| 3-Hydroxyoctanoic acid | 12.9% |
| 3-Hydxoxynonanoic acid | 0.2% |
| 3-Hydroxydecanoic acid | 14.0% |
| 3-Hydroxydodecanoic acid | 5.1% |
| 3-Hydroxydodecenoic acid | 3.8% |
| 3-Hydroxytetradecanoic acid | 0.4% |
| 3-Hydroxy-5-(4-fluorobenzoyl)valeric acid | 44.4% |

From the above results, the present PHA was identified to be the PHA comprising 3HFBzV as a monomer unit.

Example 20

200 mL of the M9 medium containing 0.5% (w/v) polypeptone and 0.1% (v/v) n-phenoxyheptane was prepared, placed into a 500 mL volume shaking flask and sterilized by an autoclave.

The flask was returned to a room temperature and the *Pseudomonas cichorii* YN2 strain on the agar plate was inoculated, then this was cultured with shaking at 125 strokes/min at 30° C. After 120 hours, the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain 4 mg of the PHA.

The molecular weight of this PHA was evaluated by gel permeation chromatography (GPC; Tosoh HLC-8220, Column: Tosoh TSK-GEL Super HM-H, Solvent; chloroform, conversion to polystyrene). Consequently, this was Mn=52,000 and Mw=122,000.

After methanolysis of the PHA obtained was performed according to the conventional method, the analysis by a gas chromatography-mass spectrometer (GC-MS, Shimadzu QP-5050. EI method) was carried out to identify the methyl-esterified form of the PHA monomer unit. The results are shown in Table 29.

Consequently, as shown in Table 29, the present PHA was identified to be the PHA comprising 3-hydroxy-5-phenoxyvaleric acid and 3-hydroxy-7-phenoxyheptanoic acid as monomer units.

TABLE 29

Production of PHA Produced in Example 20 and Composition of Monomer Unit

| | |
| --- | --- |
| Dry cell weight | 620 mg/L |
| Dry polymer weight | 20 mg/L |
| Dry polymer weight/Dry cell weight | 3.2% |
| Composition of monomer unit (TIC peak area ratio) | |
| 3-Hydroxybutyric acid | 1.4% |
| 3-Hydroxyhexanoic acid | 0.0% |
| 3-Hydroxyoctanoic acid | 0.1% |
| 3-Hydroxydecanoic acid | 0.2% |
| 3-Hydroxydodecanoic acid | 0.0% |
| 3-Hydroxydodecenoic acid | 0.0% |
| 3-Hydroxy-5-phenoxyvaleric acid | 29.7% |
| 3-Hydroxy-7-phenoxyheptanoic acid | 68.6% |

Example 21

200 mL of the M9 medium containing 0.5% (w/v) glucose was prepared, placed into a 500 mL volume shaking flask and sterilized by an autoclave. The flask was returned to a room temperature and 5-(4-vinylphenyl)pentane sterilized by a filter was added with well stirring so that the concentration is adjusted to 0.1% (v/v), then the *Pseudomonas cichorii* YN2 strain was inoculated and cultured with shaking at 125 strokes/min at 30° C. After 120 hours, the bacteria were recovered by centrifugal separation.

Then, 200 mL of the M9 medium containing 0.5% (w/v) glucose but not containing $NH_4Cl$ as a nitrogen source was prepared, placed into a 500 mL volume shaking flask and sterilized by an autoclave. The flask was returned to a room temperature and 5-(4-vinylphenyl)pentane sterilized by a filter was added with well stirring so that the concentration is adjusted to 0.1% (v/v), then the recovered bacteria was resuspended in the medium and cultured with shaking at 125 strokes/min at 30° C. After 120 hours, the bacteria were recovered by centrifugal separation, washed once with cold methanol and lyophilized.

This lyophilized pellet was suspended in 20 mL of chloroform and stirred at 30° C. for 48 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain 3 mg of the PHA.

The molecular weight of this PHA obtained was obtained by performing the GPC analysis using the method similar to Example 10. Consequently, this was Mn=12,000 and Mw=21,000. When performing the 1H-NMR analysis of the PHA obtained using the method similar to Example 10, it was confirmed to be the PHA containing 97% 3-hydroxy-5-(4-vinylphenyl)valeric acid unit and 3-hydroxybutyric acid as the other unit.

Example 22

200 mL of the M9 medium containing 0.5% (w/v) polypeptone was prepared, placed into a 500 mL volume shaking flask and sterilized by an autoclave. The flask was returned to a room temperature and 5-(4-vinylphenyl) pentane sterilized by a filter was added with well stirring so that the concentration is adjusted to 0.1% (v/v), then the *Pseudomonas cichorii* YN2 strain was inoculated and cultured with shaking at 125 strokes/min at 30° C. After 120 hours, the bacteria were recovered by centrifugal separation.

Then, 200 mL of the M9 medium containing 0.5% (w/v) sodium pyruvate but not containing $NH_4Cl$ as a nitrogen source was prepared, placed into a 500 mL volume shaking flask and sterilized by an autoclave. The flask was returned to a room temperature and 5-(4-vinylphenyl)pentane sterilized by a filter was added with well stirring so that the concentration is adjusted to 0.1% (v/v), then the recovered bacteria was resuspended in the medium and cultured with shaking at 125 strokes/min at 30° C. After 120 hours, the bacteria were recovered by centrifugal separation, washed once with cold methanol and lyophilized.

This lyophilized pellet was suspended in 20 mL of chloroform and stirred at 30° C. for 48 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain 5 mg of the PHA.

The molecular weight of this PHA obtained was obtained by performing the GPC analysis using the method similar to Example 10. Consequently, this was Mn=8,000 and Mw=16,000. When performing the 1H-NMR analysis of the PHA obtained using the method similar to Example 10, it was confirmed to be the PHA containing 99% 3-hydroxy-5-(4-vinylphenyl)valeric acid unit and 3-hydroxybutyric acid as the other unit.

Example 23

200 mL of the M9 medium containing 0.5% (w/v) sodium malate and 0.1% (v/v) n-phenoxypentane was prepared, placed into a 500 mL volume shaking flask and sterilized by an autoclave.

The flask was returned to a room temperature and the *Pseudomonas cichorii* YN2 strain on the agar plate was inoculated, then this was cultured with shaking at 125 strokes/min at 30° C. After 120 hours, the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain 26 mg of the PHA.

The molecular weight of this PHA was evaluated by gel permeation chromatography (GPC; Tosoh HLC-8220, Column; Tosoh TSK-GEL Super HM-H, Solvent; chloroform, conversion to polystyrene). Consequently, this was Mn=66,000 and Mw=142,000.

After methanolysis of the PHA obtained was performed according to the conventional method, the analysis by a gas chromatography-mass spectrometer (GC-MS, Shimadzu QP-5050, EI method) was carried out to identify the methyl-esterified form of the PHA monomer unit. The results are shown in Table 30.

Consequently, as shown in Table 30, the present PHA was identified to be the PHA comprising 3-hydroxy-5-phenoxyvaleric as a monomer unit.

TABLE 30

Production of PHA Produced in Example 23 and
Composition of Monomer Unit

| | |
|---|---|
| Dry cell weight | 610 mg/L |
| Dry polymer weight | 130 mg/L |
| Dry polymer weight/Dry cell weight | 21.3% |
| Composition of monomer unit (peak area ratio) | |
| 3-Hydroxybutyric acid | 14.6% |
| 3-Hydroxyvaleric acid | 0.1% |
| 3-Hydroxyhexanoic acid | 0.2% |
| 3-Hydroxyoctanoic acid | 1.1% |
| 3-Hydroxydecanoic acid | 0.2% |
| 3-Hydroxydodecanoic acid | 1.0% |
| 3-Hydroxydodecenoic acid | 1.2% |
| 3-Hydroxy-5-phenoxyvaleric acid | 81.6% |

Example 24

200 mL of the M9 medium containing 0.1% (v/v) n-nonanoic acid and 0.1% (v/v) n-phenoxypentane was prepared, placed into a 500 mL volume shaking flask and sterilized by an autoclave.

The flask was returned to a room temperature and the *Pseudomonas cichorii* YN2 strain on the agar plate was inoculated, then this was cultured with shaking at 125 strokes/min at 30° C. After 120 hours, the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain 13 mg of the PHA.

The molecular weight of this PHA was evaluated by gel permeation chromatography (GPC: Tosoh HLC-8220, Column; Tosoh TSK-GEL Super HM-H, Solvent; chloroform, conversion to polystyrene). Consequently, this was Mn=51,000 and Mw=130,000.

After methanolysis of the PHA obtained was performed according to the conventional method, the analysis by a gas chromatography-mass spectrometer (GC-MS, Shimadzu QP-5050, EI method) was carried out to identify the methyl-esterified form of the PHA monomer unit. The results are shown in Table 31.

Consequently, as shown in Table 31, the present PHA was identified to be the PHA comprising 3-hydroxy-5-phenoxyvaleric acid an a monomer unit.

TABLE 31

Production of PHA Produced in Example 24 and
Composition of Monomer Unit

| | |
|---|---|
| Dry cell weight | 370 mg/L |
| Dry polymer weight | 65 mg/L |
| Dry polymer weight/Dry cell weight | 17.5% |
| Composition of monomer unit (peak area ratio) | |
| 3-Hydroxybutyric acid | 0.6% |
| 3-Hydroxyvaleric acid | 0.0% |
| 3-Hydroxyhexanoic acid | 0.2% |
| 3-Hydroxyheptanoic acid | 12.4% |

TABLE 31-continued

Production of PHA Produced in Example 24 and
Composition of Monomer Unit

| | |
|---|---|
| 3-Hydroxyoctanoic acid | 6.1% |
| 3-Hydroxynonanoic acid | 59.1% |
| 3-Hydroxydecanoic acid | 0.2% |
| 3-Hydroxydodecanoic acid | 1.0% |
| 3-Hydroxydodecenoic acid | 1.0% |
| 3-Hydroxy-5-phenoxyvaleric acid | 19.4% |

Example 25

200 mL of the M9 medium containing 0.5% (w/v) glucose was prepared, placed into 500 mL volume shaking flask and sterilized by autoclave. The flask was returned to a room temperature and n-amylbenzene sterilized by a filter was added with well stirring so that the concentration is adjusted to 0.1% (v/v), then the *Pseudomonas cichorii* YN2 strain was inoculated and cultured with shaking at 125 stroke/min at 30° C. After 90 hours, the bacteria were recovered by centrifugal separation, washed and lyophilized.

This lyophilized pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain 77 mg of the PHA.

The molecular weight of this PHA obtained by performing the GPR analysis using the method similar to Example 16. Consequently, this was Mn=51000, Mw=102000. When performing the 1H-NMR analysis of the PHA obtained using the method similar to Example 16, it was confirmed to be the PHA containing 71% 3-hydroxy-5-phenylvaleric acid unit and saturated or unsaturated 4 to 12 carbon length 3-hydroxyalkanoic acids as the other unit.

Example 26

200 mL of the M9 medium containing 0.5% (w/v) glucose was prepared, placed into 500 mL volume shaking flask and sterilized by autoclave. The flask was returned to a room temperature and n-amylbenzene sterilized by a filter was added with well stirring so that the concentration is adjusted to 0.1% (v/v), then the *Pseudomonas cichorii* YN2 strain was inoculated and cultured with shaking at 125 stroke/min at 30° C. After 90 hours, the bacteria were recovered by centrifugal separation.

Then, 200 mL of the M9 medium containing 0.5% (w/v) glucose but not containing $NH_4Cl$ as a nitrogen source was prepared, placed into 500 mL volume shaking flask and sterilized by autoclave. The flask was returned to a room temperature and n-amylbenzene sterilized by a filter was added with well stirring so that the concentration is adjusted to 0.1% (v/v), then the recovered bacteria was resuspended in the medium and cultured with shaking at 125 stroke/min at 30° C. After 90 hours the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain 92 mg of the PHA.

The molecular weight of this PHA obtained by performing the GPR analysis using the method similar to Example 16. Consequently, this was Mn=49000, Mw=103000. When performing the 1H-NMR analysis of the PHA obtained using the method similar to Example 16, it was confirmed to be the PHA containing 66% 3-hydroxy-5-phenylvaleric acid unit and saturated or unsaturated 4 to 12 carbon length 3-hydroxyalkanoic acids as the other unit.

Example 27

200 mL of the M9 medium containing 0.5% (w/v) glucose was prepared, placed into 500 mL volume shaking flask and sterilized by autoclave. The flask was returned to a room temperature and n-amylbenzene sterilized by a filter was added with well stirring so that the concentration is adjusted to 0.1%(v/v), then the *Pseudomonas cichorii* YN2 strain was inoculated and cultured with shaking at 125 stroke/min at 30° C. After 90 hours, the bacteria were recovered by centrifugal separation.

Then, 200 mL of the M9 medium containing 0.5% (w/v) glucose was prepared, placed into 500 mL volume shaking flask and sterilized by autoclave. The flask was returned to a room temperature and n-amylbenzene sterilized by a filter was added with well stirring so that the concentration is adjusted to 0.1% (v/v), then the recovered bacteria was resuspended in the medium and cultured with shaking at 125 stroke/min at 30° C. After 90 hours, the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain 145 mg of the PHA.

The molecular weight of this PHA obtained by performing the GPR analysis using the method similar to Example 16. Consequently, this was Mn=48000, Mw=96000. When performing the 1H-NMR analysis of the PHA obtained using the method similar to Example 16, it was confirmed to be the PHA containing 72% 3-hydroxy-5-phenylvaleric acid unit and saturated or unsaturated 4 to 12 carbon length 3-hydroxyalkanoic acids as the other unit.

Example 28

200 mL of the M9 medium containing 0.5% (w/v) glucose was prepared, placed into 500 mL volume shaking flask and sterilized by autoclave. The flask was returned to a room temperature and n-amylbenzene sterilized by a filter was added with well stirring so that the concentration is adjusted to 0.1% (v/v), then the *Pseudomonas cichorii* YN2 strain was inoculated and cultured with shaking at 125 stroke/min at 30° C. After 90 hours, the bacteria were recovered by centrifugal separation.

Then, 200 mL of the M9 medium but not containing NH$_4$Cl as a nitrogen source was prepared, placed into 500 mL volume shaking flask and sterilized by autoclave. The flask was returned to a room temperature and n-amylbenzene sterilized by a filter was added with well stirring so that the concentration is adjusted to 0.1% (v/v), then the recovered bacteria was resuspended in the medium and cultured with shaking at 125 stroke/min at 30° C. After 90 hours, the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried vacuo to obtain 64 mg of the PHA.

The molecular weight of this PHA obtained by performing the GPR analysis using the method similar to Example 16. Consequently, this was Mn=52000, Mw=99000. When performing the 1H-NMR analysis of the PHA obtained using the method similar to Example 16, it was confirmed to be the PHA containing 73% 3-hydroxy-5-phenylvaleric acid unit and saturated or unsaturated 4 to 12 carbon length 3-hydroxyalkanoic acids as the other unit.

Example 29

200 mL of the M9 medium containing 0.5% (w/v) polypeptone was prepared, placed into 500 mL volume shaking flask and sterilized by autoclave. The flask was returned to a room temperature and n-amylbenzene sterilized by a filter was added with well stirring so that the concentration is adjusted to 0.1% (v/v), then the *Pseudomonas cichorii* YN2 strain was inoculated and cultured with shaking at 125 stroke/min at 30° C. After 48 hours, the bacteria were recovered by centrifugal separation.

Then, 200 mL of the M9 medium containing 0.5% (w/v) glucose but not containing NH$_4$Cl as a nitrogen source was prepared, placed into 500 mL volume shaking flask and sterilized by autoclave. The flask was returned to a room temperature and n-amylbenzene sterilized by a filter was added with well stirring so that the concentration is adjusted to 0.1% (v/v), then the recovered bacteria was resuspended in the medium and cultured with shaking at 125 stroke/min at 30° C. After 90 hours, the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain 155 mg of the PHA.

The molecular weight of this PHA obtained by performing the GPR analysis using the method similar to Example 16. Consequently, this was Mn=48000, Mw=101000. When performing the 1H-NMR analysis of the PHA obtained using the method similar to Example 16, it was confirmed to be the PHA containing 78% 3-hydroxy-5-phenylvaleric acid unit and saturated or unsaturated 4 to 12 carbon length 3-hydroxyalkanoic acids as the other unit.

Example 30

200 mL of the M9 medium containing 0.5% (w/v) polypeptone was prepared, placed into 500 mL volume shaking flask and sterilized by autoclave. The flask was returned to a room temperature and n-amylbenzene sterilized by a filter, was added with well stirring so that the concentration is adjusted to 0.1% (v/v), then the *Pseudomonas cichorii* YN2 strain was inoculated and cultured with shaking at 125 stroke/min at 30° C. After 48 hours, the bacteria were recovered by centrifugal separation.

Then, 200 mL of the M9 medium containing 0.5% (w/v) glucose was prepared, placed into 500 mL volume shaking flask and sterilized by autoclave. The flask was returned to a room temperature and n-amylbenzene sterilized by a filter was added with well stirring so that the concentration is adjusted to 0.1% (v/v), then the recovered bacteria was resuspended in the medium and cultured with shaking at 125 stroke/min at 30° C. After 90 hours, the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain 110 mg of the PHA.

The molecular weight of this PHA obtained by performing the GPR analysis using the method similar to Example 16. Consequently, this was Mn=46000, Mw=97000. When performing the 1H-NMR analysis of the PHA obtained using the method similar to Example 16, it was confirmed to be the PHA containing 91% 3-hydroxy-5-phenylvaleric acid unit and saturated or unsaturated 4 to 12 carbon length 3-hydroxyalkanoic acids as the other unit.

Example 31

200 mL of the M9 medium containing 0.5% (w/v) polypeptone was prepared, placed into 500 mL volume shaking flask and sterilized by autoclave. The flask was returned to a room temperature and n-amylbenzene sterilized by a filter was added with well stirring so that the concentration is adjusted to 0.1% (v/v), then the *Pseudomonas cichorii* YN2 strain was inoculated and cultured with shaking at 125 stroke/min at 30° C. After 48 hours, the bacteria were recovered by centrifugal separation.

Then, 200 mL of the M9 medium but not containing NH$_4$Cl as a nitrogen source was prepared, placed into 500 mL volume shaking flask and sterilized by autoclave. The flask was returned to a room temperature and n-amylvenzene sterilized by a filter was added with well stirring so that the concentration is adjusted to 0.1% (v/v), then the recovered bacteria was resuspended in the medium and cultured with shaking at 125 stroke/min at 30° C. After 90 hours, the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain 41 mg of the PHA.

The molecular weight of this PHA obtained by performing the GPR analysis using the method similar to Example 16. Consequently, this was Mn=44000, Mw=88000. When performing the 1H-NMR analysis of the PHA obtained using the method similar to Example 16, it was confirmed to be the PHA containing 95% 3-hydroxy-5-phenylvaleric acid unit and saturated or unsaturated 4 to 12 carbon length 3-hydroxyalkanoic acids as the other unit.

Example 32

YN2 colonies on M9 medium plate containing 0.1% nonanate were suspended in sterilized physiological saline so that the turbidity at 600 nm is adjusted to 0.1. Forty M9 medium plates without carbon source were prepared, the suspension was applied to the plates and cultured at 30° C. in nonane atmosphere. After 48 hours, the bacteria were recovered and suspended in 2 mL of physiological saline.

Then, 200 mL of the M9 medium containing 0.5 (w/v) glucose but not containing NH$_4$Cl as a nitrogen source was prepared, placed into 500 mL volume shaking flask and sterilized by autoclave. The flask was returned to a room temperature and n-amylbenzene sterilized by a filter was added with well stirring so that the concentration is adjusted to 0.1% (v/v), then the recovered bacteria was resuspended in the medium and cultured with shaking at 125 stroke/min at 30° C. After 90 hours, the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain 9 mg of the PHA.

When performing the 1H-NMR analysis of the PHA obtained using the method similar to Example 16, it was confirmed to be the PHA containing 45% 3-hydroxy-5-phenylvaleric acid unit and saturated or unsaturated 4 to 12 carbon length 3-hydroxyalkanoic acids as the other unit.

Example 33

YN2 colonies on M9 medium plate containing 0.1% nonanate were suspended in sterilized physiological saline so that the turbidity at 600 nm is adjusted to 0.1. Forty M9 medium plates without carbon source were prepared, the suspension was applied to the plates and cultured at 30° C. in nonane atmosphere. After 48 hours, the bacteria were recovered and suspended in 2 mL of physiological saline.

Then, 200 mL of the M9 medium containing 0.5% (w/v) glucose was prepared, placed into 500 mL volume shaking flask and sterilized by autoclave. The flask was returned to a room temperature and n-amylbenzene sterilized by a filter was added with well stirring so that the concentration is adjusted to 0.1% (v/v), then the recovered bacteria was resuspended in the medium and cultured with shaking at 125 stroke/min at 30° C. After 90 hours, the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain 83 mg of the PHA.

When performing the 1H-NMR analysis of the PHA obtained using the method similar to Example 16, it was confirmed to be the PHA containing 13% 3-hydroxy-5-phenylvaleric acid unit and saturated or unsaturated 4 to 12 carbon length 3-hydroxyalkanoic acids as the other unit.

Example 34

200 mL of the M9 medium containing 0.5% (w/v) glucose was prepared, placed into 500 mL volume shaking flask and sterilized by autoclave. The flask was returned to a room temperature and n-hexanophenon sterilized by a filter was added with well stirring so that the concentration is adjusted to 0.1% (v/v), then the *Pseudomonas cichorii* YN2 strain was inoculated and cultured with shaking at 125 stroke/min at 30° C. After 90 hours, the bacteria were recovered by centrifugal separation.

Then, 200 mL of the M9 medium containing 0.5% (w/v) glucose but not containing $NH_4Cl$ as a nitrogen source was prepared, placed into 500 mL volume shaking flask and sterilized by autoclave. The flask was returned to a room temperature and n-hexanophenon sterilized by a filter was added with well stirring so that the concentration is adjusted to 0.1% (v/v), then the recovered bacteria was resuspended in the medium and cultured with shaking at 125 stroke/min at 30° C. After 90 hours, the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain 51 mg of the PHA.

The molecular weight of this PHA obtained by performing the GPR analysis using the method similar to Example 16. Consequently, this was Mn=88000, Mw=23000. When performing the 1H-NMR analysis of the PHA obtained using the method similar to Example 16, it was confirmed to be the PHA containing 38% 3-hydroxy-5-benzoylvaleric acid unit and saturated or unsaturated 4 to 12 carbon length 3-hydroxyalkanoic acids as the other unit.

Example 35

200 mL of the M9 medium containing 0.5% (w/v) glucose was prepared, placed into 500 mL volume shaking flask and sterilized by autoclave. The flask was returned to a room temperature and n-hexanophenon sterilized by a filter was added with well stirring so that the concentration is adjusted to 0.1% (v/v), then the *Pseudomonas cichorii* YN2 strain was inoculated and cultured with shaking at 125 stroke/min at 30° C. After 90 hours, the bacteria were recovered by centrifugal separation.

Then, 200 mL of the M9 medium containing 0.5% (w/v) glucose was prepared, placed into 500 mL volume shaking flask and sterilized by autoclave. The flask was returned to a room temperature and n-hexanophenon sterilized by a filter was added with well stirring so that the concentration is adjusted to 0.1% (v/v), then the recovered bacteria was resuspended in the medium and cultured with shaking at 125 stroke/min at 30° C. After 90 hours, the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain 44 mg of the PHA.

The molecular weight of this PHA obtained by performing the GPR analysis using the method similar to Example 16. Consequently, this was Mn=107000, Mw=203000. When performing the 1H-NMR analysis of the PHA obtained using the method similar to Example 16, it was confirmed to be the PHA containing 32% 3-hydroxy-5-benzoylvaleric acid unit and saturated or unsaturated 4 to 12 carbon length 3-hydroxyalkanoic acids as the other unit.

Example 36

200 mL of the M9 medium containing 0.5% (w/v) glucose was prepared, placed into 500 mL volume shaking flask and sterilized by autoclave. The flask was returned to a room temperature and n-phenoxypentane sterilized by a filter was added with well stirring so that the concentration is adjusted to 0.1% (v/v), then the *Pseudomonas cichorii* YN2 strain was inoculated and cultured with shaking at 125 stroke/min at 30° C. After 90 hours, the bacteria were recovered by centrifugal separation.

Then, 200 mL of the M9 medium containing 0.5% (w/v) glucose but not containing $NH_4Cl$ as a nitrogen source was prepared, placed into 500 mL volume shaking flask and sterilized by autoclave. The flask was returned to a room temperature and n-phenoxypentane sterilized by a filter was added with well stirring so that the concentration is adjusted to 0.1% (v/v), then the recovered bacteria was resuspended in the medium and cultured with shaking at 125 stroke/min at 30° C. After 90 hours, the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain 54 mg of the PHA.

The molecule weight of this PHA obtained by performing the GPR analysis using the method similar to Example 16. Consequently, this was Mn=72000, Mw=158000. When performing the 1H-NMR analysis of the PHA obtained using the method similar to Example 16, it was confirmed to be the PHA containing 60% 3-hydroxy-5-phenoxyvaleric acid unit and saturated or unsaturated 4 to 12 carbon length 3-hydroxyalkanoic acids as the other unit.

Example 37

200 mL of the M9 medium containing 0.5% (w/v) glucose was prepared, placed into 500 mL volume shaking flask and sterilized by autoclave. The flask was returned to a room temperature and n-phenoxypentane sterilized by a filter was added with well stirring so that the concentration is adjusted to 0.1% (v/v), then the *Pseudomonas cichorii* YN2 strain was inoculated and cultured with shaking at 125 stroke/min at 30° C. After 90 hours, the bacteria were recovered by centrifugal separation.

Then, 200 mL of the M9 medium containing 0.5% (w/v) glucose was prepared, placed into 500 mL volume shaking flask and sterilized by autoclave. The flask was returned to a room temperature and n-phenoxypentane sterilized by a filter was added with well stirring so that the concentration is adjusted to 0.1% (v/v), then the recovered bacteria was resuspended in the medium and cultured with shaking at 125 stroke/min at 30° C. After 90 hours, the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain 42 mg of the PHA.

The molecular weight of this PHA obtained by performing the GPR analysis using the method similar to Example 16. Consequently, this was Mn=78000, Mw=156000. When performing the 1H-NMR analysis of the PHA obtained using the method similar to Example 16, it was confirmed to be the PHA containing 60% 3-hydroxy-5-phenoxyvaleric acid unit and saturated or unsaturated 4 to 12 carbon length 3-hydroxyalkanoic acids as the other unit.

Example 38

200 mL of the M9 medium containing 0.5% (w/v) glucose was prepared, placed onto 500 mL volume shaking flask and sterilized by autoclave. The flask was returned to a room temperature and n-amylbenzene sterilized by a filter was added with well stirring so that the concentration is adjusted to 0.1% (v/v), then the *Pseudomonas cichorii* YN2 strain was inoculated and cultured with shaking at 125 stroke/min at 30° C. When turbidity at 600 nm became 0.1, dicyclopropylketone was added with well stirring so that the concentration is adjusted to 0.05% (v/v) and continued shake culturing. After 90 hours, the bacteria were recovered by centrifugal separation, washed and lyophilized This lyophilized pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain 54 mg of the PHA.

The molecular weight of this PHA obtained by performing the GPR analysis using the method similar to Example 16. Consequently, this was Mn=30000, Mw=63000. When performing the 1H-NMR analysis of the PHA obtained using the method similar to Example 16, it was confirmed to be the PHA containing 37% 3-hydroxy-5-phenylvaleric acid unit and saturated or unsaturated 4 to 12 carbon length 3-hydroxyalkanoic acids as the other unit.

Example 39

200 mL of the M9 meduim containing 0.5% (w/v) polypeptone was prepared, place into 500 mL volume shaking flask and sterilized by autoclave. The flask was returned to a room temperature and n-amylbenzene sterilized by a filter was added with well stirring so that the concentration is adjusted to 0.1% (v/v), then the *Pseudomonas cichorii* YN2 strain was inoculated and cultured with shaking at 125 stroke/min at 30° C. When turbidity at 600 nm became 0.1, dicyclopropylketone was added with well stirring so that the concentration is adjusted to 0.05% (v/v) and continued shake culturing. After 48 hours, the bacteria were recovered by centrifugal separation, washed and lyophilized.

This lyophilized pellet was suspended in 20 mL of chloroform and stirred at 60° C. for 20 hours to extract PHA. After the extract was filtered through a membrance filter with the pore size of 0.45 μm, the filtrate was concentrated using a rotary evaporator, the concentrate was reprecipitated in cold methanol, further only the precipitate was recovered and dried in vacuo to obtain 67 mg of the PHA.

The molecular weight of this PHA obtained by performing the GPR analysis using the method similar to Example 16. Consequently, this was Mn=30000, Mw=66000. When performing the 1H-NMR analysis of the PHA obtained using the method similar to Example 16, it was confirmed to be the PHA containing 79% 3-hydroxy-5-phenylvaleric acid unit and 3-hydroxybutyric acid as the other unit.

Example 40

200 mL of the M9 medium containing 0.5% (w/v) glucose was prepared, placed into 500 mL volume shaking flask and sterilized by autoclave. The flask was returned to a room temperature and n-amylbenzene sterilized by a filter was added with well stirring so that the concentration is adjusted to 0.1% (v/v), then the *Pseudomonas cichorii* YN2 strain was inoculated and cultured with shaking at 125 stroke/min at 30° C. When turbidity at 600 nm became 0.1. dicyclopropylketone was added with well stirring so that the concentration is adjusted to 0.05% (v/v), then the shake culturing was continued. After 14 hours, the bacteria were recovered by centrifugal separation.

Then, 200 mL of the M9 meduim containing 0.5% (w/v) glucose but not containing NH$_4$Cl as a nitrogen source was prepared, placed into 500 mL volume shaking flask and sterilized by autoclave. The flask was returned to a room temperature and n-amylbenzene sterilized by a filter was added with well stirring so that the concentration is adjusted to 0.1% (v/v), then the recovered bacteria was resuspended in the medium and cultured with shaking at 125 stroke/min at 30° C. After 90 hours the bacteria were recovered by centrifugal separation, washed once with cold methanol and lyophilezed.

This lyophilized pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain 12 mg of the PHA.

The molecular weight of this PHA obtained by performing the GPR analysis using the method similar to Example 16. Consequently, this was Mn=50000, Mw=110000. When performing the 1H-NMR analysis of the PHA obtained using the method similar to Example 16, it was confirmed to be the PHA containing 86% 3-hydroxy-5-phenylvaleric acid unit and saturated or unsaturated 4 to 12 length 3-hydroxyalkanoic acids as the other unit.

Example 41

200 mL of the M9 medium containing 0.5% (w/v) glucose was prepared, placed into 500 mL volume shaking flask and sterilized by autoclave. The flask was returned to a room temperature and n-amylbenzene sterilized by a filter was added with well stirring so that the concentration is adjusted 0.1% (v/v), then the *Pseudomonas cichorii* YN2 strain was inoculated and cultured with shaking at 125 stroke/min at 30° C. When turbidity at 600 nm became 0.1, dicyclopropylketone was added with well stirring so that the concentration is adjusted to 0.05% (v/v), then the shake culturing was continued. After 14 hours, the bacteria were recovered by centrifugal separation.

Then, 200 mL of the M9 medium containing 0.5% (w/v) glucose was prepared, placed into 500 mL volume shaking flask and sterilized by autoclave. The flask was returned to a room temperature and n-amylbenzene sterilized by a filter was added with well stirring so that the concentration is adjusted to 0.1% (v/v), then the recovered bacteria was resuspended in the medium and cultured with shaking at 125 stroke/min at 30° C. After 90 hours, the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membace filter with the pore size of 0.45 μm, the filtrate was concentrated using a rotary evaporator, the concentrate was reprecipitated in cold methanol further only the precipitate was recovered and dried in vacuo to obtain 87 mg of the PHA.

The molecular weight of this PHA obtained by performing the GPR analysts using the method similar to Example 16. Consequently, this was Mn=53000, Mw=106000. When performing the 1H-NMR analysis of the PHA obtained using the method similar to Example 16, it was confirmed to be the PHA containing 86% 3-hydroxy-5-phenylvaleric acid unit and saturated or unsaturated 4 to 12 carbon length 3-hydroxyalkanoic acids as the other unit.

Example 42

200 mL of the M9 medium containing 0.5% (w/v) polypeptone was prepared, placed into 500 mL volume shaking flask and strilized by autoclave. The flask was returned to a room temperature and n-amylbenzene sterilized by a filter was added with well stirring so that the concentration is adjusted to 0.1% (v/v), then the *Pseudomonas cichorii* YN2 strain was inoculated and cultured with shaking at 125 stroke/min at 30° C. When turbidity at 600 nm became 0.1, dicyclopropylketone was added with well stirring so that the concentration is adjusted to 0.05% (v/v), then the shake culturing was continued. After 14 hours, the bacteria were recovered by centrifugal separation.

Then, 200 mL of the M9 medium containing 0.5% (w/v) glucose but not containing $NH_4Cl$ as a nitrogen source was prepared, placed into 500 mL volume shaking flask and sterilized by autoclave. Then flask was returned to a room temperature and n-amylbenzene sterilized by a filter was added with well stirring so that the concentration is adjusted to 0.1% (v/v), then the recovered bacteria was resuspended in the medium and cultured with shaking at 125 stroke/min at 30° C. After 90 hours, the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain 150 mg of the PHA.

The molecular weight of this PHA obtained by performing the GPR analysis using the method similar to Example 16. Consequently, this was Mn=66000, Mw=145000. When performing the 1H-NMR analysis of the PHA obtained using the method similar to Example 16, it was confirmed to be the PHA containing 83% 3-hydroxy-5-phenylvaleric acid unit and saturated or unsaturated 4 to 12 carbon length 3-hydroxyalkanoic acids as the other unit.

Example 43

200 mL of the M9 medium containing 0.5% (w/v) polypeptone was prepared, placed into 500 mL volume shaking flask and sterilized by autoclave. The flask was returned to a room temperature and n-amylbenzene sterilized by a filter was added with well stirring so that the concentration is adjusted to 0.1% (v/v), then the *Pseudomonas cichorii* YN2 strain was inoculated and cultured with shaking at 125 stroke/min at 30° C. When turbidity at 600 nm became 0.1, dicyclopropylketone was added with well stirring so that the concentration is adjusted to 0.05% (v/v), then the shake culturing was continued. After 14 hours, the bacteria were recovered by centrifugal separation.

Then 200 mL of the M9 medium containing 0.5% (w/v) glucose was prepared, placed into 500 mL volume shaking flask and sterilized by autoclave. The flask was returned to a room temperature and n-amylvenzene sterilized by a filter was added with well stirring so that the concentration is adjusted to 0.1% (v/v), then the recovered bacteria was resuspended in the medium and cultured with shaking at 125 stroke/min at 30° C. After 90 hours, the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membrane filter with the pore size of 0.45 μm, the filtrate was concentrated using a rotary evaporator; the concentrate was reprecipitated in cold methanol, further only the precipitate was recovered and dried in vacuo to obtain 120 mg of the PHA.

The molecular weight of this PHA obtained by performing the GPR analysis using the method similar to Example 16. Consequently, this was Mn=56000, Mw=112000. When performing the 1H-NMR analysis of the PHA obtained using the method similar to Example 16, it was confirmed to be the PHA containing 91% 3-hydroxy-5-phenylvaleric acid unit and saturated or unsaturated 4 to 12 carbon length 3-hydroxyalkanoic acids as the other unit.

Example 44

200 mL of the M9 medium containing 0.5% (w/v) glucose was prepared, placed into 500 mL volume shaking flask and sterilized by autoclave. The flask was returned to a room temperature and the *Pseudomonas cichorii* YN2 strain was inoculated and cultured with shaking at 125 stroke/min at 30° C. When turbidity at 600 nm became 0.1, dicyclopropylketone was added with well stirring so that the concentration is adjusted to 0.05% (v/v), then the shake culturing was continued. After 14 hours, the bacteria were recovered by centrifugal separation.

Then, 200 mL of the M9 medium containing 0.5% (w/v) glucose but not containing $HN_4Cl$ as a nitrogen source was prepared, placed into 500 mL volume shaking flask and sterilized by autoclave. The flask was returned to a room temperature and n-anylbenzene sterilized by a filter was added with well stirring so that the concentration is adjusted to 0.1% (v/v), then the recovered bacteria was resuspended in the medium and cultured with shaking at 125 stroke/min at 30° C. After 90 hours, the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain 12 mg of the PHA.

The molecular weight of this PHA obtained by performing the GPR analysis using the method similar to Example 16. Consequently, this was Mn=44000, Mw=119000. When performing the 1H-NMR analysis of the PHA obtained using the method similar to Example 16, it was confirmed to be the PHA containing 87% 3-hydroxy-5-phenylvaleric acid unit and saturated or unsaturated 4 to 12 carbon length 3-hydroxyalkanoic acids as the other unit.

Example 45

200 mL of the M9 medium containing 0.5% (w/v) glucose was prepared, placed into 500 mL volume shaking flask and sterilized by autoclave. The flask was returned to a room temperature and the *Pseudomonas cichorii* YN2 strain was inoculated and cultured with shaking at 125 stroke/min at 30° C. When turbidity at 600 nm became 0.1, dicyclopropylketone was added with well stirring so that the concentration is adjusted to 0.05% (v/v), then the shake culturing was continued. After 14 hours, the bacteria were recovered by centrifugal separation.

Then, 200 mL of the M9 medium containing 0.5% (w/v) glucose was prepared, placed into 500 mL volume shaking flask and sterilized by autoclave. The flask was returned to a room temperature and n-amylbenzene sterilized by a filter was added with well stirring so that the concentration is adjusted to 0.1% (v/v), then the recovered bacteria was resuspended in the medium and cultured with shaking at 125 stroke/min at 30° C. After 90 hours, the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain 47 mg of the PHA.

The molecular weight of this PHA obtained by performing the GPR analysis using the method similar to Example 16. Consequently, this was Mn=56000, Mw=118000. When performing the 1H-NMR analysis of the PHA obtained using the method similar to Example 16, it was confirmed to be the PHA containing 33% 3-hydroxy-5-phenylvaleric acid unit and saturated or unsaturated 4 to 12 carbon length 3-hydroxyalkanoic acids as the other unit.

Example 46

200 mL of the M9 medium containing 0.5% (w/v) polypeptone was prepared, placed into 500 mL volume shaking flask and sterilized by autoclave. The flask was returned to a room temperature and the *Pseudomonas cichorii* YN2 strain was inoculated and cultured with shaking 125 stroke/min at 30° C. When turbidity at 600 nm became 0.1, dicyclopropylketone was added with well stirring so that the concentration is adjusted to 0.05% (v/v), then the shake culturing was continued. After 14 hours, the bacteria were recovered by centrifugal separation.

Then, 200 mL of the M9 medium containing 0.5% (w/v) glucose but not containing NH$_4$Cl as a nitrogen source was prepared, placed into 500 mL volume shaking flask and sterilized by autoclave. The flask was returned to a room temperature and n-amylbenzene sterilized by a filter was added with well stirring so that the concentration is adjusted to 0.1% (v/v), then the recovered bacteria was resuspended in the medium and cultured with shaking at 125 stroke/min at 30° C. After 90 hours, the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain 150 mg of the PHA.

The molecular weight of the PHA obtained by performing the GPR analysis using the method similar to Example 16. Consequently, this was Mn=64000, Mw=134000. When performing the 1H-NMR analysis of the PHA obtained using the method similar to Example 16, it was confirmed to be the PHA containing 77% 3-hydroxy-5-phenylvaleric acid unit and saturated or unsaturated 4 to 12 carbon length 3-hydroxyalkanoic acids as the other unit.

Example 47

200 mL of the M9 medium containing 0.5% (w/v) polypeptone was prepared, placed into 500 mL volume shaking flask and sterilized by autoclave. The flask was returned to a room temperature and the *Pseudomonas cichorii* YN2 strain was inoculated and cultured with shaking at 125 stroke/min at 30° C. When turbidity at 600 nm became 0.1, dicyclopropylketone was added with well stirring so that the concentration is adjusted to 0.05% (v/v), then the shake culturing was continued. After 14 hours, the bacteria were recovered by centrifugal separation.

Then, 200 mL of the M9 medium containing 0.5% (w/v) glucose was prepared, placed into 500 mL volume shaking flask and sterilized by autoclave. The flask was returned to a room temperature and n-amylbenzene sterilized by a filter was added with well stirring so that the concentration is adjusted to 0.1% (v/v), then the recovered bacteria was resuspended in the medium and cultured with shaking at 125 stroke/min at 30° C. After 90 hours, the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membrane filter with the pore size of 0.45 μm, the filtrate was concentrated using a rotary evaporator, the concentrate was reprecipitated in cold methanol, further only the precipitate was recovered and dried in vacuo to obtain 117 mg of the PHA.

The molecular weight of this PHA obtained by performing the GPR analysis using the method similar to Example 16. Consequently, this was Mn=63000, Mw=126000. When performing the 1H-NMR analysis of the PHA obtained using the method similar to Example 16, it was confirmed to be the PHA containing 83% 3-hydroxy-5-phenylvaleric acid unit and saturated or unsaturated 4 to 12 carbon length 3-hydroxyalkanoic acids as the other unit.

Example 48

200 mL of the M9 medium containing 0.5% (w/v) glucose was prepared, placed into 500 mL volume shaking flask and sterilized by autoclave. The flask was returned to a room temperature and n-amylbenzene sterilized by a filter was added with well stirring so that the concentration is adjusted to 0.1% (v/v), then the *Pseudomonas cichorii* YN2 strain was inoculated and cultured with shaking at 125 stroke/min at 30° C. When turbidity at 600 nm became 0.1, dicyclopropylketone was added with well stirring so that the concentration is adjusted to 0.05% (v/v), then the shake culturing was continued. After 14 hours, the bacteria were recovered by centrifugal separation.

Then, 200 mL of the M9 medium containing 0.5% (w/v) glucose but not containing NH$_4$Cl as a nitrogen source was prepared, placed into 500 mL volume shaking flask and sterilized by autoclave. The flask was returned to a room temperature and n-amylbenzene sterilized by a filter was added with well stirring so that the concentration is adjusted to 0.1% (v/v), dicyclopropylketone was added with well stirring so that the concentration is adjusted to 0.05% (v/v), them the recovered bacteria was resuspended in the medium and cultured with shaking at 125 stroke/min at 30° C. After 90 hours, the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membrane filter with the pore size of 0.45 μm, the filtrate was concentrated using a rotary evaporate, the concentrate was reprecipitated in cold methanol, further only the precipitate was recovered and dried in vacuo to obtain 3 mg of the PHA.

The molecular weight of this PHA obtained by performing the GPR analysis using the method similar to Example 16. Consequently, this was Mn=43000, Mw=90000. When performing the 1H-NMR analysis of the PHA obtained using the method similar to Example 16, it was confirmed to be the PHA containing 88% 3-hydroxy-5-phenylvaleric acid unit and saturated or unsaturated 4 to 12 carbon length 3-hydroxyalkanoic acids as the other unit.

Example 49

200 mL of the M9 medium containing 0.5% (w/v) glucose was prepared, placed into 500 mL volume shaking flask and sterilized by autoclave. The flask was returned to a room temperature and n-amylbenzene sterilized by a filter was added with well stirring so that the concentration is adjusted to 0.1% (v/v), then the *Pseudomonas cichorii* YN2 strain was inoculated and culteured with shaking at 125 stroke/min at 30° C. When turbidity at 600 nm became 0.1, dicyclopropylketone was added with well stirring so that the concentration is adjusted to 0.05% (v/v), then the shake culturing was continued. After 14 hours, the bacteria were recovered by centrifugal separation.

Then, 200 mL of the M9 medium containing 0.5% (w/v) glucose was prepared, placed into 500 mL volume shaking flask and sterilized by autoclave. The flask was returned to a room temperature and n-amylbenzene sterilized by a filter was added with well stirring so that the concentration is adjusted to 0.1% (v/v), dicyclopropylketone was added with well stirring so that the concentration is adjusted to 0.05% (v/v), then the recovered bacteria was resuspended in the medium and cultured with shaking at 125 stroke/min at 30° C. After 90 hours, the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membrane filter with the pore size of 0.45 µm, the filtrate was concentrated using a rotary evaporator, the concentrate was reprecipitated in cold methanol, further only the precipitate was recovered and dried in vacuo to obtain 54 mg of the PHA.

The molecular weight of this PHA obtained by performing the GPR analysis using the method similar to Example 16. Consequently, this was Mn=30000, Mw=66000. When performing the 1H-NMR ayalysis of the PHA obtained using the method similar to Example 16, it was confirmed to be the PHA containing 76% 3-hydroxy-5-phenylvaleric acid unit and saturated or unsaturated 4 to 12 carbon length 3-hydroxyalkanoic acids as the other unit.

Example 50

200 mL of the M9 medium containing 0.5% (w/v) glucose was prepared, placed into 500 mL volume shaking flask and sterilized by autoclave. The flask was returned to a room temperature and the *Pseudomonas cichorii* YN2 strain was inoculated and cultured with shaking at 125 stroke/min at 30° C. When turbidity at 600 nm became 0.1, dicyclopropylketone was added with well stirring so that the concentration is adjusted to 0.05% (v/v), then the shake culturing was continued. After 14 hours, the bacteria were recovered by centrifugal separation.

Then, 200 mL of the M9 medium containing 0.5% (w/v) glucose but not containing $NH_4Cl$ as a nitrogen source was prepared, placed into 500 mL volume shaking flask and sterilized by autoclave. The flask was returned to a room temperature and n-amylbenzene sterilized by a filter was added with well stirring so that the concentration is adjusted to 0.1% (v/v), dicyclopropylketone was added with well stirring so that the concentration is adjusted to 0.05% (v/v), then the recovered bacteria was resuspended in the medium and cultured with shaking at 125 stroke/min at 30° C. After 90 hours, the bacteria were recovered by centrifugal separation, washed once with cold methanol and lyophilized.

This lyophilized pellet was suspended in 20 mL of chloroform and stirred at 60° C. for 20 hours to extract PHA. After the extract was filtered through a membrane filter with the pore size of 0.45 µm, the filtrate was concentrated using a rotary evaporator, the concentrate was reprecipitated in cold methanol, further only the precipitate was recovered and dried in vacuo to obtain 5 mg of the PHA.

The molecular weight of this PHA obtained by performing the GPR analysis using the method similar to Example 16. Consequently, this was Mn=40000, Mw=84000. When performing the 1H-NMR analysis of the PHA obtained using the method similar to Example 16, it was confirmed to be the PHA containing 87%-hydroxy-5-phenylvaleric acid unit and saturated or unsaturated 4 to 12 carbon length 3-hydroxyalkanoic acids as the other unit.

Example 51

200 mL of then M9 medium containing 0.5% (w/v) glucose was prepared, placed into 500 ml volume shaking flask and sterilized by autoclave. The flask was returned to a room temperature and the *Pseudomonas cichirii* YN2 strain was inoculated and cultured with shaking at 125 stroke/min at 30° C. When turbidity at 600 nm became 0.1, dicyclopropylketone was added with well stirring so that the concentration is adjusted to 0.05% (v/v), then the shake culturing was continued. After 14 hours, the bacteria were recovered by centrifugal separation.

Then, 200 mL of the M9 medium containing 0.5% (w/v) glucose was prepared, placed into 500 mL volume shaking flask and sterilized by autoclave. The flask was returned to a room temperature and n-amylbenzene sterilized by a filter was added with well stirring so that the concentration is adjusted to 0.1% (v/v), dicyclopropylketone was added with well stirring so that the concentration is adjusted to 0.05% (v/v), then the recovered bacteria was resuspended in the medium and cultured with shaking at 125 stroke/min at 30+ C. After 90 hours, the bacteria were recovered by centrifugal separation, washed once with cold methanol and lyophilized.

This lyophilized pellet was suspended in 20 mL of chroloform and stirred at 60° C. for 20 hours to extract PHA. After the extract was filtered through a membrane filter with the pore size of 0.45 µm, the filtrate was concentrated using a rotary evaporator, the concentrate was reprecipitated in cold methanol, further only the precipitate was recovered and dried in vacuo to obtain 26 mg of the PHA.

The molecular weight of this PHA obtained by performing the GPR analysis using the method similar to Example 16. Consequently, this was Mn=43000, Mw=77000. When performing the 1H-NMR analysis of the PHA obtained using the method similar to Example 16, it was confirmed to be the PHA containing 30% 3-hydroxy-5-phenylvaleric acid unit and saturated or unsaturated 4 to 12 carbon length 3-hydroxyalkanoic acids as the other unit.

What is claimed is:

1. A polyhydroxyalkanoate having a composition of monomer units represented by the following formula [1]:

$$A_xB_{(1-x)} \quad [1]$$

wherein A is at least one or more represented by the following chemical formula [2]; B is at least one or more selected from monomer units represented by the following chemical formula [3] or [4]; and x is 0.01 or more and not exceed 1,

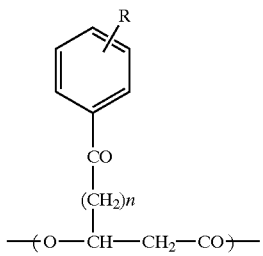

[2]

wherein n is any integer of 1 to 8; and R is any one selected from the group consisting of a halogen atom, —CN, —NO$_2$, —CH$_3$, —C$_2$H$_5$, —C$_3$H$_7$, —CF$_3$, —C$_2$F$_5$ and —C$_3$F$_7$),

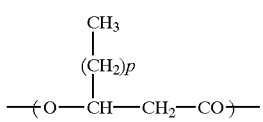

[3]

wherein p is any integer of 0 to 10, and

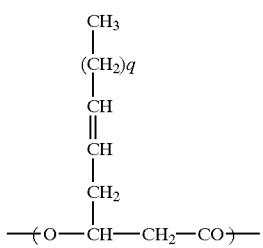

[4]

wherein q is an integer of either 3 or 5.

2. The polyhydroxyalkanoate according to claim 1, comprising a monomer unit represented by the following formula [5]:

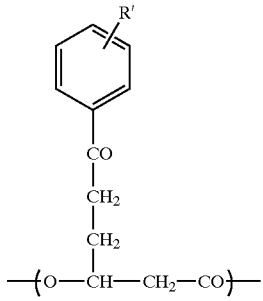

[5]

wherein R' is any one selected from the group consisting of a halogen atom, —CN, —NO$_2$, —CH$_3$, —C$_2$H$_5$, —C$_3$H$_7$, —CF$_3$, —C$_2$F$_5$ and —C$_3$F$_7$.

3. The polyhydroxyalkanoate according to claim 2, comprising monomer units represented by the following formula [6]:

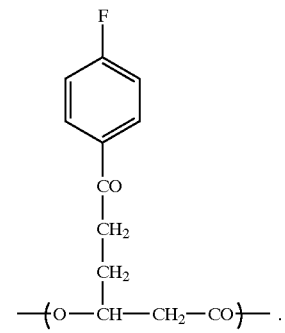

[6]

4. The polyhydroxyalkanoate according to claim 1, wherein number average molecular weight is 5,000 to 500,000.

5. A method for manufacturing polyhydroxyalkanoate having a composition of monomer units represented by the following formula [1] comprising the steps of:

preparing a medium containing a substituted benzoylalkanoic acid and;

culturing a microorganism capable of synthesizing the polyhydroxyalkanoate having said composition using said substituted benzoyl alkanoic acid in said medium, $$A_xB_{(1-x)}$$ [1]

wherein A is at least one or more represented by the following chemical formula [2]; B is at least one or more selected from monomer units represented by the following chemical formula [3] or [4]; and x is 0.01 or more and not exceed 1,

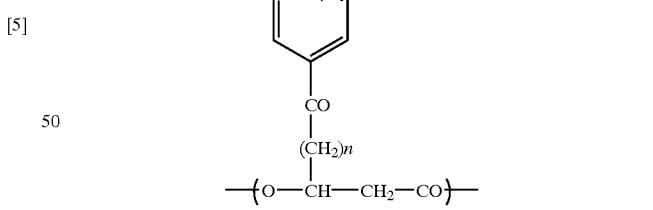

[2]

wherein n is any integer of 1 to 8; and R is any one selected from the group consisting of a halogen atom, —CN, NO$_2$, —CH$_3$, —C$_2$H$_5$, —C$_3$H$_7$, —CF$_3$, —C$_2$F$_5$ and —C$_3$F$_7$,

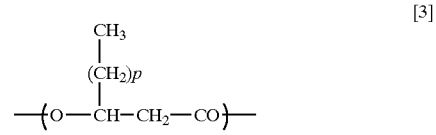

[3]

wherein p is any integer of 0 to 10, and

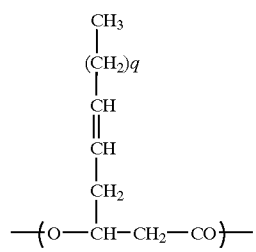

wherein q is an integer of either 3 or 5.

6. The method for manufacturing polyhydroxyalkanoate according to claim 5, wherein said substituted benzoylalkanoic acid is the substituted benzoylalkanoic acid represented by the following chemical formula [7] and the polyhydroxyalkanoate is a olyhydroxyalkanoate comprising monomer units represented by the following chemical formula [8]:

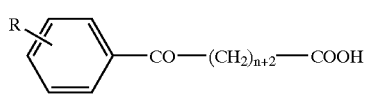

wherein n is any integer of 1 to 8; and R is any one selected from the group consisting of a halogen atom, —CN, $NO_2$, —$CH_3$, —$C_2H_5$, —$C_3H_7$, —$CF_3$, —$C_2F_5$ and —$C_3F_7$, and

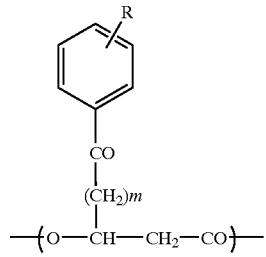

wherein m is at least one or more selected from the group consisting of n, n-2, n-4 and n-6 and represents an integer of one or more; n is any integer of 1 to 8 corresponding to n in chemical formula [7]; and R is the same as R in chemical formula [7].

7. The method for manufacturing polyhydroxyalkanoate according to claim 6, wherein the method comprises the step of culturing a microorganism producing the polyhydroxyalkanoate comprising monomer units represented by the following chemical formula [5'] using a substituted benzoylvaleric acid in the medium containing a substituted benzoylvaleric acid represented by the following chemical formula [9], and the produced polyhydroxyalkanoate comprises the monomer units represented by the following chemical formula [5'],

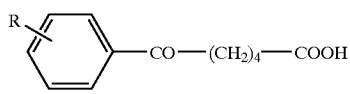

wherein R is any one selected from the group consisting of a halogen atom, —CN, $NO_2$, —$CH_3$, —$C_2H_5$, —$C_3H_7$, —$CF_3$, —$C_2F_5$ and —$C_3F_7$, and

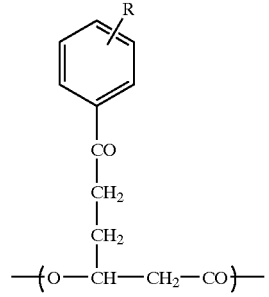

wherein R is any one selected from the group consisting of a halogen atom, —CN, —$NO_2$, —$CH_3$, —$C_2H_5$, —$C_3H_7$, —$CF_3$, —$C_2F_5$ and —$C_3F_7$ corresponding to R in said chemical formula [9].

8. The method for manufacturing polyhydroxyalkanoate according to claim 7, wherein the method comprises the steps of culturing a microorganism producing the polyhydroxyalkanoate comprising monomer units represented by the following chemical formula [6] using 5-(4-fluorobenzoyl)valeric acid in the medium containing 5-(4-fluorobenzoyl)valeric acid represented by the following chemical formula [10], and the produced polyhydroxyalkanoate comprises the monomer units represented by the following chemical formula [6],

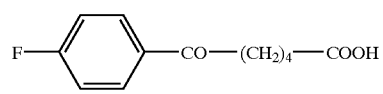

and

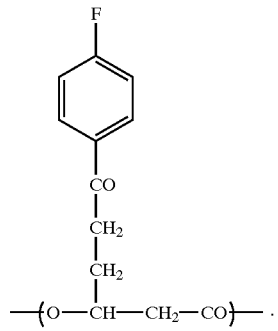

9. The method for manufacturing polyhydroxyalkanoate according to claim 5, wherein said medium further contains a saccharide.

10. The method for manufacturing polyhydroxyalkanoate according to claim 9, wherein said culturing step consists of one step of culturing said microorganism in said medium containing the substituted benzoylalkanoic acid and the saccharide.

11. The method for manufacturing polyhydroxyalkanoate according to claim 10, wherein the saccharide is glucose.

12. The method for manufacturing polyhydroxyalkanoate according to claim 9, wherein said culturing step is comprised of at least two steps of culturing said microorganism in said medium containing the substituted benzoylalkanoic acid and the saccharide and subsequently culturing said microorganism in a medium containing the substituted benzoylalkanoic acid and a saccharide.

13. The method for manufacturing polyhydroxyalkanoate according to claim 12, wherein the saccharide is glucose.

14. The method for manufacturing polyhydroxyalcanoate according to claim 12, wherein said subsequent culturing step is conducted in the absence of nitrogen source.

15. The method for manufacturing polyhydroxyalkanoate according to claim 9, wherein the saccharide is glucose.

16. The method for manufacturing polyhydroxyalkanoate according to claim 5, wherein said medium further contains an organic acid involved in TCA cycle.

17. The method for manufacturing polyhydroxyalkanoate according to claim 16, wherein said culturing step consists of one step of culturing said microorganism in the medium containing the substituted benzoylalkanoic acid and the organic acid involved in TCA cycle.

18. The method for manufacturing polyhydroxyalkanoate according to claim 17, wherein said organic acid involved in TCA cycle is malic acid or its salt.

19. The method for manufacturing polyhydroxyalkanoate according to claim 16, wherein said culturing step is comprised of the steps of:

culturing said microorganism in said medium and subsequently culturing said microorganism in said medium.

20. The method for manufacturing polyhydroxyalkanoate according to claim 19, wherein said organic acid involved in TCA cycle is malic acid or its salt.

21. The method for manufacturing polyhydroxyalkanoate according to claim 19, wherein said subsequent culturing step is conducted in the absence of nitrogen source.

22. The method for manufacturing polyhydroxyalkanoate according to claim 16, wherein said organic acid involved in TCA cycle is malic acid or its salt.

23. The method for manufacturing polyhydroxyalkanoate according to claim 5, wherein said medium further contains yeast extract.

24. The method for manufacturing polyhydroxyalkanoate according to claim 5, wherein said medium further contains polypeptone.

25. The method for manufacturing polyhydroxyalkanoate according to claim 5, further comprising the step of isolating polyhydroxyalkanoate produced by said microorganism.

26. The method for manufacturing polyhydroxyalkanoate according to claim 5, wherein said microorganism belongs to genus Pseudomonas.

27. The method for manufacturing polyhydroxyalkanoate according to claim 26, wherein said microorganism is at least one strain selected from the group consisting of *Pseudomonas cichorii* H45 strain (FERM BP-7374), *Pseudomonas cichorii* YN2 strain (FERM BP-7375), and *Pseudomonas jessenii* P161 strain (FERM BP-7376).

\* \* \* \* \*

UNITED STATES PATENT AND TRADEMARK OFFICE
CERTIFICATE OF CORRECTION

PATENT NO.       : 6,635,782 B2
APPLICATION NO.  : 09/951720
DATED            : October 21, 2003
INVENTOR(S)      : Tsutomu Honma et al.

It is certified that error appears in the above-identified patent and that said Letters Patent is hereby corrected as shown below:

COLUMN 1:

Line 42, "followings." should read --following.--.

COLUMN 3:

Line 21, "biosynthesis" should read --biosynlhesis".--;
Line 30, "In" should read --in--;
Line 47, "(31.64" should read --(31.64%--; and
Line 63, "is" should read --are--.

COLUMN 4:

Line 28, "an" should read --as--;
Line 40, "No. 2969175," should read --No. 2989175,--;
Line 47, "above described" should read --above-described--; and
Line 49, "These" should read --This--.

COLUMN 5:

Line 64, "will" should read --with--.

COLUMN 6:

Line 12, "others" should read --other--.

COLUMN 7:

Line 5, close up right margin; and
Line 26, "—$C_2F_7$" should read -- —$C_3F_7$--.

COLUMN 10:

Line 66, "$NO_2$group," should read --$NO_2$ group,--.

UNITED STATES PATENT AND TRADEMARK OFFICE
CERTIFICATE OF CORRECTION

| | | |
|---|---|---|
| PATENT NO. | : 6,635,782 B2 | |
| APPLICATION NO. | : 09/951720 | |
| DATED | : October 21, 2003 | |
| INVENTOR(S) | : Tsutomu Honma et al. | |

It is certified that error appears in the above-identified patent and that said Letters Patent is hereby corrected as shown below:

COLUMN 11:

Line 12, "1.1%" should read --0.1%--;
Line 21, "imylbenzene" should read --amyibenzene--;
Line 24, "3C-MS" should read --GC-MS--;
Line 32, "In" should read --in--;
Line 57, "sacharides" should read --saccharides--;
Line 63, "sacharides" should read --saccharides--; and
Line 67, "sacharides" should read --saccharides--.

COLUMN 12:

Line 67, "above described" should read --above-described--.

COLUMN 13:

Line 33, "examples" should read --example--;
Line 38, "No." should read
 --No. 7-48438, Japanese Patent Application Laid-Open No.--;
Line 43, "above described" should read --above-described--; and
Line 56, "above" should read --above- --.

UNITED STATES PATENT AND TRADEMARK OFFICE
CERTIFICATE OF CORRECTION

PATENT NO. : 6,635,782 B2
APPLICATION NO. : 09/951720
DATED : October 21, 2003
INVENTOR(S) : Tsutomu Honma et al.

It is certified that error appears in the above-identified patent and that said Letters Patent is hereby corrected as shown below:

COLUMN 16:

Lines 24-59,

"  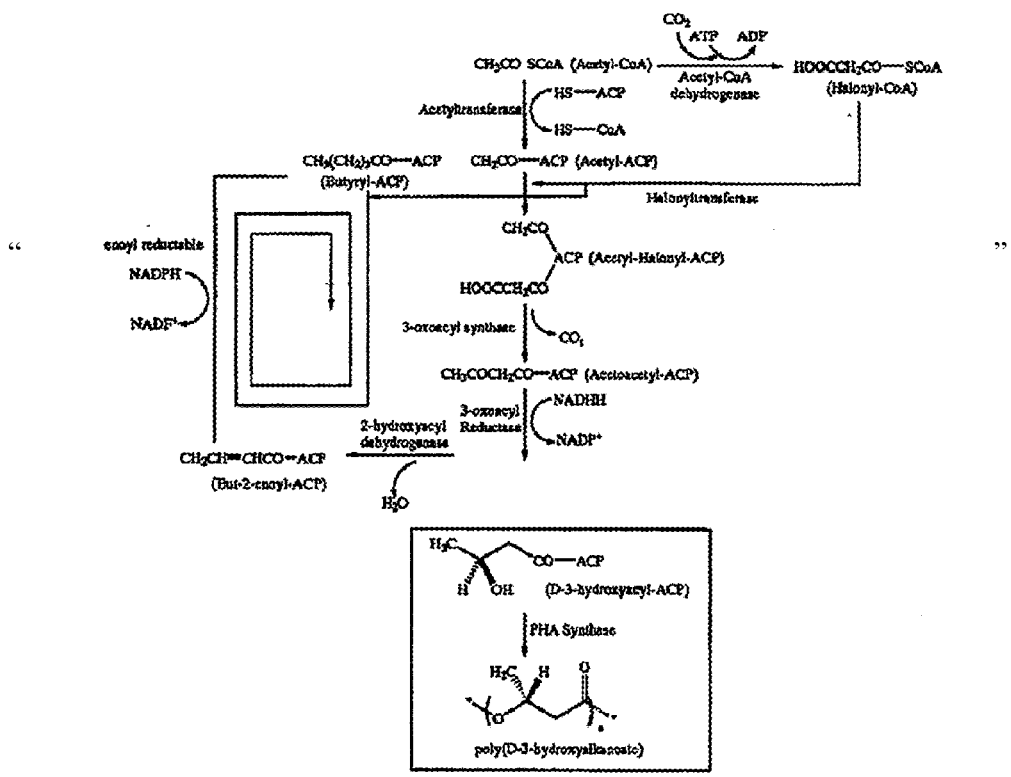  "

should read

UNITED STATES PATENT AND TRADEMARK OFFICE
CERTIFICATE OF CORRECTION

PATENT NO. : 6,635,782 B2
APPLICATION NO. : 09/951720
DATED : October 21, 2003
INVENTOR(S) : Tsutomu Honma et al.

It is certified that error appears in the above-identified patent and that said Letters Patent is hereby corrected as shown below:

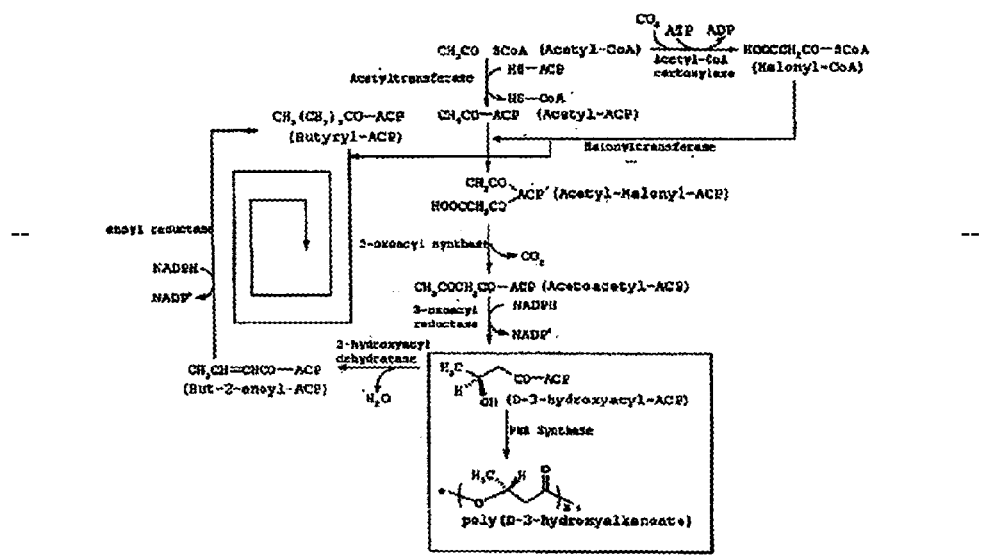

COLUMN 17:

Line 32, "such" should read --such as--; and
Line 38, "Phophoenolpyruvic" should read –Phosphoenolpyruvic--.

COLUMN 18:

Line 13, "then" should read --than--;
Line 18, "fatty" should read --a fatty--;
Line 20, "ing" should read --ed-- and "acid by" should read --acid. By--;
Line 34, "energy" should read --energy source--;
Line 57, "above described" should read --above-described--;
Line 58, "above described" should read --above-described-- and
      "benzoyla-" should read --beuzoyl- --;
Line 59, "lkaoic" should read --alkanoic--; and
Line 64, "above described" should read --above-described--.

UNITED STATES PATENT AND TRADEMARK OFFICE
CERTIFICATE OF CORRECTION

| | | |
|---|---|---|
| PATENT NO. | : 6,635,782 B2 | |
| APPLICATION NO. | : 09/951720 | |
| DATED | : October 21, 2003 | |
| INVENTOR(S) | : Tsutomu Honma et al. | |

It is certified that error appears in the above-identified patent and that said Letters Patent is hereby corrected as shown below:

COLUMN 19:

Line 12, "above described" should read --above-described--;
Line 18, "cell;" should read --cell:--; and
Line 47, "gluconate;" should read --gluconate:--.

COLUMN 20:

Line 42, "esoulin:" should read --esculine:--;
Line 45, "agar;" should read --agar:--; and
Line 62, "above described" should read --above-described--.

COLUMN 21:

Line 9, "be" should read --the--; and
Line 52, "disacoharides" should read --disaccharides--.

COLUMN 22:

Line 2, "above described" should read --above-described--;
Line 46, "above described" should read --above-described--; and
Line 66, "it" should be deleted.

COLUMN 23:

Line 20, "above described" should read --above-described--.

COLUMN 25:

Line 28, "above described" should read --above-described--;
Line 31, "above described" should read --above-described--;
Line 37, "microorganisms," should read --microoganism,--;
Line 40, "above described" should read --above-described--; and
Line 43, "above described" should read --above-described--.

UNITED STATES PATENT AND TRADEMARK OFFICE
CERTIFICATE OF CORRECTION

PATENT NO. : 6,635,782 B2
APPLICATION NO. : 09/951720
DATED : October 21, 2003
INVENTOR(S) : Tsutomu Honma et al.

It is certified that error appears in the above-identified patent and that said Letters Patent is hereby corrected as shown below:

COLUMN 27:

Line 33, "above described" should read --above-described--;
    Line 50, "above described" should read --above-described--;
    Line 54, "above described" should read --above-described--; and
    Line 58, "with in" should read --within--.

COLUMN 28:

Line 15, "as" should read --as a--;
    Line 32, "Dycyclopropylketone" should read --Dicyclopropylketone--;
    Line 38, "is it." should read --it is.--;
    Line 45, "above described" should read --above-described--; and
    Line 64, "organism" should read --organisms--.

COLUMN 29:

Line 33, "limited a" should read --a limited--; and
    Line 37, "above described" should read --above-described--.

COLUMN 31:

Line 2, "above described" should read --above-described--;
    Line 12, "above described" should read --above-described--; and
    Line 25, "abbrivated" should read --abbreviated--.

COLUMN 37:

Line 34, "end" should read --and--.

COLUMN 41:

Line 60, "19 medium" should read --M9 medium--.

COLUMN 44:

Line 24, "cometimes" should read --sometimes--.

UNITED STATES PATENT AND TRADEMARK OFFICE
CERTIFICATE OF CORRECTION

PATENT NO. : 6,635,782 B2
APPLICATION NO. : 09/951720
DATED : October 21, 2003
INVENTOR(S) : Tsutomu Honma et al.

It is certified that error appears in the above-identified patent and that said Letters Patent is hereby corrected as shown below:

COLUMN 45:

Line 36, "vacuo" should read --in vacuo--.

COLUMN 49:

Line 53, "an" should read --as--.

COLUMN 52:

Line 7, "vacuo" should read --in vacuo--.

COLUMN 53:

Line 40, "n-amylvenzene" should read --n-amylbenzene--.

COLUMN 55:

Line 25, "Mw=23000." should read —Mw=238000.--.

COLUMN 57:

Line 38, "meduim" should read --medium--; and
Line 39, "place" should read --placed--.

COLUMN 58:

Line 21, "lyophilezed." should read --lyophilized.--; and
Line 63, "membrace" should read --membrane--.

COLUMN 59:

Line 13, "strilized" should read --sterilized--; and
Line 65, "n-amylvenzene" should read --n-amylbenzene--.

COLUMN 60:

Line 35, "n-anylbenzene" should read --n-amylbenzene--.

UNITED STATES PATENT AND TRADEMARK OFFICE
CERTIFICATE OF CORRECTION

PATENT NO.        : 6,635,782 B2
APPLICATION NO. : 09/951720
DATED              : October 21, 2003
INVENTOR(S)      : Tsutomu Honma et al.

It is certified that error appears in the above-identified patent and that said Letters Patent is hereby corrected as shown below:

COLUMN 62:

Line 52, "them" should read --then--.

COLUMN 63:

Line 12, "culteured" should read --cultured--; and
Line 39, "ayalysis" should read --analysis--.

COLUMN 64:

Line 28, "*cichirii*" should read --*cichorli*--; and
Line 51, "chrolo-" should read --chloro--

COLUMN 66:

Line 58, "not" should read --does not--.

COLUMN 67:

Line 16, "—$C_3F_7$)," should read -- —$C_3F_7$,--.

COLUMN 68:

Line 40, "not" should read --does not--.

UNITED STATES PATENT AND TRADEMARK OFFICE
CERTIFICATE OF CORRECTION

PATENT NO. : 6,635,782 B2
APPLICATION NO. : 09/951720
DATED : October 21, 2003
INVENTOR(S) : Tsutomu Honma et al.

It is certified that error appears in the above-identified patent and that said Letters Patent is hereby corrected as shown below:

COLUMN 69:

Line 19, "olyhydroxyalkanoate" should read --polyhydroxyalkanoate--.

Signed and Sealed this

Twenty-eighth Day of November, 2006

JON W. DUDAS
*Director of the United States Patent and Trademark Office*

SEQUENCE LISTING

<160> NUMBER OF SEQ ID NOS: 1

<210> SEQ ID NO 1
<211> LENGTH: 1501
<212> TYPE: DNA
<213> ORGANISM: Pseudomonas jessenii P161 strain.

<400> SEQUENCE: 1

```
tgaacgctgg cggcaggcct aacacatgca agtcgagcgg atgacgggag cttgctcctg      60
aattcagcgg cggacgggtg agtaatgcct aggaatctgc ctggtagtgg gggacaacgt     120
ctcgaaaggg acgctaatac cgcatacgtc ctacgggaga aagcagggga ccttcgggcc     180
ttgcgctatc agatgagcct aggtcggatt agctagttgg tgaggtaatg gctcaccaag     240
gcgacgatcc gtaactggtc tgagaggatg atcagtcaca ctggaactga gacacggtcc     300
agactcctac gggaggcagc agtggggaat attggacaat gggcgaaagc ctgatccagc     360
catgccgcgt gtgtgaagaa ggtcttcgga ttgtaaagca ctttaagttg ggaggaaggg     420
cattaaccta atacgttagt gttttgacgt taccgacaga ataagcaccg gctaactctg     480
tgccagcagc cgcggtaata cagagggtgc aagcgttaat cggaattact gggcgtaaag     540
cgcgcgtagg tggtttgtta agttggatgt gaaagcccg ggctcaacct gggaactgca     600
ttcaaaactg acaagctaga gtatggtaga gggtggtgga atttcctgtg tagcggtgaa     660
atgcgtagat ataggaagga acaccagtgg cgaaggcgac cacctggact gatactgaca     720
ctgaggtgcg aaagcgtggg gagcaaacag gattagatac cctggtagtc cacgccgtaa     780
acgatgtcaa ctagccgttg ggagccttga gctcttagtg gcgcagctaa cgcattaagt     840
tgaccgcctg gggagtacgg ccgcaaggtt aaaactcaaa tgaattgacg ggggcccgca     900
caagcggtgg agcatgtggt ttaattcgaa gcaacgcgaa gaaccttacc aggccttgac     960
atccaatgaa ctttccagag atggatgggt gccttcggga acattgagac aggtgctgca    1020
tggctgtcgt cagctcgtgt cgtgagatgt tgggttaagt cccgtaacga gcgcaaccct    1080
tgtccttagt taccagcacg taatggtggg cactctaagg agactgccgg tgacaaaccg    1140
gaggaaggtg gggatgacgt caagtcatca tggcccttac ggcctgggct acacacgtgc    1200
tacaatggtc ggtacagagg gttgccaagc cgcgaggtgg agctaatccc acaaaaccga    1260
tcgtagtccg gatcgcagtc tgcaactcga ctgcgtgaag tcggaatcgc tagtaatcgc    1320
gaatcagaat gtcgcggtga atacgttccc gggccttgta cacaccgccc gtcacaccat    1380
gggagtgggt tgcaccagaa gtagctagtc taaccttcgg gaggacggtt accacggtgt    1440
gattcatgac tggggtgaag tcgtaccaag gtagccgtag gggaacctgc ggctggatca    1500
c                                                                      1501
```